United States Patent [19]
Furuya et al.

[11] Patent Number: 5,744,479
[45] Date of Patent: Apr. 28, 1998

[54] THIENOPYRIDINE COMPOUNDS WHICH HAVE USEFUL PHARMACEUTICAL ACTIVITY

[75] Inventors: Shuichi Furuya; Nobuo Choh; Masataka Harada; Satoshi Sasaki, all of Tsukuba, Japan

[73] Assignee: Takeda Chemical Industries, Ltd., Osaka, Japan

[21] Appl. No.: 779,608

[22] Filed: Jan. 7, 1997

[30] Foreign Application Priority Data

Oct. 19, 1995 [JP] Japan .................................. 7-271639

[51] Int. Cl.⁶ ........................ A61K 31/33; C07D 419/02
[52] U.S. Cl. ............................................ 514/301; 546/114
[58] Field of Search ............................... 576/114; 514/301

[56] References Cited

U.S. PATENT DOCUMENTS

| | | | |
|---|---|---|---|
| 4,659,691 | 4/1987 | Veber et al. | 514/11 |
| 5,140,009 | 8/1992 | Haviv et al. | 514/16 |
| 5,171,835 | 12/1992 | Janaky et al. | 530/313 |

FOREIGN PATENT DOCUMENTS

| | | |
|---|---|---|
| 0 443 568 | 2/1991 | European Pat. Off. |
| 0 520 423 | 12/1992 | European Pat. Off. |
| 61-191698 | 8/1986 | Japan . |
| 94/20460 | 9/1994 | WIPO . |
| 95/28405 | 10/1995 | WIPO . |

OTHER PUBLICATIONS

R.J. Bienstock et al., "Conformational Analysis of a Highly Potent Dicyclic Gonadotropin-Releasing Hormone Antagonist by Nuclear Magnetic Resonance and Molecular Dynamics", J. Med. Chem. vol. 36, (1993), pp. 3265–3273.

Seirigaku 2, Bunkodo, (1986), pp. 610–618., {partial translation}.

Receptor Kiso to Risho, Asakurashoten, (1993), pp. 297–304., {partial translation}.

P. M. Gilis et al., "Synthesis and Antibacterial Evaluation of 4,7-dihydro-4-oxothieno[2,3-b] pyridine-5-carboxylic Acids", Eur. J. Med. Chem., No. 3, May–Jun. (1978), pp. 265–269.

*Primary Examiner*—Zinna Northington Davis
*Attorney, Agent, or Firm*—Foley & Lardner

[57] ABSTRACT

The present thienopyrimidine derivatives and compositions having gonadotropin-releasing hormone antagonistic activity are useful as propylactics or therapeutic agents for the prevention or treatment of several hormone dependent diseases, for example, a sex hormone dependent cancer (e.g. prostatic cancer, uterine cervical cancer, breast cancer, pituitary adenoma), benign prostatic hypertrophy, myoma of the uterus, endometriosis, precocious puberty, amenorrhea, premenstrual syndrome, polycystic ovary syndrome and acne vulgaris; are effective as a fertility controlling agent in both sexes (e.g. a pregnancy controlling agent and a menstrual cycle controlling agent); can be used as a male or female contraceptive, as an ovulation-inducing agent; can be used as an infertility treating agent by using a rebound effect owing to a stoppage of administration thereof; and are useful for modulating estrous cycles in animals in the field of animal husbandry, as agents for improving the quality of edible meat or promoting the growth of animals; and as agents for promoting spawning in fish.

28 Claims, No Drawings

THIENOPYRIDINE COMPOUNDS WHICH HAVE USEFUL PHARMACEUTICAL ACTIVITY

This is a continuation application of PCT/JP96/08018 filed on Oct. 18, 1996.

TECHNICAL FIELD

The present invention relates to novel thieno[2,3-b] pyridine derivatives and salts thereof. The present invention further relates to methods for manufacturing these thieno[2,3-b]pyridine derivatives and the salts thereof, and pharmaceutical compositions containing these thieno[2-3,b] pyridine derivatives.

BACKGROUND ART

Secretion of anterior pituitary hormone is controlled by peripheral hormones secreted from target organs for the respective hormones and by secretion-accelerating or -inhibiting hormones from the hypothalamus, which is the upper central organ of the anterior lobe of the pituitary (in this specification, these hormones are collectively called "hypothalamic hormones"). At the present stage, as hypothalamic hormones, nine kinds of hormones have been confirmed including, for example, thyrotropin releasing hormone (TRH) or gonadotropin releasing hormone {GnRH: sometimes called LH-RH (luteinizing hormone releasing hormone)} (cf. Seirigaku 2, compiled by M. Iriku and K Toyama, published by Bunkohdo, pp.610–618, 1986). These hypothalamic hormones are assumed to show their actions via the receptor which is considered to exist in the anterior lobe of the pituitary (cf. ibid), and studies of receptor genes specific to these hormones, including those of humans, have been developed (Receptor Kiso To Rinshô, compiled by H. Imura, et al., published by Asakura Shoten, pp.297–304, 1993). Accordingly, antagonists or agonists specifically and selectively acting on these receptors control the action of hypothalamic hormone and the secretion of anterior pituitary hormone. As a result, they are expected to be useful as prophylactic and therapeutic agents of anterior pituitary hormone dependent diseases.

As compounds having a GnRH antagonistic activity, a number of compounds including, for example, derivatives of GnRH such as straight-chain peptides, (U.S. Pat. No. 5,140,009 and U.S. Pat. No. 5,171,835), cyclic hexapeptide derivatives [Japanese Patent Application Laid-open No. 61(1986)-191698] or bicyclic peptide derivatives [Journal of medicinal chemistry, Vol.36, pp.3265-3273, 1993] have been disclosed.

These compounds are, however, all peptides, which leave many problems including, for example, dosage forms, stability of drugs, durability of actions and stability on metabolism. Orally administrable GnRH antagonistic drugs, especially non-peptide ones, which has therapeutic effects for hormone-dependent cancer, e.g. prostate cancer, and for endometriosis and precocious puberty, but not to cause the transient pituitary-gonadotropic action (acute action) have been desired, are strongly desired.

The object of the invention lies in providing novel thieno [2,3-b]pyridine compounds having excellent gonadotropic hormone releasing hormone antagonistic activity as well as being excellent gonadotropic hormone releasing hormone antagonistic agents.

DISCLOSURE OF INVENTION

Thus, the present invention provides (1) A compound of the formula:

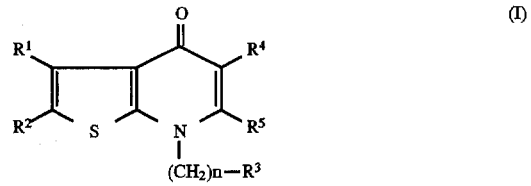

wherein each of $R^1$ and $R^2$ are hydrogen or a group bonded through a carbon atom, a nitrogen atom, an oxygen atom or a sulfur atom, $R^3$ is an optionally substituted homo-or hetero-cyclic group, $R^4$ is an optionally substituted heterocyclic group or a group bonded through a hetero atom, $R^5$ is hydrogen or a group bonded through a carbon atom, n is an integer of 0 to 3, with the proviso that when $R^4$ is tetrazolyl or a group bonded through a hetero atom and n is 1, $R^3$ is not a group of the formula:

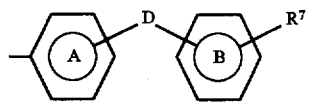

wherein $R^7$ is an optionally substituted 5–7 membered heterocyclic residue, having as a group capable of constituting the ring, carbonyl group, thiocarbonyl group, an optionally oxidized sulfur atom or a group convertible into them, D is a direct bond or a spacer having an atomic length of two or less between the ring B and the ring A, and A and B are independently an optionally substituted aromatic hydrocarbon residue optionally containing a hetero-atom or an optionally substituted heterocyclic residue, or a salt thereof, (2) A compound according to the item (1), wherein $R^1$ is a group bonded through a carbon atom or a nitrogen atom, (3) A compound according to the item (1), wherein $R^1$ is an optionally substituted $C_{1-20}$ hydrocarbon residue, (4) A compound according to the item (1), wherein $R^1$ is an optionally substituted $C_{1-6}$ alkyl group, (5) A compound according to the item (3), wherein $C_{1-20}$ hydrocarbon residue of $R^1$ is optionally substituted with (1) halogen, (2) nitro, (3) cyano, (4) an optionally substituted amino, (5) an optionally substituted hydroxyl group, (6) a group of the formula: —S(O)$_t$—$R^6$, wherein t denotes an integer of 0 to 2, and $R^6$ is a hydrogen atom or an optionally substituted hydrocarbon residue, (6) A compound according to the item (1), wherein $R^2$ is an optionally substituted $C_{1-20}$ hydrocarbon residue, (7) A compound according to the item (1), wherein $R^2$ is an optionally substituted $C_{6-14}$ aryl group, (8) A compound according to the item (6), wherein $C_{1-20}$ hydrocarbon residue of $R^2$ is optionally substituted with (1) an optionally substituted amino group, (2) an optionally substituted hydroxyl group, (3) an optionally substituted carbamoyl group, (4) an optionally substituted carboxyl group, (5) an optionally substituted alkenyl group, (6) acyl or (7) nitro, (9) A compound according to the item (1), wherein $R^3$ is an optionally substituted homo-cyclic group,

(10) A compound according to the item (9), wherein $R^3$ is an optionally substituted $C_{6-14}$ aryl group,

(11) A compound according to the item (9), wherein homo-cyclic group of $R^3$ is optionally substituted with (1) halogen, (2) nitro, (3) an optionally substituted hydroxyl group, (4) a group of the formula: —S(O)$_t$—$R^6$, wherein t denotes an integer of 0 to 2, and $R^6$ is a hydrogen atom or an optionally substituted hydrocarbon residue,

(12) A compound according to the item (1), wherein heterocyclic group of $R^4$ is 5- to 8-membered heterocyclic group,

(13) A compound according to the item (1), wherein heterocyclic group of $R^4$ is 5- to 8-membered heterocyclic group having at least one nitrogen atom in a ring,

(14) A compound according to the item (1), wherein the group bonded through hetero atom of $R^4$ is an optionally substituted amino group, an optionally substituted hydroxyl group or an optionally substituted mercapto group,

(15) A compound according to the item (1), wherein the substituent in the optionally substituted heterocyclic group of $R^4$ is (1) halogen, (2) nitro, (3) an optionally substituted hydroxyl group, (4) a group of the formula: —S(O)$_t$—$R^6$, wherein t denotes an integer of 0 to 2, and $R^6$ is a hydrogen atom or an optionally substituted hydrocarbon residue, (5) an optionally substituted amino, or (6) a $C_{1-10}$ hydrocarbon residue,

(16) A compound according to the item (14), wherein the optionally substituted amino group, the optionally substituted hydroxyl group or the optionally substituted mercapto group is (1) a $C_{1-10}$ hydrocarbon residue which may optionally be substituted by $C_{1-6}$ alkoxycarbonyl or carbamoyl, (2) a $C_{1-10}$ acyl group, or (3) a group of the formula: —S(O)$_t$—$R^6$, wherein t denotes an integer of 0 to 2, and $R^6$ is a hydrogen atom or an optionally substituted hydrocarbon residue,

(17) A compound according to the item (1), wherein $R^5$ is a hydrogen atom or an optionally substituted $C_{1-20}$ hydrocarbon residue,

(18) A compound according to the item (17), wherein hydrocarbon residue in the optionally substituted $C_{1-20}$ hydrocarbon residue is $C_{1-10}$ alkyl group,

(19) A compound according to the item (1), wherein $R^1$ is an alkyl group which may optionally be substituted with halogen or N—$C_{7-13}$ aralkyl-N—$C_{1-6}$ alkylamino, $R^2$ is a $C_{6-14}$ aryl group which may optionally be substituted with a group selected from the group consisting of (i) nitro, (ii) $C_{1-6}$ alkoxy and (iii) amino which may optionally be substituted with $C_{1-6}$ alkanoyl, $R^3$ is a mono- or di-halogeno-$C_{6-14}$ aryl group, $R^4$ is (1) a 5- or 6- membered heterocyclic group which has at least one nitrogen atom and one oxygen atom and which is bonded through a carbon atom, (2) a hydroxyl group which may optionally be substituted with a group selected from the group consisting of (i) $C_{1-6}$ alkyl which may optionally be substituted with $C_{1-6}$ alkoxy-carbonyl or carbamoyl, (ii) $C_{1-6}$ alkanoyl and (iii) $C_{1-6}$ alkylsulfonyl, (3) a group of the formula: —S(O)$_t$—$R^{6'}$, wherein t is an integer of 0 to 2 and $R^{6'}$ is $C_{1-6}$ alkyl, or (4) an amino group which may optionally be substituted with $C_{1-6}$ alkanoyl, $R^5$ is a hydrogen atom and n is 1,

(20) 3-(N-benzyl-N-methylaminomethyl)-4,7-dihydro-2-(4-methoxyphenyl)-5-(oxazol-5-yl)-7-(2-fluorobenzyl)-4-oxothieno[2,3-b]pyridine or its salt,

(21) 4,7-dihydro-2-(4-isobutyrylaminophenyl)-(3-(N-benzyl-N-methylaminomethyl)-5-isopropoxy-7-(2,6-difluorobenzyl)-4-oxothieno[2,3-b]pyridine or its salt,

(22) 4,7-dihydro-2-(4-isobutyrylaminophenyl)-3-(N-benzyl-N-methylaminomethyl)-5-isopropylsulfonyloxy-7-(2,6-difluorobenzyl)-4-oxothieno[2,3-b]pyridine or its salt,

(23) A method for producing a compound of the formula:

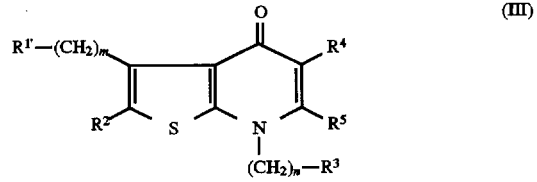

(III)

wherein $R^{1'}$ is a group bonded through a nitrogen atom, $R^2$, $R^3$, $R^4$ and $R^5$ have the same meaning as defined in the item (1), n is an integer of 0 to 3, m is an integer of 0 to 6, or a salt thereof, which comprises reacting a compound of the formula:

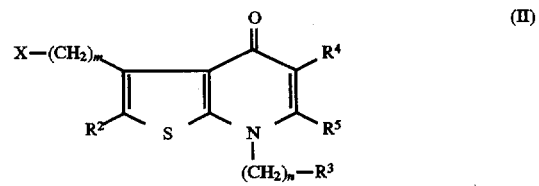

(II)

wherein X is a leaving group and the other group have the same meaning as defined above, with a compound of the formula:

$R^{1'}$—H wherein $R^{1'}$ has the same meaning as defined above,

(24) A pharmaceutical composition, which comprises a compound as defined in the item (1) and a carrier, excipient or diluent thereof,

(25) A pharmaceutical composition according to the item (24), which is for antagonizing gonadotropin-releasing hormone activity,

(26) A pharmaceutical composition according to the item (25), which is a composition for treating or preventing a sex hormone dependent disease,

(27) A method for treating a mammal suffering from a gonadotropin-releasing hormone derived disorder, which comprises administering an effective amount of a compound as defined in the item 1 to the mammal, and

(28) Use of a compound as defined in the item (1) for producing a pharmaceutical composition for antagonizing gonadotropin-releasing hormone activity in a mammal suffering from a sex hormone dependent disease.

The nucleus of the present compound, 4,7-dihydro-4-oxothieno[2,3-b]pyridine, is shown below;

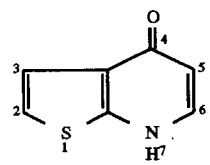

The group bonded through a carbon atom represented by $R^1$, $R^2$ or $R^5$ in the formula (I), (II) or (III) includes, for example, (1) a hydrocarbon residue, (2) an acyl group, (3) a carbamoyl group, and (4) a heterocyclic group which bonds through carbon atom of the heterocyclic group. Each of these groups may optionally be substituted. Furthermore, as the group bonded through a carbon atom, (5) a carboxyl group or an ester or amide thereof and (6) a cyano group are mentioned.

The ester of carboxyl group includes a group of the formula: —COO—$R^{11}$, wherein $R^{11}$ is a hydrogen atom, a hydrocarbon residue or a heterocyclic group. Each of these hydrocarbon residue and heterocyclic group may optionally be substituted.

The amide of carboxyl group includes a group of the formula; —CO—$NR^{12}R^{13}$, wherein $R^{12}$ is a hydrogen atom, a hydrocarbon residue or a heterocyclic group or a group bonded through a sulfur atom. $R^{13}$ represents a hydrogen atom or a hydrocarbon residue. $R^{12}$ and $R^{13}$ may form a 5 to 7 membered cyclic amino group together with the neighboring nitrogen atom or a nitrogen-containing heterocyclic group together with a neighboring nitrogen atom. Each of these hydrocarbon residue, heterocyclic group, cyclic amino group, nitrogen-containing heterocyclic group may optionally be substituted.

Examples of the group bonded through a nitrogen atom represented by $R^1$ and $R^2$ include (1) a nitro group, (2) a group of the formula: —$NR^{14}R^{15}$, wherein $R^{14}$ represents a hydrogen atom, a hydrocarbon residue, a hydrocarbon residue-oxy group, an acyl group, a hydroxyl group, a heterocyclic group, a group of the formula: —$SO_p$—$R^{16}$, wherein p denotes an integer of 1 or 2, and $R^{16}$ represents a hydrocarbon residue, $R^{15}$ represents a hydrogen or a hydrocarbon residue, and the group —$NR^{14}R^{15}$ may form a cyclic amino group. Each of these hydrocarbon residue, hydrocarbon residue-oxy group, acyl group, hydroxyl group, heterocyclic group and cyclic amino group may optionally be substituted.

Examples of the group bonded through an oxygen atom of $R^1$ and $R^2$ include a group of the formula: —O— $R^{17}$, wherein $R^{17}$ is a hydrogen atom, a hydrocarbon residue, an acyl group or a heterocyclic group. Each of these hydrocarbon residue, acyl group and heterocyclic group may optionally be substituted.

Examples of the group bonded through a sulfur atom of $R^1$, $R^2$ and $R^{12}$ include a group of the formula: —$S(O)_t$—$R^{18}$, wherein $R^{18}$ is a hydrogen atom, a hydrocarbon residue or a heterocyclic group, and t denotes an integer of 0 to 2. Each of these hydrocarbon residue and heterocyclic group may be optionally substituted.

Examples of the group bonded through a hetero atom includes a group bonded through a nitrogen atom, a group bonded through an oxygen atom and a group bonded through a sulfur atom. Those groups are the same as defined in $R^1$ and $R^2$.

The hydrocarbon residue in the hydrocarbon residue which may be optionally substituted and the hydrocarbon residue-oxy group which may optionally be substituted described above includes a hydrocarbon residue having one to 20 carbon atoms. As examples of the $C_{1-20}$ hydrocarbon residue, mention is made of (1) $C_{1-15}$ alkyl, e.g. methyl, ethyl, n-propyl, isopropyl, n-butyl, isobutyl, sec-butyl, t-butyl, pentyl, hexyl, heptyl, octyl, nonyl, decyl, undecyl, dodecyl, tridecyl, tetradecyl, pendadecyl, etc, and among others, with $C_{1-10}$ alkyl or $C_{1-6}$ alkyl being preferable; (2) $C_{3-10}$ cycloalkyl, e.g. cyclopropyl, cyclobutyl, cyclopentyl, cyclohexyl, cycloheptyl, cyclooctyl, cyclononyl, etc, and among others, with $C_{3-6}$ cycloalkyl being preferable; (3) $C_{2-10}$ alkenyl, e.g. vinyl, allyl, isopropenyl, 1-butenyl, 2-butenyl, 3-butenyl, 2-methylallyl, butadienyl, hexatrienyl, 3-octenyl, etc, and among others, with $C_{2-6}$ alkenyl being preferable, (4) $C_{2-10}$ alkynyl, e.g. ethynyl, 2-propynyl, isopropynyl, butynyl, t-butynyl, 3-hexynyl, etc, and among others, with $C_{2-6}$ alkynyl being preferable; (5) $C_{3-10}$ cycloalkenyl, e.g. cyclopropenyl, cyclopentenyl, cyclohexenyl, etc, among others, with $C_{3-6}$ cycloalkenyl being preferable; (6) $C_{6-14}$ aryl e.g. phenyl, 1- or 2-naphthyl, anthryl, phenanthryl, acenaphthyl, anthracenyl, etc., among others, with phenyl and naphthyl, being preferable; and (7) $C_{7-20}$ aralkyl, e.g. benzyl, phenethyl, benzhydryl, trityl, etc, and among others, with benzyl and phenethyl being preferable.

The substituents which said hydrocarbon residue may optionally have include (1) halogen, (2) nitro, (3) nitroso, (4) cyano, (5) a hydroxyl group which may optionally be substituted by (i) $C_{1-6}$ alkyl, which may optionally be substituted by hydroxyl, $C_{1-6}$ alkoxy, $C_{1-3}$ alkoxy-$C_{1-3}$ alkoxy, $C_{1-3}$ alkylthio, hydroxy-$C_{1-3}$ alkoxy, $C_{1-6}$ alkylcarbonyl, carboxyl, carbamoyl, $C_{1-6}$ alkyl-carbamoyl, 5 to 7 membered nitrogen containing heterocyclic group or halogen, (ii) $C_{1-4}$ acyl, (iii) $C_{7-20}$ aralkyl, which may optionally be substituted by halogen, $C_{1-3}$ alkoxy or $C_{1-4}$ alkyl, (iv) $C_{6-14}$ aryl, which may optionally be substituted by halogen, (v) $C_{2-6}$ alkenyl, (vi) $C_{3-7}$ cycloalkyl, (vii) $C_{1-3}$ alkoxycarbonyl, (viii) mono- or di-$C_{1-6}$ alkyl-amino, (ix) $C_{2-6}$ alkenyl-amino, (x) $C_{1-3}$ alkoxy-carbonyl, (xi) $C_{1-6}$ alkylcarbonyl, (xii) $C_{3-6}$ cycloalkyl-oxycarbonyl or (xiii) trifluorosulfonyl, (6) a group of the formula:—$S(O)f$-$R^{21}$, wherein f is an integer of 0 to 2, $R^{21}$ represents a hydrogen atom or a hydrocarbon residue which may optionally be substituted, the hydrocarbon residue has the same meaning as defined above, among others, $C_{1-20}$ alkyl especially $C_{1-6}$ alkyl, $C_{6-14}$ aryl, $C_{7-20}$ aralkyl are preferable, and as examples of the substituent to the hydrocarbon residue, mention is made of halogen, nitro, cyano, hydroxy, oxo, thioxo, carboxyl, cyano-$C_{6-14}$ aryl, halogeno-$C_{6-14}$ aryl, etc, (7) an optionally substituted amino group, which is represented by the formula:—$NR^{22}R^{23}$, wherein each of $R^{22}$ and $R^{23}$ independently are hydrogen, $C_{1-6}$ alkyl, $C_{1-6}$ acyl or a 5 to 8 membered heterocyclic group which is mentioned below or a group bonded through nitrogen atom as described above, (8) a group of the formula: —CO—$R^{24}$ wherein $R^{24}$ denotes (i) hydrogen, (ii) hydroxyl, (iii) $C_{1-10}$ alkyl, (iv) $C_{1-6}$ alkoxy which may be substituted with $C_{6-14}$ aryl which may optionally be substituted with halogen or nitro, (v) $C_{3-6}$ cycloalkyl, (vi) $C_{6-14}$ aryl, (vii) $C_{6-14}$ aryloxy, (viii) $C_{7-20}$ aralkyl, (ix) an optionally substituted amino group which is defined (7) above or (x) an optionally substituted 5- to 8-membered heterocyclic group which is mentioned below, especially, $C_{1-10}$ acyl is preferable, (9) a 5- through 8-membered heterocyclic group containing 1–4 hetero-atom (s) selected from oxygen (O), sulfur (S) and nitrogen (N) as ring members, the heterocyclic group being optionally substituted by (i) halogen, (ii) $C_{1-4}$ alkyl, (iii) $C_{1-3}$ alkoxy, (iv) $C_{1-4}$ alkylthio, (v) phenoxy which may optionally be substituted by a halogen, (10) sulfo, (11) $C_{6-14}$ aryl, e.g. phenyl, naphthyl, anthryl, phenanthryl, acenaphthyl, anthracenyl, etc, which may optionally be substituted with one to 4 of (a) hydroxyl, (b) amino, (c) mono- or di-$C_{1-6}$ alkylamino, e.g. methylamino, ethylamino, propylamino, dimethylamino, diethylamino, etc, (d) $C_{1-6}$ alkoxy, e.g. methoxy, ethoxy, propoxy, hexyloxy, etc) or (e) halogen, (12) $C_{3-7}$ cycloalkyl, (13) $Cl_{1-6}$ alkylenedioxy, e.g. methylenedioxy, ethylenedioxy, propylenedioxy, 2,2-dimethylenedioxy, etc, (14) oxo, (15) thioxo, (16) $C_{2-4}$ alkynyl, (17) $C_{3-10}$ cycloalkyl, (18) $C_{2-10}$ alkenyl, e.g. vinyl, allyl, isopropenyl, 1-butenyl, 2-butenyl, butadienyl, hexatrienyl, etc., and among others, $C_{2-6}$ alkenyl is preferable (19) $C_{7-20}$ aralkyl, which has the same meaning as defined above, (20) amidino, and (21) azido.

The above substituents on the hydrocarbon residue may further have substituents. Such substituents includes (1) hydroxy, (2) amino, (3) mono- or di-$C_{1-4}$ alkyl-amino, e.g. methylamino, ethylamino, propylamino, dimethylamino, diethylamino, etc), (4) $C_{1-4}$ alkoxy, e.g. methoxy, ethoxy, propoxy, etc, (5) halogen and (6) nitro. The number of the substituents is preferably 1 to 4, and more preferably 1 to 2.

When the above optionally substituted hydrocarbon residue is cycloalkyl, cycloalkenyl, aryl or aralkyl, each of the group may have one to three of $C_{1-6}$ alkyl, e.g. methyl, ethyl, propyl, isopropyl, butyl, as a substituent. The $C_{1-6}$ alkyl group may further substituted by one to three of hydroxy, oxo, $C_{1-3}$ alkoxy, e.g. methoxy, ethoxy, n-propoxy, isopropoxy, $C_{1-3}$ alkylthio, halogen or carbamoyl.

As examples of the substituted alkyl, mention is made of (1) formyl, i.e. methyl is substituted by oxo, (2) carboxyl, i.e. methyl is substituted by oxo and hydroxy, (3) $C_{1-6}$ alkoxy-carbonyl, i.e. methyl is substituted by oxo and alkoxy, e.g. methoxycarbonyl, ethoxycarbonyl, t-butoxycarbonyl, (4) hydroxy-$C_{1-6}$ alkyl, e.g. hydroxymethyl, hydroxyethyl, hydroxypropyl, hydroxybutyl, (5) $C_{1-3}$ alkoxy-$C_{1-6}$ alkyl, e.g. methoxymethyl, ethoxyethyl, ethoxybutyl, propoxymethyl, propoxyhexyl.

In the above optionally substituted hydrocarbon residue, the number of the substituent(s) is preferably 1 to 6, more preferably 1 to 5, still more preferably 1 to 3 and most preferably 1 to 2. The number of the substituent(s) which is substituted on the substituent is preferably 1 to 3, more preferably 1 or 2.

As the acyl group in the optionally substituted acyl group, mention is made of an acyl group which is derived from $C_{1-24}$ aliphatic carboxylic acid.

Further examples of the acyl group include formyl, $C_{1-6}$ alkyl-carbonyl, e.g. acetyl, ethylcarbonyl, propylcarbonyl, tert-propylcarbonyl, $C_{1-6}$ alkoxy-carbonyl, e.g. methoxycarbonyl, ethoxycarbonyl, t-butoxycarbonyl, $C_{6-14}$ aryl-carbonyl, e.g. benzoyl), $C_{6-14}$, aryloxy-carbonyl, e.g. phenoxycarbonyl, $C_{7-15}$ aralkyl-carbonyl, e.g. benzylcarbonyl), and $C_{7-19}$ aralkyloxy-carbonyl (e.g. benzyloxycarbonyl). Among others, $C_{1-10}$ acyl is preferable. As substituents in the optionally substituted acyl, mention is made of these in the optionally substituted hydrocarbon residue. The substituents on the $C_{1-10}$ acyl group are the same as those on the hydrocarbon residue.

Examples of the optionally substituted carbamoyl group include a carbamoyl group which may optionally be substituted by an optionally substituted $C_{1-20}$ hydrocarbon residue. As an optionally substituted $C_{1-20}$ hydrocarbon residue, mention is made of those described hereinbefore. Concrete examples of the substituted carbamoyl include mono- or di-$C_{1-15}$ alkyl-carbamoyl, e.g. methylcarbamoyl, ethylcarbamoyl, hexylcarbamoyl, dimethylcarbamoyl, methylethylcarbamoyl. The substituents on the carbamoyl group are the same as those on the hydrocarbon residue.

As the heterocyclic group in the optionally substituted heterocyclic group which bonds with the constitutive carbon atom, mention are made of 5 to 8 membered heterocyclic atoms which have one to 4 hetero atoms selected from an oxygen atom, sulfur atom and nitrogen atom than carbon atom; and two ring or three ring condensed-ring heterocyclic groups composed of the above heterocyclic group and other ring groups.

Examples of the heterocyclic groups include (1) 5-membered cyclic groups containing, besides the carbon atom, 1 to 4 hetero-atoms selected from an oxygen atom, sulfur atom and nitrogen atom, such as thienyl, furyl, pyrrolyl, pyrrolinyl, oxazolyl, thiazolyl, pyrazolyl, imidazolyl, imidozolinyl, isoxazolyl, isothiazolyl, 1,2,4-oxadiazolyl, 1,3,4-oxadiazolyl, furazanyl, 1,2,4-thiadiazolyl, 1,2,3-thiadiazolyl, 1,2,5-thiadiazolyl, 1,2,3-triazolyl, 1,2,4-triazolyl, triazinyl, triazolidinyl, and 1H- or 2H-tetrazolyl; (2) 6-membered cyclic groups containing, besides, carbon atom, 1 to 4 hetero-atoms selected from an oxygen atom, sulfur atom and nitrogen atom, as exemplified by pyridyl, pyrimidinyl, thiomorpholinyl, morpholinyl, triazinyl, pyrrolidinyl, piperazinyl, piperidinyl, pyranyl, thiopyranyl, 1,4-oxadinyl, 1,4-thiazinyl, 1,3-thiazinyl, triazinyl, oxotriazinyl, pyridazinyl and pyrazinyl. (3) bicyclic or tricyclic condensed ring groups containing, besides carbon atom, 1 to 4 hetero-atoms selected from oxygen atom, sulfur atom and nitrogen atom, as exemplified by benzofuryl, benzothiazolyl, benzoxazolyl, tetrazolo[1,5-b]pyridazinyl, triazolo[4,5-b]pyridazinyl, benzoimidazolyl, quinolyl, isoquinolyl, cinnolinyl, phthaladinyl, quinazolinyl, quinoxalinyl, indolidinyl, indolyl, quinolidinyl, 1,8-naphthylidinyl, purinyl, pteridinyl, dibenzofuranyl, carbazolyl, acridinyl, phenanthridinyl, chromanyl, benzoxadinyl, phenazinyl, phenothiazinyl and phenoxazinyl.

Examples of the substituents, which the heterocyclic group may have include (1) $C_{1-6}$ alkyl, (2) $C_{2-6}$ alkenyl, (3) $C_{2-6}$ alkynyl, (4) $C_{3-6}$ cycloalkyl, (5) $C_{5-7}$ cycloalkenyl, (6) $C_{7-11}$ aralkyl, (7) C6-14 aryl, (8) $C_{1-6}$ alkoxy, (9) $C_{6-14}$ aryloxy, e.g. phenoxy, (10) $C_{1-6}$ alkanoyl, e.g. formyl, acetyl, propionyl, n-butyryl and isobutyryl, (11) $C_{6-14}$ arylcarbonyl, e.g. benzoyl, (12) $C_{1-6}$ alkanoyloxy, e.g. formyloxy, acetyloxy, propionyloxy, n-butyryloxy and isobutyryloxy, (13) $C_{6-14}$ aryl-carbonyloxy, e.g. benzoyloxy), (14) carboxyl, (15) $C_{1-6}$ alkoxy-carbonyl, e.g. methoxycarbonyl, ethoxycarbonyl, n-propoxycarbonyl, isopropoxycarbonyl, n-butoxycarbonyl, isobutoxycarbonyl and tert-butoxycarbonyl, (16) carbamoyl, (17) N-mono-$C_{1-4}$ alkylcarbamoyl, e.g. N-methylcarbamoyl, N-ethylcarbamoyl, N-propylcarbamoyl, N-isopropylcarbamoyl and N-butylcarbamoyl, (18) N,N-di-$C_{1-14}$ alkylcarbamoyl (e.g. N,N-dimethylcarbamoyl, N,N-diethylcarbamoyl, N,N-dipropylcarbamoyl and N,N-dibutylcarbamoyl), (19) cyclic aminocarbonyl, e.g. 1-aziridinylcarbonyl, 1-azetidinylcarbonyl, 1-pyrrolidinylcarbonyl, 1-piperidinylcarbonyl, N-methylpiperazinylcarbonyl and morpholinocarbonyl, (20) halogen, (21) mono- or tri-halogeno-$C_{1-4}$ alkyl, e.g. chloromethyl, dichloromethyl, trifluoromethyl and trifluoroethyl, (22) oxo, (23) amidino, (24) imino, (25) amino, (26) mono- or di $C_{1-4}$ alkylamino, e.g. methylamino, ethylamino, propylamino, isopropylamino, butylamino, dimethylamino, diethylamino, dipropylamino, diisopropylamino and dibutylamino, (27) 3- to 6-membered cyclic amino group containing, besides the carbon atom and one nitrogen atom, 1 to 3 hetero-atoms selected from oxygen atom, sulfur atom and nitrogen atom, e.g. aziridinyl, azetidinyl, pyrrolidinyl, pyrrolinyl, pyrrolyl, imidazolyl, pyrazolyl, imidazolidinyl, piperidino, morpholino, dihydropyridyl, N-methylpiperazinyl and N-ethylpiperazinyl, (28) $C_{1-6}$ alkanoylamino, e.g. formamido, acetamido, trifluoroacetamido, propionylamido, butyrylamido and isobutyrylamido, (29) benzamido, (30) carbamoylamino, (31) N—$C_{1-4}$ alkylcarbamoylamino, e.g. N-methylcarbamoylamino, N-ethylcarbamoylamino, N-propylcarbamoylamino, N-isopropylcarbamoylamino and N-butylcarbamoylamino, (32) N,N-di-$C_{1-4}$ alkylcarbamoylamino, e.g. N,N-dimethylcarbamoylamino, N,N-diethylcarbamoylamino, N,N- dipropylcarbamoylamino and N,N-dibutylcarbamoylamino, (33) $C_{1-3}$ alkylenedioxy (e.g. methylenedioxy and ethylenedioxy, (34) —B(OH)$_2$, (35) hydroxyl, (36) epoxy (—O—), (37) nitro, (38) cyano, (39) mercapto, (40) sulfo, (41) sulfino, (42) phosphono, (43) dihydroxyboryl, (44) sulfamoyl, (45) $C_{1-6}$ alkylsulfamoyl (e.g. N-methylsulfamoyl, N-ethylsulfamoyl, N-propylsulfamoyl, N-isopropylsulfamoyl and N-butyl sulfamoyl), (46) di-$C_{1-6}$ alkylsulfamoyl, e.g. N,N-dimethylsulfamoyl, N,N-diethylsulfamoyl, N,N-dipropylsulfamoyl and N,N-dibutylsulfamoyl), (47) $C_{1-6}$ alkylthio, e.g. methylthio, ethylthio, propylthio, isopropylthio, n-butylthio, sec-butylthio and tert-butylthio, (48) phenylthio, (49) $C_{1-6}$ alkylsulfinyl, e.g. methylsulfinyl, ethylsulfinyl, propylsulfinyl and butylsulfinyl), (50) phenylsulfinyl, (51) $C_{1-6}$ alkylsulfonyl, e.g. methylsulfonyl, ethylsulfonyl, propylsulfonyl and butylsulfonyl, and (52) phenylsulfonyl. The number of the substituents ranges from 1 to 6, preferably 1 to 3.

Examples of the above-mentioned optionally substituted heterocyclic groups which bond through a carbon atom include 5- to 8-membered cyclic groups or condensed ring thereof containing, besides carbon atom, 1 to 4 hetero-atoms such as oxygen atom, sulfur atom and nitrogen atom. Examples of (1) 5-membered cyclic groups containing, besides carbon atom, 1 to 4 hetero-atoms selected from oxygen atom, sulfur atom and nitrogen atom which bond through a carbon atom include 2- or 3-thienyl, 2- or 3-furyl, 2- or 3-pyrrolyl, 2-, 4- or 5-oxazolyl, 2-, 4- or 5-thiazolyl, 3-, 4- or 5-pyrazolyl, 2- or 3- pyrrolidinyl, 2-, 4- or 5-imidazolyl, 2-imidazolinyl, 2-imidazolidinyl, 3,4- or 5-isoxazolyl, 3-, 4- or 5-isothiazolyl, 3- or 5-(1,2,4-oxadiazolyl), 2-, 5- or 6-(1,3,4-oxadiazolyl), 3- or 5-(1,2,4-thiadiazolyl), 2- or 5-(1,3,4-thiadiazolyl), 4-or 5-(1,2,3-thiadiazolyl), 3- or 4-(1,2,5-thiadiazolyl), 2- or 5-(1,2,3-triazolyl), 3- or 5-(1,2,4-triazolyl), and 5-(1H- or 2H-tetrazolyl). Examples of 6-membered cyclic groups containing, besides, carbon atom, 1 to 4 hetero-atoms selected from oxygen atom, sulfur atom or nitrogen atom which bond through a carbon atom include 2-, 3- or 4-pyridyl, 2-, 4- or 5-pyrimidinyl, 2- or 3-thiomorpholinyl, 2- or 3-morpholinyl, 3- or 6-triazinyl, 2-, 3- or 4-piperidinyl, 2- or 3-piperazinyl, 2- or 3-pyranyl, 2- or 3-thiopyranyl, 2- or 3-(1,4-oxadinyl), 2- or 3-(1,4-thiazinyl), 1- or 4-(1,3-thiazinyl), 3- or 6-triazinyl, 3- or 4-pyridazinyl, 2- or 3-pyrazinyl and 3- or 4-pyridazinyl. Examples of bicyclic or tricyclic condensed ring groups containing, besides carbon atom, 1 to 4 hetero-atoms selected from oxygen atom, sulfur atom and nitrogen atom which bonds through a carbon atom include benzofuryl, benzothiazolyl, benzoxazolyl, tetrazolo[1,5-b]pyridazinyl, triazolo[4,5-b]pyridazinyl, benzoimidazolyl, quinolyl, isoquinolyl, cinnolinyl, phthaladinyl, quinazolinyl, quinoxalinyl, indolidinyl, indolyl, quinolidinyl, 1,8-naphthylidinyl, purinyl, pteridinyl, dibenzofuranyl, carbazolyl, acridinyl, phenathridinyl, chromanyl, benzoxadinyl, phenazinyl, phenothiazinyl and phenoxazinyl. The substituents on the heterocyclic groups which bond through a carbon atom are the same as those on the heterocyclic group above-mentioned.

As examples of the 5 to 7 membered cyclic amino groups containing nitrogen atom, i.e. cyclic amino group or nitrogen atom-containing heterocyclic group, mention is made of pyrrolidinyl, pyrrolinyl, pyrrolyl, pyrazolidinyl, pyrazolinyl, pyrazolyl, imidazolidinyl, imidazolinyl, imidazolyl, 1,2,3-triazinyl, 1,2,3-triazolidinyl, 1,2,3-triazolyl, 1,2,3,4-tetrazolyl, piperidinyl, piperazinyl, azepinyl, hexamethyleneamino, oxazolidino, morpholino, thiazolidino or thiomorpholino. As more preferable cyclic amino groups, mention is made of pyrolidinyl, pyrazolinyl, pyrazolyl, piperidinyl, piperazinyl, morpholino and thiomorpholino.

The cyclic amino groups may be substituted. The examples of the substituents includes (1) $C_{1-6}$ alkyl, (2) $C_{6-14}$ aryl, (3) $C_{7-10}$ aralkyl, (4) benzhydryl, (5) $C_{1-6}$ alkyl-carbonyl, (6) C6-14 aryl-carbonyl, (7) $C_{1-6}$ alkoxy-carbonyl. As the preferable substituent, mention is made of $C_{1-6}$ alkyl, preferably $C_{1-3}$ alkyl.

Examples of the homocyclic group in the optionally substituted homocyclic groups shown by R$^3$ include 3- to 7-membered cyclic hydrocarbon groups consisting of carbon atoms, for example, $C_{6-10}$ aryl, e.g. phenyl, naphthyl; $C_{3-7}$ cycloalkyl, e.g. cyclopropyl, cyclobutyl, cyclopentyl, cyclohexyl and cycloheptyl; and $C_{3-7}$ cycloalkenyl, e.g. cyclopropenyl, cyclobutenyl, cyclopentenyl, cyclohexenyl and cycloheptenyl.

Examples of the substituents which the said homocyclic groups may have, include (1) $C_{1-15}$ alkyl (and among others $C_{1-6}$ alkyl being preferable) which may optionally be substituted by a halogen, (2) $C_{3-10}$ cycloalkyl, (3) $C_{2-10}$ alkenyl, (4) $C_{2-10}$ alkynyl, (5) $C_{3-10}$ cycloalkyl, (6) $C_{6-10}$ aryl, (7) $C_{7-20}$ aralkyl, (8) nitro, (9) hydroxyl, (10) mercapto, (11) oxo, (12) thioxo, (13) cyano, (14) carbamoyl, (15) carboxyl, (16) $C_{1-6}$ alkoxy-carbonyl (e.g. methoxycarbonyl and ethoxycarbonyl), (17) sulfo, (18) halogen, (19) $C_{1-6}$ alkoxy, (20) $C_{6-10}$ aryloxy, e.g. phenoxy, (21) $C_{1-6}$ acyloxy, e.g. acetoxy, propionyloxy, (22) $C_{1-6}$ alkylthio, e.g. methylthio, ethylthio, n-propylthio, isopropylthio, n-butylthio and t-butylthio, (23) $C_{6-10}$ arylthio, e.g. phenylthio), (24) $C_{1-6}$ alkylsulfinyl, e.g. methylsulfinyl and ethylsulfinyl, (25) $C_{6-10}$ arylsulfinyl, e.g. phenylsulfinyl, (26) $C_{1-6}$ alkylsulfonyl, e.g. methylsulfonyl and ethylsulfonyl, (27) $C_{6-10}$ arylsulfonyl, e.g. phenylsulfonyl, (28) amino, (29) $C_{1-6}$ acylamino, e.g. acetylamino and propylamino, (30) mono- or di- $C_{1-4}$ alkylamino, e.g. methylamino, ethylamino, n-propylamino, isopropylamino, n-butylamino, dimethylamino and diethylamino, (31) $C_{3-8}$ cycloalkylamino, e.g. cyclopropylamino, cyclobutylamino, cyclopentylamino and cyclohexylamino, (32) $C_{6-10}$ arylamino, e.g. anilino, (33) $C_{1-6}$ alkanoyl, e.g. formyl, acetyl and hexanoyl), (34) $C_{1-6}$ alkanoyl-oxy, e.g. acetyloxy, propionyloxy, (35) $C_{6-10}$ aryl- carbonyl, e.g. benzoyl, and (36) 5- to 6-membered heterocyclic groups containing, besides carbon atom, 1 to 4 hetero-atoms selected from oxygen, sulfur and nitrogen (e.g. 2- or 3-thienyl, 2- or 3-furyl, 3-, 4- or 5-pyrazolyl, 2-, 4- or 5-thiazolyl, 3-, 4- or 5-isothiazolyl, 2-, 4- or 5-oxazolyl, 3-, 4- or 5-isoxazolyl, 2-, 4- or 5-imidazolyl, 1,2,3- or 1,2,4-triazolyl, 1H or 2H-tetrazolyl, 2-, 3- or 4-pyridyl, 2-, 4- or 5-pyrimidyl, 3- or 4-pyridazinyl, quinolyl, isoquinolyl and indolyl. The number of substituents ranges from 1 to 6, preferably from 1 to 3, more preferably from 1 to 2.

In the compound (I), preferred examples of R$^1$ are a group bonded through a carbon atom or a group bonded through a nitrogen atom. As the group bonded through a carbon atom, mention is made of an optionally substituted $C_{1-20}$ hydrocarbon residue, especially, an optionally substituted $C_{1-10}$ alkyl group or an optionally substituted $C_{1-6}$ alkyl group. As substituents in the optionally substituted $C_{1-20}$ hydrocarbon residue of R$^1$, mention is made of (1) halogen, (2) nitro, (3) cyano, (4) an optionally substituted amino, (5) an optionally substituted hydroxyl group, (6) a group of the formula: —S(O)t-R$^6$ (wherein t denotes an integer of 0 to 2, and R$^6$ is a hydrogen atom or an optionally substituted hydrocarbon residue.)

A more preferable example of R$^1$ is substituted aminoalkyl such as N,N-disubstituted aminoalkyl. The most preferable example of $R_1$ is N-aralkyl-N-alkylaminoalkyl, especially N—$C_{7-11}$ aralkyl-N—$C_{1-6}$ alkylamino-$C_{1-6}$ alkyl.

As the preferable example of $R^2$, mention is made of a group bonded through a carbon atom, especially an optionally substituted $C_{1-20}$ hydrocarbon residue, more especially an optionally substituted $C_{6-14}$ aryl group. As the preferable examples of the substituents, mention is made of (1) an optionally substituted amino, (2) an optionally substituted hydroxyl group, (3) an optionally substituted carbamoyl, (4) an optionally substituted carboxyl, (5) an optionally substituted alkenyl, (5) acyl or (6) nitro.

The preferable substituents in the optionally substituted aryl, include (1) an alkoxy group, (2) an alkylcarbonyl group, (3) an alkylaminocarbonyl group, (4) an optionally substituted alkenyl, whose preferable substituent includes alkylcarbonyl or alkylaminocarbonyl, or (5) an optionally substituted amino, whose preferable substituent includes an alkyl group or an alkyl group which is substituted by alkanoyl, alkanoyl or hydroxy. Especially, an alkanoylamino group or an alkoxy group is more preferable.

As the preferable group of $R^2$, mention is made of a $C_{6-14}$ aryl group which may optionally be substituted with a group selected from the group consisting of (i) nitro, (ii) $C_{1-6}$ alkoxy and (iii) amino which may optionally be substituted $C_{1-6}$ alkanoyl.

As the preferable example of $R^3$, mention is made of an optionally substituted homo-cyclic group, more preferably, an optionally substituted $C_{6-14}$ aryl group.

The substituents in the optionally substituted homo-cyclic group, mention is made of (1) halogen, (2) nitro, (3) an optionally substituted hydroxyl group, (4) a group of the formula: —S(O)t-$R^6$ (wherein t denotes an integer of 0 to 2, and $R^6$ is a hydrogen atom or an optionally substituted hydrocarbon residue).

As more preferable group of $R^3$, mention is made of an aryl group substituted by one or two halogens. As the aryl group, phenyl is most preferable. The most preferable group of $R^3$ is a phenyl group substituted by fluorine.

As the preferable example of the heterocyclic group in the optionally substituted heterocyclic group of $R^4$, mention is made of an optionally substituted 3- to 8-membered heterocyclic group, especially an optionally substituted 5- to 8-membered heterocyclic group having at a least one nitrogen atom in a ring, and more preferably 5- to 6-membered heterocyclic group having at least one nitrogen atom in a ring. As the preferred examples of the heterocyclic ring, mention is made of oxazolyl, isoxazolyl, thiazolyl, imidazolyl, triazolyl, oxoimidazolyl, thiazinyl. Among others, isoxazoly is most preferred.

Preferred examples of the substituent to the heterocyclic group are (1) halogen, (2) nitro, (3) an optionally substituted hydroxyl group, (4) a group of the formula: —S(O)m-$R^6$ (wherein m denotes an integer of 0 to 2, and $R^6$ is a hydrogen atom or an optionally substituted hydrocarbon residue), (5) an optionally substituted amino, or (6) a $C_{1-10}$ hydrocarbon residue.

Preferred examples of the substituents on the optionally substituted amino group, the optionally substituted hydroxyl group or the optionally substituted mercapto group of $R^4$ are (1) $C_1$ hydrocarbon residue which may optionally be substituted by $C_{1-6}$ alkoxy-carbonyl or carbamoyl, (2) $C_{1-10}$ acyl group, or (3) a group of the formula: —S(O)$_t$—$R^6$, wherein t denotes an integer of 0 to 2, and $R^6$ is a hydrogen atom or an optionally substituted hydrocarbon residue.

Preferably $R^4$ is (1) a 5- or 6-membered heterocyclic group which has one nitrogen atom and one oxygen atom and which is bonded through a carbon atom, (2) a hydroxyl group which may optionally be substituted with a group selected from the group consisting of (i) $C_{1-6}$ alkyl which may optionally be substituted with $C_{1-6}$ alkoxycarbonyl or carbamoyl, (ii) $C_{1-6}$ alkanoyl and (iii) $C_{1-6}$ alkylsulfonyl, (3) a group of the formula: —S(O)$_t$—$R^{6'}$, wherein t is an integer of 0 to 2 and $R^{6'}$ is $C_{1-6}$ alkyl, or (4) an amino group which may optionally be substituted with $C_{1-6}$ alkanoyl.

As the group $R^5$, a hydrogen atom or a hydrocarbon residue is preferable, especially, a hydrogen atom or $C_{1-20}$ hydrocarbon atom is more preferable. Among others, hydrogen atom or $C_{1-10}$ alkyl is more preferable. Hydrogen atom is most preferable.

In the formula (I), n is preferably 1.

In the above definitions, as the examples of halogen, mention is made of fluorine, chlorine, bromine, iodine.

As examples of $C_{1-6}$ alkyl, mention is made of methyl, ethyl, n-propyl, isopropyl, n-butyl, isobutyl, s-butyl, t-butyl, pentyl, isopentyl, neopentyl, hexyl.

$C_{1-4}$ alkyl is exemplified by methyl, ethyl, n-propyl, isopropyl, n-butyl, isobutyl, t-butyl. $C_{1-3}$ alkyl is exemplified by methyl, ethyl, n-propyl, isopropyl.

As examples of $C_{2-10}$ alkenyl, mention is made of vinyl, allyl, 2-methylallyl, isopropenyl, 2-butenyl, 3-butenyl, butadienyl, hexatrienyl, 3-octenyl. Examples of $C_{2-6}$ alkenyl are vinyl, allyl, isopropnyl, butenyl and hexatrienyl. Examples of $C_{2-4}$ alkenyl are vinyl, allyl, isopropenyl and butenyl.

As example of the $C_{2-10}$ alkynyl, mention is made of ethynyl, 1-propynyl, 2-propynyl, propargyl, and 3-hexynyl. $C_{2-6}$ alkynyl and $C_{2-4}$ alkynyl is exemplified by ethynyl, 1-propynyl, 2-propynyl.

$C_{3-10}$ cycloalkyl is exemplified by cyclopropyl, cyclobutyl, cyclopentyl, cyclohexyl, cycloheptyl, cyclooctyl, cyclononyl. $C_{3-8}$ cycloalkyl is exemplified by cyclopropyl, cyclobutyl, cyclopentyl, cyclohexyl, cycloheptyl, cyclooctyl. $C_{3-7}$ cycloalkyl is exemplified by cyclopropyl, cyclobutyl, cyclopentyl, cyclohexyl, cycloheptyl. $C_{3-6}$ cycloalkyl is exemplified by cyclopropyl, cyclobutyl, cyclopentyl, cyclohexyl.

Examples of $C_{3-7}$ cycloalkenyl are cyclopropenyl, cyclobutenyl, cyclopentenyl, cyclohexenyl, and examples of $C_{5-7}$ cycloalkenyl are cyclopentenyl, cyclohexenyl.

$C_{6-14}$ aryl is exemplified by phenyl, naphthyl, anthryl, phenanthryl, acenaphthyl, anthracenyl. Examples of $C_{6-10}$ aryl are phenyl and naphthyl. Especially phenyl is most preferable.

$C_{7-20}$ aralkyl is exemplified by benzyl and phenethyl, benzhydryl, trithyl. $C_{7-15}$ aralkyl and $C_{7-13}$ aralkyl are benzyl, phenethyl, benzhydryl. Examples of $C_{7-11}$ aralkyl and $C_{7-10}$ aralkyl are benzyl, α-methylkenyl and phenethyl.

$C_{1-6}$ alkoxy is exemplified by methoxy, ethoxy, propoxy, isopropoxy, n-butoxy, isobutoxy, s-butoxy, t-butoxy, pentyloxy, isopentyloxy, neopentyloxy, hexyloxy, $C_{1-4}$ alkoxy is exemplified by methoxy, ethoxy, propoxy, isopropoxy, n-butoxy, isobutoxy, s-butoxy, t-butoxy. $C_{1-3}$ alkoxy is exemplified by methoxy, ethoxy, propoxy, isopropoxy.

$C_{1-6}$ acyl is exemplified by a $C_{1-6}$ alkanoyl group of the formula: —CO—$R^{25}$, wherein $R^{25}$ is hydrogen, methyl, ethyl, propyl, isopropyl, n-butyl, isobutyl, s-butyl, t-butyl, pentyl.

$C_{1-4}$ acyl is exemplified by a $C_{1-4}$ alkanoyl group of the formula: —CO—$R^{25'}$, wherein $R^{25'}$ is hydrogen, methyl, ethyl, propyl, isopropyl.

Preferable five to seven-membered heterocyclic groups which contain 1 to 4 heteroatoms of oxygen, sulfur or nitrogen are exemplified by thienyl, furyl, pyrrolyl, pyrazolyl, thiazolyl, isothiazolyl, oxazolyl, isoxazolyl, imidazolyl, triazolyl, tetrazolyl, furazanyl, tetrahydrofuryl, pyridyl, pyrimidinyl, pyridazynyl, oxadiazolyl, tetrahydropyranyl, morpholinyl, thiomorpholinyl, pyrrolidinyl, pyrrolinyl, pyrazolidinyl, pyrazolinyl, imidazolidinyl, imidazolinyl, imidazolyl, 1,2,3-triazinyl, 1,2,3-triazolidinyl, 1,2,3-triazolyl, 1,2,3,4-tetrazolyl, piperidinyl, piperazinyl, hexamethyleneaminyl, oxazolidinyl or thiazolidinyl. As more preferable heterocyclic groups, mention is made of 5 to 6 membered heterocyclic groups. In particular, pyrrolidinyl, pyrazolinyl, pyrazolyl, piperidinyl, piperazinyl, morpholinyl and thiomorpholinyl are preferable.

Examples of optionally substituted aromatic hydrocarbon or heterocyclic residues optionally containing a hetero-atom, which are represented by A and B, include aromatic hydrocarbon residues such as phenyl, and 4- to 7-membered monocyclic or condensed heterocyclic residues containing one or more of N, S and O, for example, pyridyl, pyrimidinyl, pyridazinyl, pyrazinyl, thienyl, furyl, pyrrolyl, imidazolyl, pyrazolyl, isothiazolyl, isooxazolyl, benzofuranyl, isobenzofuranyl, indolizinyl, isoindolyl, 3H-indolyl, indolyl, 1H-indazolyl, purinyl, 4H-quinolizinyl, isoquinolyl, quinolyl, phthalazinyl, naphthyridinyl, quinoxalinyl, quinazolinyl, cinnolinyl and pteridinyl (preferably phenyl). As the spacer, any one can be exemplified, so long as it is a divalent chain in which the number of atoms constituting the straight chain is 1 or 2, and it may have a side chain, more specifically, lower (1-4C) alkylene, —CO—, —O—, —S—, —NH—, —CO—NH—, —O—CH$_2$—, —S—CH$_2$—, and —CH=CH—.

R$^7$ is an optionally substituted 5-7 membered heterocyclic residue having, as a group capable of constituting the ring, carbonyl group, thiocarbonyl group, an optionally oxidized sulfur atom or a group convertible into them. Examples of the group R$^7$ are 2,5-dihydro-5-oxo-1,2,4-oxadiazol-3-yl, 2,5-dihydro-5-thioxy-1,2,4-oxadiazol-3-yl, 2,5-dihydro-5-oxo-1,2,4-thiadiazol-3-yl. (As to the R$^7$, D, A ring, B ring, refer European Patent Application Publication No. 520423A).

The compound of the following formula:

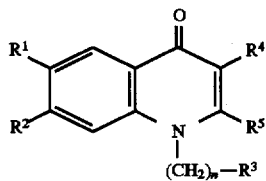

wherein R$^1$, R$^2$, R$^3$, R$^4$, R$^5$ and n have the same meaning defined as above, can be produced by per se known methods, have a similar activity and can be used in a similar way.

The present compound (I), and its salts can be produced easily by per se known methods, as exemplified by the following production methods. Production Method 1:

Production of the nucleus of the present compound:

In accordance with the method disclosed by K. Gewald, E. Schinke and H. Bøttcher, Chem. Ber., 99, 94–100 (1966), and as illustrated in Scheme 1, infra, an adequate ketone or aldehyde having an active methylene (i) was allowed to react with a cyanoacetic acid ester derivative and sulfur to convert it into a 2-aminothiophene derivative (ii). More specifically, in the case of using ketone (R$^{1'}$≠H), it is subjected to heating under reflux together with a cyanoacetic acid ester derivative, in the presence of acetic acid and ammonium acetate, in a proper solvent such as toluene to give an alkylidene cyanoacetic acid ester derivative, which is then heated in an adequate solvent, for example, ethanol in the presence of sulfur and a base to afford a 2-aminothiophene derivative (ii). And, in the case of using aldehyde (R$^{1'}$=H), it is heated in a proper solvent, for example, dimethylformamide, in the presence of a cyanoacetic acid ester derivative, sulfur and a base to give a 2-aminothiophene derivative (ii). The compound (ii) thus obtained is heated, in accordance with the method disclosed by Kuwata et al. [cf. German Patent 2,435,025], with diethyl ethoxymethylenemalonate to give an adduct (iii). The adduct is stirred in an appropriate solvent, i.e. one which does not adversely affect the reaction, e.g. alcohols such as ethanol and methanol, in the presence of a base, e.g. alkali metal hydroxide such as potassium hydroxide and sodium hydroxide, at temperatures ranging from about 10° to 70° C. to give thiophene carboxylic acid derivative (iv). Then, the thiophene carboxylic acid derivative (iv) thus obtained is subjected to ring-closure by heating in polyphosphoric acid ester (PPE) to give a thieno[2,3-b]pyridine derivative (v). The compound (v) is stirred in an appropriate solvent, e.g. amides such as dimethylformamide and dimethylacetamide), in the presence of a compound of the formula: Xa—(CH$_2$)n-R$^3$, wherein Xa is a halogen atom, n and R$^3$ have the same meaning as defined above, and a base, e.g. an organic base such as pyridine and triethylamine) at temperatures ranging from about 10° to 100° C. to give a 4,7-dihydro-4-oxothieno[2,3-b]pyridine-5-carboxylic acid ester derivative shown by the formula (vi).

The foregoing production method is shown in Scheme 1. In the Scheme 1, R$^{1''}$ denotes C$_{1-6}$ alkyl or a hydrogen atom, R' denotes C$_{1-6}$ alkyl, Xa denotes a halogen atom, and Et denotes ethyl. The groups R$^2$, R$^3$, R$^5$ and n have the same meaning as defined above. As the examples of halogen of Xa, mention is made of fluorine, bromine, chlorine, iodine.

Scheme 1:

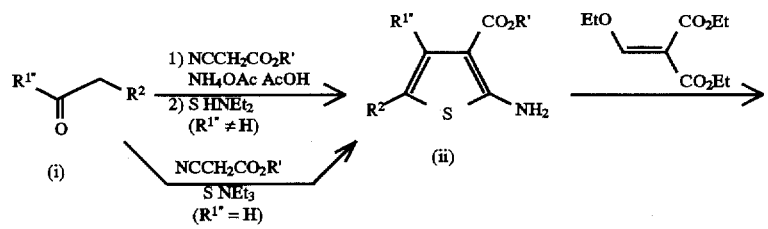

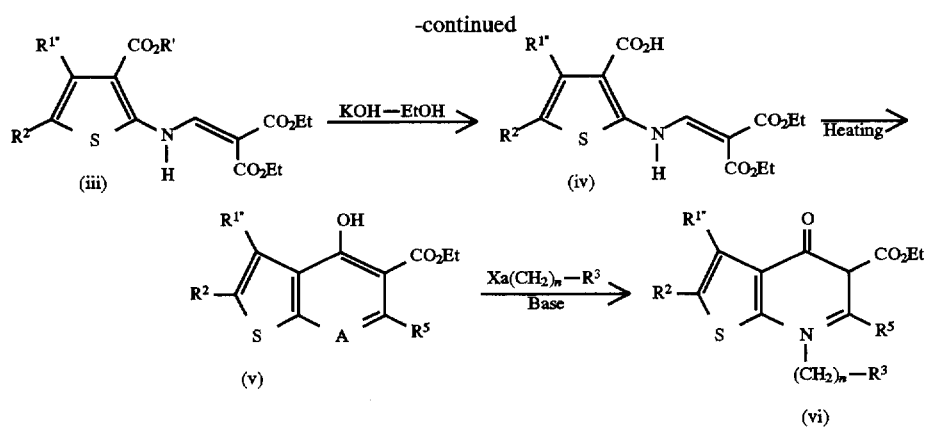

Production Method 2

In substantially the same manner as in the Production Method 1, and as illustrated in Scheme 2, infra, a 2-aminothiophene derivative whose 5-position is unsubstituted (vii), which can be synthesized by the method disclosed by Karl Gewald, Chem. Ber., 98, 3571–3577 (1965); K. Gewald and E. Schinke, Chem. Ber., 99, 2712–2715 (1966) is allowed to react with diethyl ethoxymethylene malonate under heating, in accordance with the method disclosed by Kuwata et al., German Patent 2,435,025, to give an adduct (viii). The adduct is stirred at temperatures ranging from about 10° to 60° C. in an appropriate solvent, e.g. alcohols such as ethanol and methanol, in the presence of a suitable base, e.g. alkali metal hydroxide such as potassium hydroxide and sodium hydroxide, to give thiophene carboxylic acid derivative (ix). To the compound (ix) the group $R^{2''}$ is introduced to give a compound (x). As the reaction of the introduction of $R^{2''}$, mention is made of, for example, nitration using fuming nitric acid-concentrated sulfuric acid or sodium nitrate-concentrated sulfuric acid, acylation using acid chloride-aluminum chloride, formylation using phosphorus oxychloride-dimethylformamide or N-methylformanilide and halogenation using N-bromosuccinimide or bromine-pyridine. Then the compound (x) is subjected to ring-closure reaction under heating in polyphosphoric acid ester (PPE) to give a thieno[2,3-b]pyridine derivative (xi). The compound (xi) is subjected to the similar reaction of the compound (v) to the compound (vi) to give a compound (xii) wherein $R^{2''}$ is nitro group, an acyl group, a formyl group or halogen.

The foregoing method is shown in Scheme 2. In the Scheme 2, $R^{2''}$ denotes nitro group, acyl group, formyl group or halogen, and other groups have the same meaning as defined above.

Scheme 2:

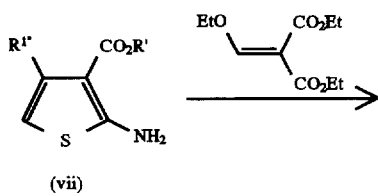

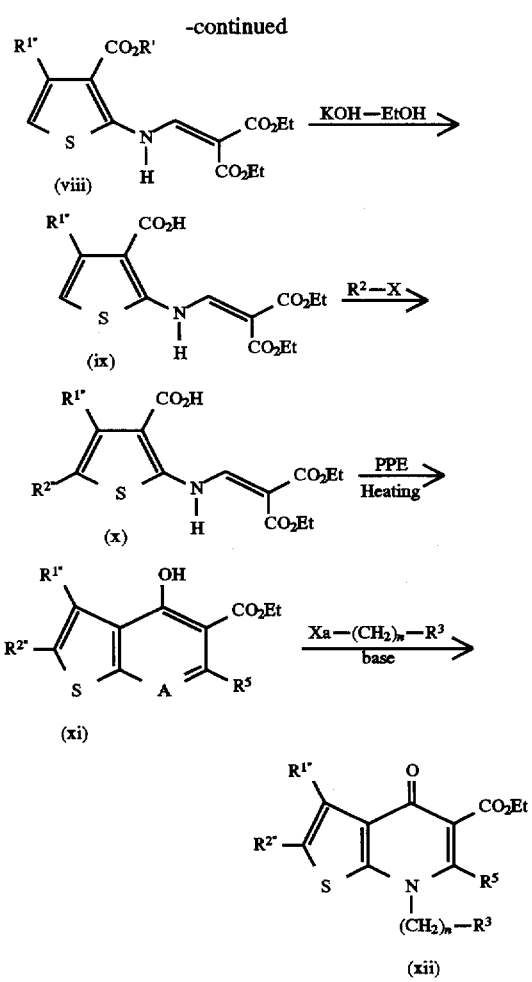

Production Method 3

Production of a compound having formyl at 5-position:

As illustrated in Scheme 3, infra, in an appropriate solvent, e.g. ethers such as tetrahydrofuran, ethyl ether and dioxane, 4,7-dihydro-4-oxothieno[2,3-b]pyridine-5-carboxylic acid ester derivative (v) is stirred together with a suitable reducing agent, e.g. lithium aluminum hydride, at a temperature ranging from about 0° to 80° C. to give a reduced compound (xiii).

The compound (xiii) is reacted with a compound of the formula: $Xa—(CH_2)n-R^3$, wherein Xa denotes a halogen atom, and n and $R^3$ have the same meaning as defined above, in an appropriate solvent, e.g. dimethylformamide, dimethylacetamide, at a temperature ranging from 10° C. to 100° C. under stirring to give 4,7-dihydro-4-oxothieno[2,3-b]pyridine derivative shown by the formula (xiv). The said derivative is stirred, together with a suitable oxidizing agent, e.g. manganese dioxide, in a proper solvent, e.g. dichloromethane or chloroform, at temperatures ranging from about 10° to 80° C. to give a 5-formyl derivative (xv).

The foregoing method is shown in Scheme 3. In the Scheme 3, the groups $R^{1''}$, Xa, $R^2$, $R^3$, $R^5$ and n have the same meaning defined above.

Scheme 3

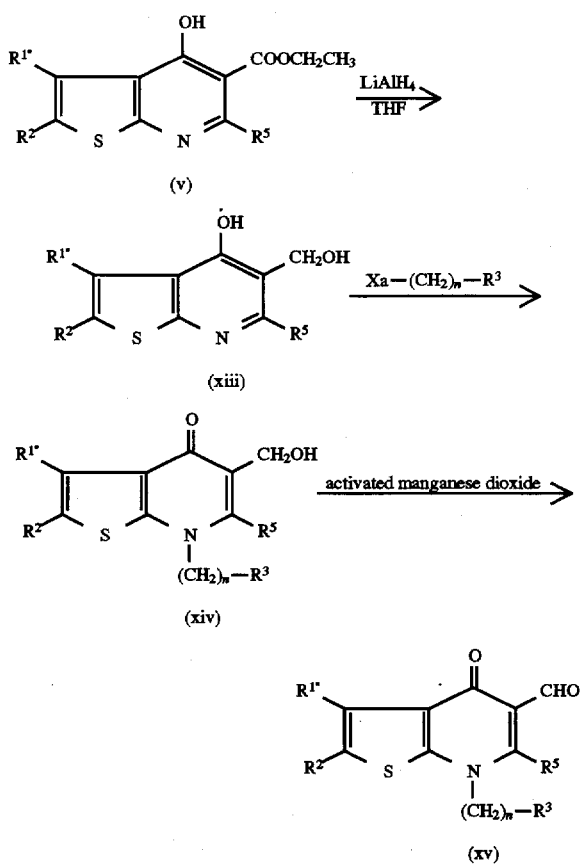

Scheme 4:

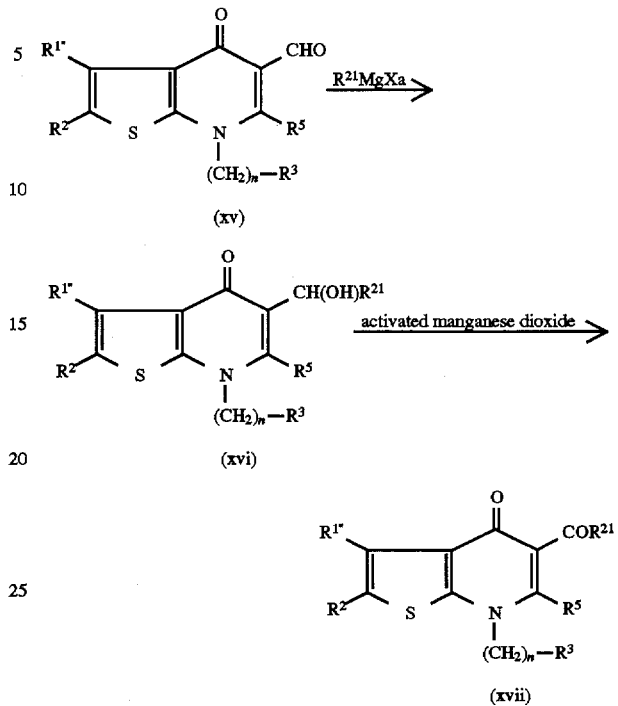

Production Method 4

Production of 5-carbonyl derivative from 5-formyl derivative is illustrated in Scheme 4, infra:

The 5-formyl derivative (xv) is stirred, together with a Grignard's reagent of the formula: $R^{21}MgXa$, wherein $R^{21}$ denotes $C_{1-6}$ alkyl and Xa denotes a halogen atom, at a temperature ranging from about 0° to 80° C. in an appropriate solvent, e.g. ethers such as tetrahydrofuran and ethyl ether, to give a corresponding secondary alcohol derivative (xvi). The compound (xvi) is stirred, together with a suitable oxidizing agent, e.g. metal oxide such as manganese dioxide, in a proper solvent, e.g. halogenated hydrocarbons such as dichloromethane and chloroform, at a temperature ranging from about 10° to 80° C. to give a 5-carbonyl derivative (xvii). The foregoing production method 4 is shown in Scheme 4:

In the Scheme 4, $R^{21}$ denotes $C_{6-14}$ aryl group, $C_{1-6}$ alkyl group or an optionally substituted $C_{1-6}$ alkyl group, and other groups have the same meaning defined above.

Production Method 5

Production of 5-keto derivatives:

As illustrated in Scheme 5, infra, 4,7-Dihydro-4-oxothieno[2,3-b]pyridine-5-carboxylic acid ester derivative (xviii), which is produced by subjecting the compound (vi) or (xii) to ester oxchange reaction, is stirred at temperatures ranging from about 10° to 100° C., together with an aluminum amide derivative previously produced from a proper aluminum reagent, e.g. trimethyl aluminum and diisobutyl aluminum hydride (DIBAL) and amine in an appropriate suitable solvent, e.g. halogenated hydrocarbons such as dichloromethane and ethers such as tetrahydrofuran, ethyl ether and dioxane, to give a 4,7-dihydro-4-oxothieno[2,3-b] pyridine-5-carboxylic acid amide derivative (xix). The derivative (xix) is stirred, together with a Grignard's reagent, in an appropriate solvent, e.g. tetrahydrofuran and ethyl ether, at a temperature ranging from about –78° C. to 80° C. to give a corresponding ketone derivative (xx). The foregoing production method 5 is shown in Scheme 5:

In Scheme 5, $R^{22}$ denotes $C_{1-6}$ alkyl or $C_{6-14}$ aryl, $R^{23}$ and $R^{24}$ respectively denotes a hydrogen atom or a group bonded through a carbon atom. $R^{25}$ denotes a group bonded through a carbon atom. Other group have the same meaning as defined above.

Scheme 5:

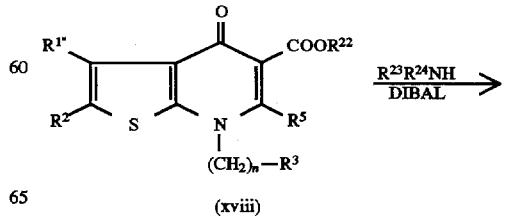

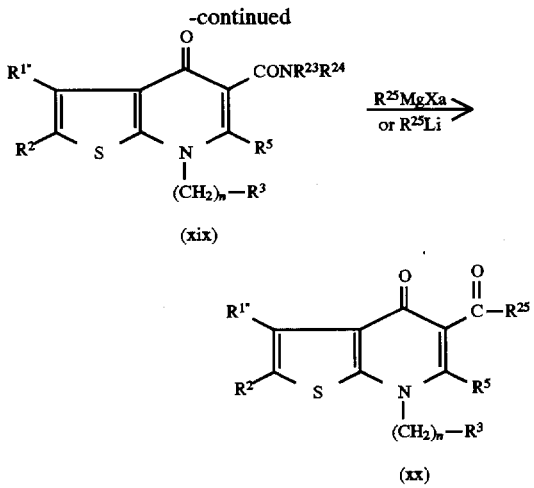

Production Method 6

Production of a compound wherein it has an aryl group at 2-position is illustrated in Scheme 6, infra:

The compound (xxi), whose 2-position is halogen and which is produced by a similar manner in said Production Method 2, or which is produced by halogenating a compound wherein it has a hydrogen atom at its 2-position with N-bromosuccinimide or bromine-pyridine, is dissolved in an appropriate solvent, e.g. ethers such as 1,2-dimethoxyethane, tetrahydrofuran, dioxane; alcohols such as ethylalcohol. To the solution is added aryl boric acid derivative, e.g. phenyl boric acid, 3-methoxyphenyl boric acid, 4-ethoxycarbonylphenyl boric acid. Further, to the mixture are added a catalyst, e.g. palladium metal such as tetrakis (triphenylphosphine)palladium, in the presence of an inert gas, e.g. argon gas. The mixture is stirred at about 10° C. to 100° C. for a few minutes to several hours. After removing the insolubles, the desired compound (Ia) is obtained.

The foregoing production method is shown in Scheme 6. In Scheme 6, X" denotes halogen, $R^{31}$ denotes an optionally substituted $C_{6-14}$ aryl, and other groups have the same meanings defined as above.

Scheme 6:

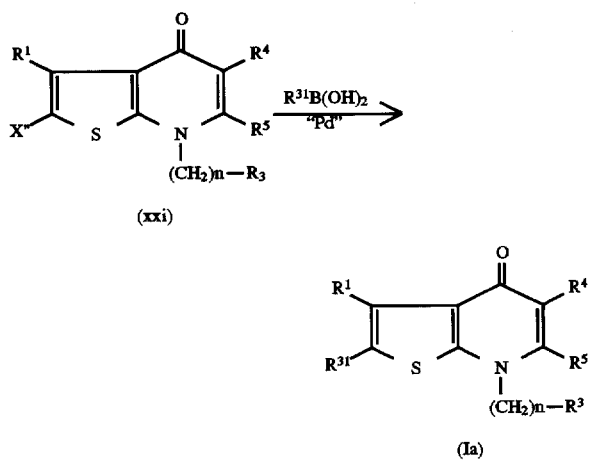

Production Method 7

Production of a derivative which has 2,5-dioxo-4-imidazolidinyl at 5-position is illustrated in Scheme 7, infra:

The formyl derivative (xv), which is obtained in the above Production Method 3 or its similar method, is reacted with a sodium bisulfite in an appropriate solvent, e.g. water, ethanol. The reaction is carried out at 0° C. to 80° C. under stirring to give a sulfuric acid additive (xxii).

To the additive (xxii) is added a cyano compound, e.g. potassium cyanide, sodium cyanide, in an appropriate solvent, e.g. aqueous ethanol, aqueous tetrahydrofuran, dioxane, in the presence of an equivalent to an excess amount of a base, e.g. ammonium carbonate. The reaction is carried out at 0° C. to 80° C. under stirring, and under refluxing when required, to give an imidazolidinyl derivative (Ib).

The foregoing method is shown in Scheme 7. In Scheme 7, all the groups have the same meaning as defined above.

Scheme 7:

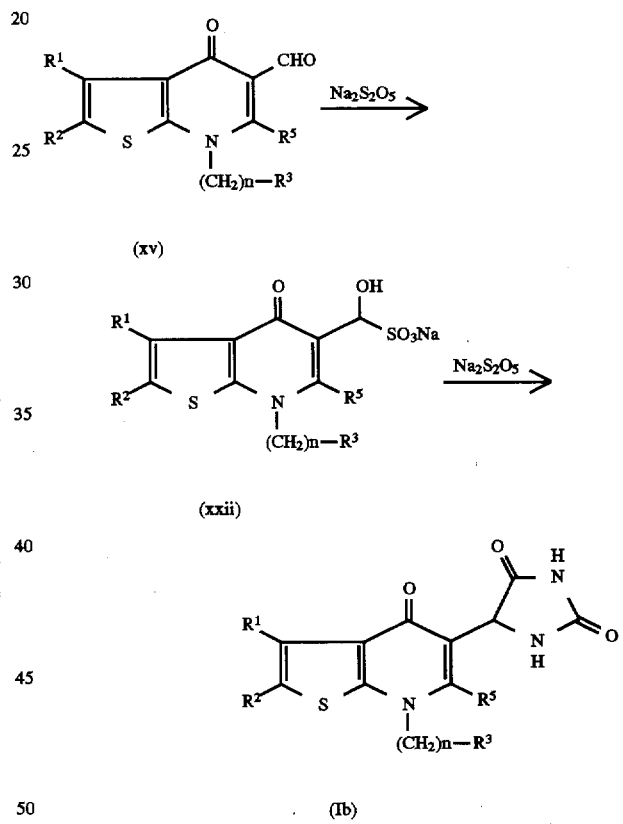

Production Method 8

Production of a compound which has an oxazolyl group at 5-position is illustrated in Scheme 8, infra:

The derivative (xv), which has a formyl group at 5-position, is reacted with an equivalent to excess amount of tosylmethylisoniazide in an appropriate solvent, e.g. methanol, ethanol, in the presence of an equivalent to an excess amount of a base, e.g. potassium carbonate. The reaction is carried out at 0° C. to 80° C. under stirring, and under refluxing when required, to give a derivative (Ic) which has an oxazolyl group at 5-position.

The foregoing production method is shown in Scheme 8. In scheme 8, other groups have the same meaning as defined above.

Scheme 8:

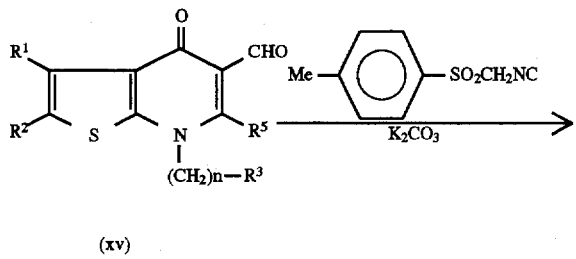

(xv)

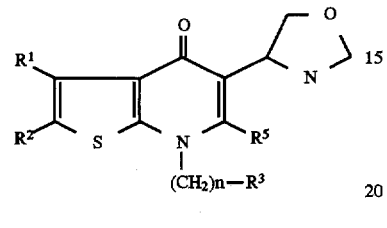

(Ic)

Scheme 9:

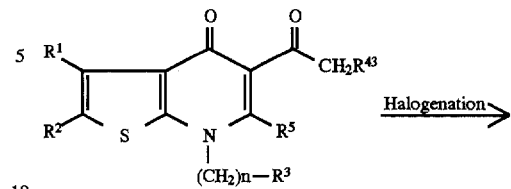

(xxiv)

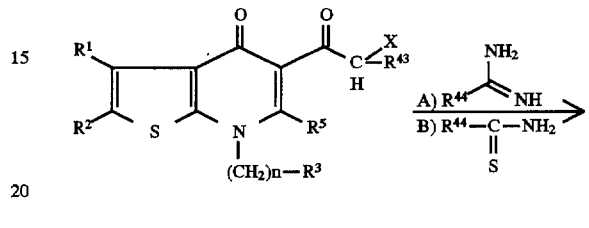

(xxv)

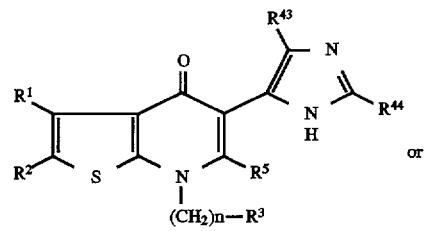

A. (Id)

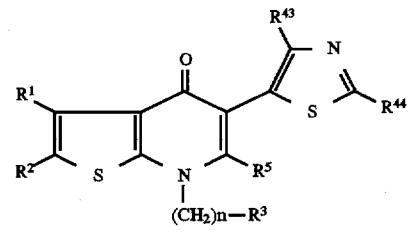

B. (Ie)

Production Method 9

Production of a compound having 4-imidazolyl group or 4-thiazolyl group at 5-position is illustrated in Scheme 9, infra:

4,7-Dihydro-5-acyl-4-oxothieno[2,3-b]pyridine derivative (xxiv), obtained in said Production Method 4 or 5, is dissolved in an appropriate solvent, e.g. acetic acid, methanol, tetrahydrofuran, ethylether, dioxane.

To the solution an equivalent to a small excess of halogenating agent, e.g. bromine or iodine, is added dropwise under a room temperature or ice-cooling. The mixture is stirred at a temperature of 0° C. to 80° C. to give an α-haloketon derivative (xxv).

Said α-haloketon derivative (xxv) is dissolved in an appropriate solvent, e.g. methanol, tetrahydrofuran, ethylether, dioxane, dimethylformamide. To the solution is added an equivalent to a small excess amount of amidine derivative under room temperature or ice-cooling. The mixture is stirred at a temperature of 0° C. to 80° C., and the system is heated if required, to give a 4-imidazolyl derivative (Id).

The α-haloketone derivative (xxv) is reacted with a thiocarbamoyl derivative in an appropriate solvent, e.g. methanol, ethanol, dimethylformamide, dimethylacetamide, at a temperature of about 10° C. to 100° C. under stirring to give a 4-thiazolyl derivative (Ie).

Similar to the above, the α-haloketone derivative is reacted with a thioglycolic acid amide, and then subjected to a ring-closure reaction to give a 1,4-thiazinyl derivative.

The foregoing method of the production of imidazolyl derivative and thiazolyl derivative is shown in Scheme 9. In Scheme 9, $R^{43}$ denotes hydrogen atom, $C_{1-6}$ alkyl or $C_{6-14}$ aryl. $R^{44}$ denotes hydrogen atom, $C_{1-6}$ alkyl or $C_{6-14}$ aryl. $R^1$, $R^2$, $R^3$, $R^5$ and n have the same meaning as defined above.

Production Method 10

Production of a compound having 2-oxazolyl group at 5-position is illustrated in Scheme 10, infra:

4,7-Dihydro-5-carbamoyl-4-oxothieno[2,3-6]pyridine derivative (xvi), obtained by the first step in the above Production Method 5, is dissolved in an appropriate solvent, e.g. methanol, ethanol, tetrahydrofuran, dioxane, and to the solution is added an equivalent to a small excess of α-haloketone compound dropwise under room temperature or ice-cooling. The mixture is stirred at 0° C. to 80° C., and refluxed under heating if required, to give a 2-oxazolyl derivative (If).

The foregoing method is shown in Scheme 10. In Scheme 10, $R^{45}$ denotes hydrogen atom, $C_{1-6}$ alkyl or $C_{6-14}$ aryl. Xa denotes a halogen atom and $R^1$, $R^2$, $R^3$, $R^5$ and n have the same meaning as defined above.

Scheme 10:

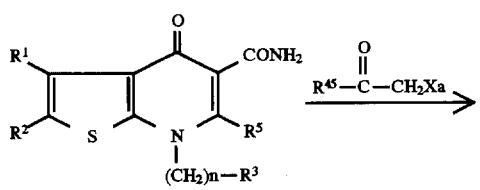

(xvi)

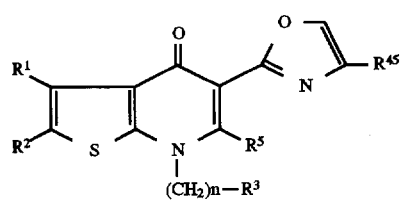

(If)

Production Method 11

Production of a compound having 2-thiazolyl at 5-position is illustrated in Scheme 11, infra:

To a solution of 4,7-Dihydro-5-carbamoyl-4-oxothieno[2,3-b]pyridine derivative (xxvi) in an appropriate solvent, e.g. toluene, tetrahydrofuran, dioxane, an equivalent amount or a small excess amount of thioamide reagent, e.g. Lawessons reagent, is added under room temperature or ice-cooling. The mixture is stirred at a temperature of 0° C. to 80° C., and subjected to refluxing under heating if required, to give a 4,7-dihydro-5-thiocarbamoyl-4-oxothieno[2,3-b]pyridine derivative (xxvii).

Said thiocarbamoyl derivative (xxviii) is dissolved in an appropriate solvent, e.g. methanol, ethanol, tetrahydrofuran, dioxane, and to the solution is added dropwise an equivalent amount to a small excess amount of α-haloketone compound under room temperature or ice-cooling. The mixture is stirred at a temperature of about 0° C. to 80° C., and is subjected to refluxing under heating, to give 2-thiazoly derivative (Ig).

The foregoing method is shown in Scheme 11. In Scheme 11, $R^{46}$ denotes hydrogen $C_{1-6}$ alkyl or $C_{6-14}$ aryl. Xa denotes a halogen atom. $R^1, R^2, R^3, R^5$ and n have the same meaning as defined above.

Scheme 11:

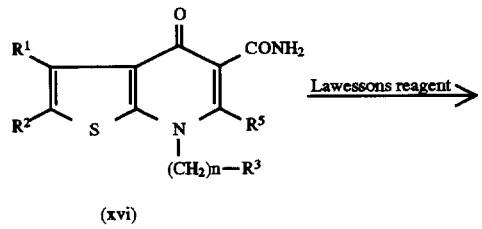

(xvi)

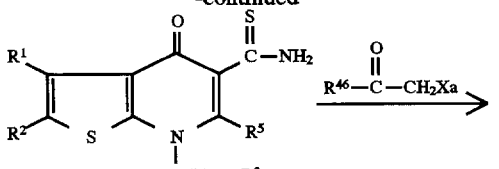

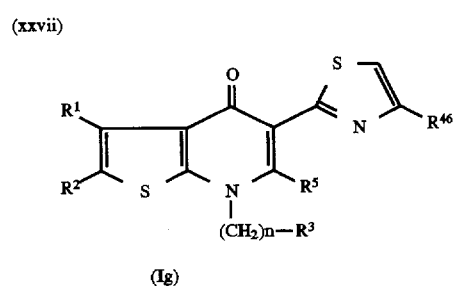

(xxvii)

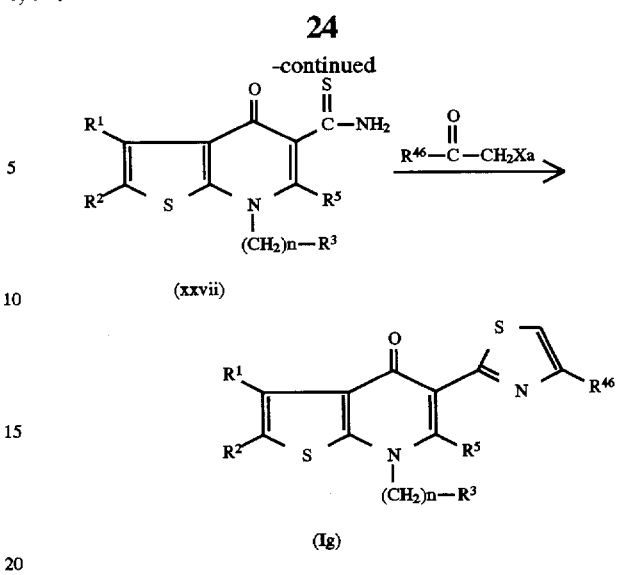

(Ig)

Production Method 12

Production of a compound having 3-pyrazolyl group at 5-position is illustrated in Scheme 12, infra:

To a solution of 4,7-dihydro-5-acetyl-4-oxothieno[2,3-b]pyrimidine (xxviii), obtained by the method of Production Method 5, in an appropriate solvent, e.g. methanol, ethanol, tetrahydrofuran, dioxane is added dropwise an excess amount of formyl ethyl ester and a base, e.g. sodium ethoxide, under room temperature or under ice-cooling. The mixture is stirred at a temperature of 0° C. to 80° C. to give an α-formylketone derivative (xxx).

The α-formylketone derivative (xxx) is dissolved in an appropriate solvent, e.g. water, methanol, tetrahydrofuran, dioxano, dimethylformamide. To the solution is added an equivalent to a small excess of hydrazine derivative or its salt under room temperature or ice-cooling. The mixture is stirred at a temperature of about 0° C. to 80° C., and subjected to refluxing under heating if required, to give a 3-pyrazolyl derivative (Ih).

The foregoing method is shown in Scheme 12. In Scheme 12, $R^1, R^2, R^3, R^5$ and n have the same meaning as defined above.

Scheme 12:

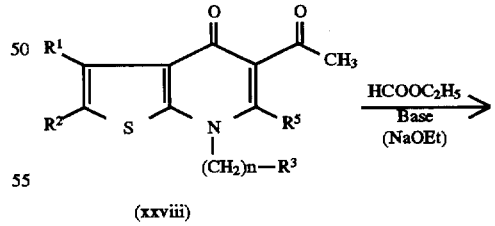

(xxviii)

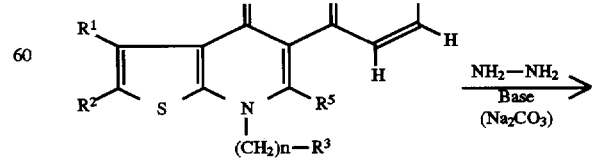

(xxx)

25

-continued

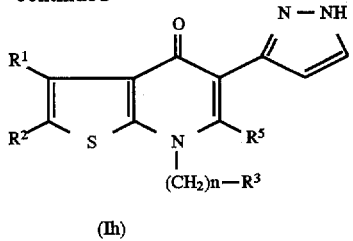

(Ih)

Production Method 13

Production of a compound having 2-triazolyl at 5-position is illustrated in Scheme 13, infra:

4,7-Dihydro-5-thiocarbamoyl-4-oxothieno[2,3-b] pyrimidine derivative (xxxi), which is produced in the first process of Production Method 11, is dissolved in an appropriate solvent, e.g. ethyl ether, dimethylformamide, tetrahydrofurane, dioxane, dichloromethane. To the solution is added an equivalent amount to a small excess amount of methyl iodide at a temperature of 0° C. to 80° C., and the mixture is subjected to refluxing under heating if required, to give a derivative of tetra salt.

To a solution of the derivative in an appropriate solvent, e.g. dimethylformamide, or to the derivative without such solvent, is added an excess amount of formic acid hydrazide under room temperature or ice-cooling.

The mixture is stirred at room temperature to 200° C., to give a 2-triazol derivative (Ii).

The foregoing method is shown in Scheme 13. In Scheme 13, the groups have the same meaning as defined above.

Scheme 13:

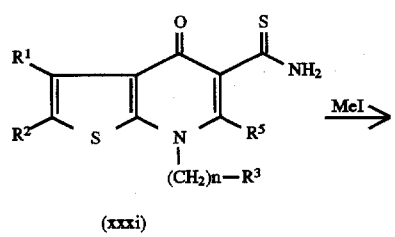

(xxxi)

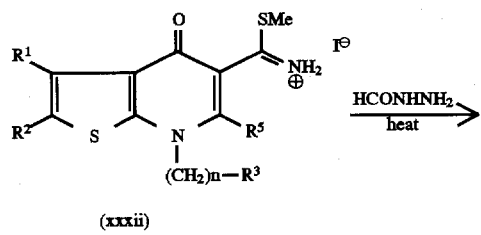

(xxxii)

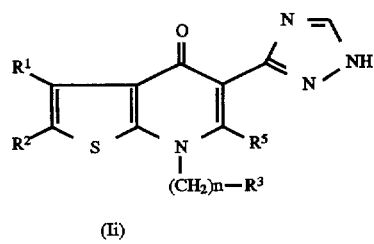

(Ii)

Production Method 14

Production of a compound having 2-oxazolinyl at 5-position illustrated in Scheme 14, infra:

2,7-Dihydro-4-oxothieno[2,3-b]pyridine-5-carboxylic acid ester (xxxviii) is added dropwise under ice-cooling to an excess amount of a solution of aluminum amide of ethanol amine in dichloromethane. The mixture is stirred for one to 4 hours at room temperature to produce an amide derivative.

To the solution of the amide derivative in an appropriate solvent, e.g. dichloromethane, ethyl ether, tetrahydrofuran, is added thionyl chloride under ice-cooling.

The mixture is stirred at a temperature of 0° C. to room temperature to give a 2-oxazolinyl derivative (Ij).

The foregoing method is shown in Scheme 14. In the Scheme 14, $R^1$, $R^2$, $R^3$, $R^5$ and n have the same meaning as defined above.

Scheme 18:

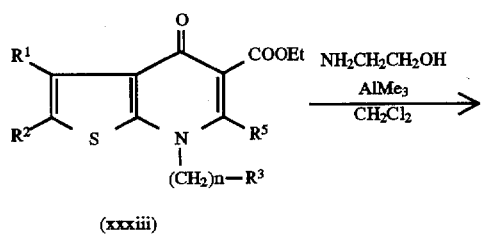

(xxxiii)

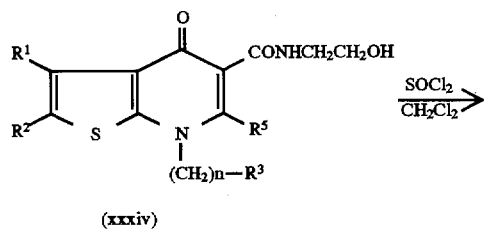

(xxxiv)

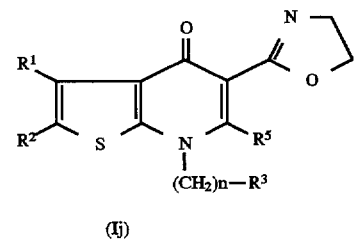

(Ij)

Production Method 15

Production of the compound (I) wherein $R^4$ is a group bonded through a nitrogen atom is illustrated in Scheme 15, infra:

The compound (xxxv), which can be produced by a similar manner of Production Methods 4 or 5, is dissolved in an appropriate solvent, e.g. pyridine. To the solution is added an equivalent to a small excess amount of hydroxylamine derivative or its salt, and the mixture is reacted under room temperature or an elevated temperature, to produce oxime derivative (xxxvi). The oxime derivative (xxxvi) is dissolved in an appropriate solvent, e.g. pyridine, and to the solution is added an equivalent to a small excess amount of an acylating agent, e.g. acid halide, acid anhydride, sulfonic acid halide.

The mixture is reacted, under room temperature or under heating for 1 to 12 hours to give a dislocation form (Ik).

The dislocation form (Ik) is dissolved in an appropriate solvent, e.g. ethylalcohol, and to the solution is added an alkali, e.g. an sodium hydroxide solution, and the mixture is stirred for about 2 hours to cause an alkali hydrolysis reaction, whereby a primary amino derivative (Im) is produced.

The foregoing method is shown in Scheme 15. In Scheme 15, $R^1$, $R^2$, $R^3$, $R^5$ and n have the same meaning as defined above. Ac means acetyl group.

Scheme 15:

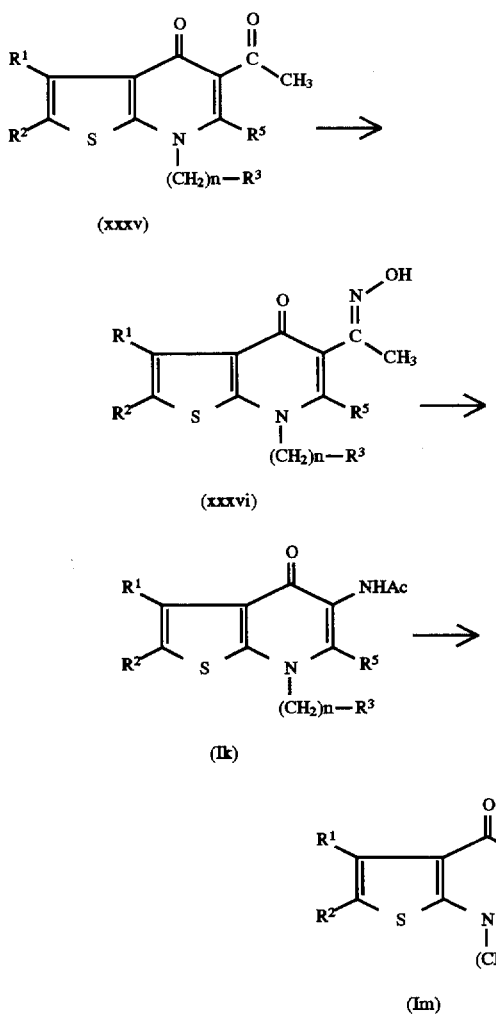

From thus obtained primary amino derivative (Im), various derivatives can be produced by alkylation, acylation, sulfonation, imidation and so forth.

Production Method 16

Production of the compound (I) wherein $R^4$ is a group bonded through an oxygen atom is illustrated in Scheme 16, infra:

The compound (xxxvii), which can be obtained by the method described in Production Methods 4 or 5, is dissolved in an appropriate solvent, e.g. dichloromethane. To the solution is added a small excess amount, e.g. 1.2 to 1.5 equivalent, of peracids, e.g. chlorobenzoic acid, and the mixture is stirred for 1 to 6 hours to give a dislocation from (In).

The dislocation form (In) is subjected to a reaction by stirring the mixture of the dislocation form (In) with an alkali, e.g. 2N sodium hydroxide solution, in an appropriate solvent, e.g. tetrahydrofuran, under room temperature or under heating, e.g. 40° to 60° C., for 1 to 12 hours, to give an alcoholic derivative (Io).

The alcoholic derivative (Io) is dissolved in an appropriate solvent, e.g. dimethylformamide, and to the solution are added an alkali, e.g. potassium carbonate, and alkyl halide, e.g. isopropyl bromide, and the mixture is stirred for about one to 24 hours at room temperature to heating, e.g. 40° to 80° C., to give alkoxy derivative (Ip).

Furthermore, when the alkoxy group is isopropoxy group, the alkoxy derivative (xviii) is dissolved in an appropriate solvent, e.g. dichloromethane, an excess amount of Lewis acid, e.g. borone trichloride, is added to the solution and the mixture is stirred for one to 6 hours under ice-cooling or room temperature, to give de-alkylated alcoholic derivative (Io).

The foregoing methods are shown in Scheme 16. In Scheme 16, $R^1$, $R^2$, $R^3$, $R^5$ and n have the same meaning as defined above. $R^{30}$ and $R^{4'}$ denote an alkyl group. Xa denotes a halogen atom.

Scheme 16:

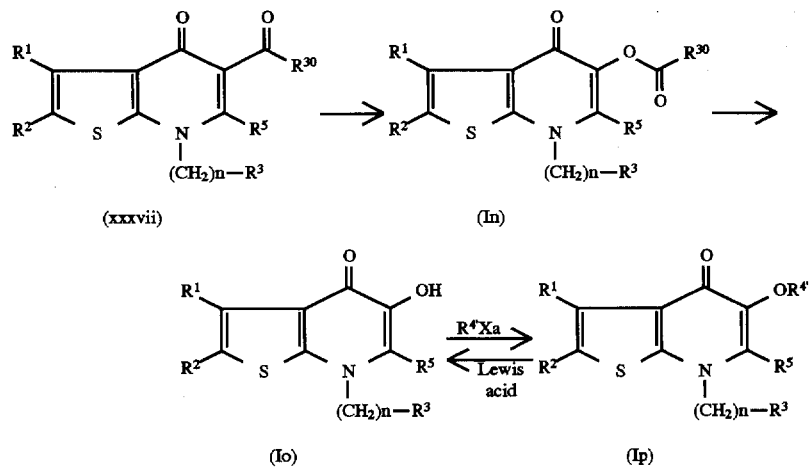

From the obtained alcoholic derivative (xvii), various derivatives can be produced by alkylation, acylation, alkenylation, sulfonation and so forth.

Production Method 17

Production of the compound (I) wherein $R^4$ is a group bonded through a sulfur atom is illustrated in Scheme 17, infra:

At first, thioglycolic acid ester is reacted with an alkali iodide, and then the product is reacted with dimethylaminomethylene compound to give a compound (xxxviii).

The 2-aminothiophen derivative (xxxix), which is obtained in the above Production Method 1, Scheme 1, is dissolved in an appropriate solvent, e.g. ethyl alcohol, and to the solution is added a base, e.g. an aqueous sodium hydroxide solution, to cause to alkali hydrolysis to give a compound (xxxx).

The compound (xxxx) is reacted with the compound (xxxviii) shown above by stirring in an appropriate solvent, or without any solvent, under heating, e.g. 80 to 150° C., for 1 to 6 hours to give an amino substituted derivative (xxxxi).

The derivative (xxxxi) is heated, e.g. at 150° to 250° C., in an appropriate solvent, e.g. diphenyl ether, for 30 minutes to 3 hours to give a cyclic form (xxxxii).

The cyclic form (xxxxii) is reacted with a compound of the formula: Xa—(CH$_2$)$_n$—R$^3$ by a similar manner as described above in the reaction with a compound of the formula: Xa—(CH$_2$)$_n$—R$^3$ in the Production Method 6, to give a compound (Iq).

Furthermore, the compound (Iq) is reacted by stirring with an equivalent to an excess amount of peracid compound, e.g. m-chlorobenzoic acid, in an appropriate solvent, e.g. dichloromethane, under ice-cooling for 5 minutes to about 2 hours to give sulfoxide derivative (Ir).

The foregoing methods are shown in Scheme 17. In Scheme 17, $R^1$, $R^2$, $R^3$ and n have the same meaning as defined above. $R^{4''}$ denotes an alkyl group.

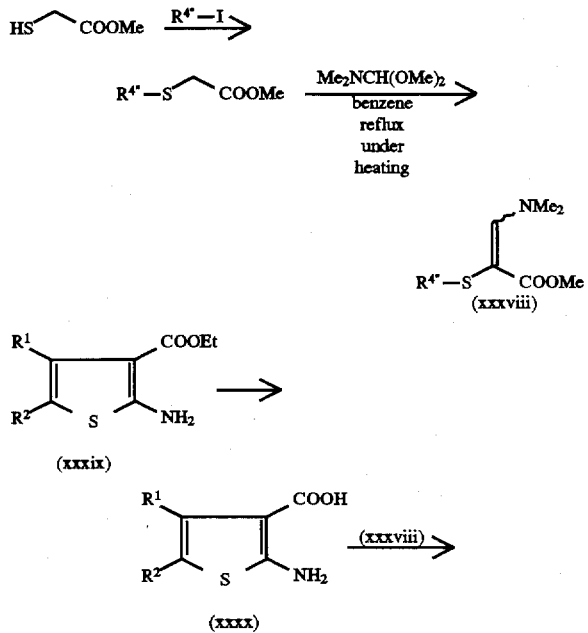

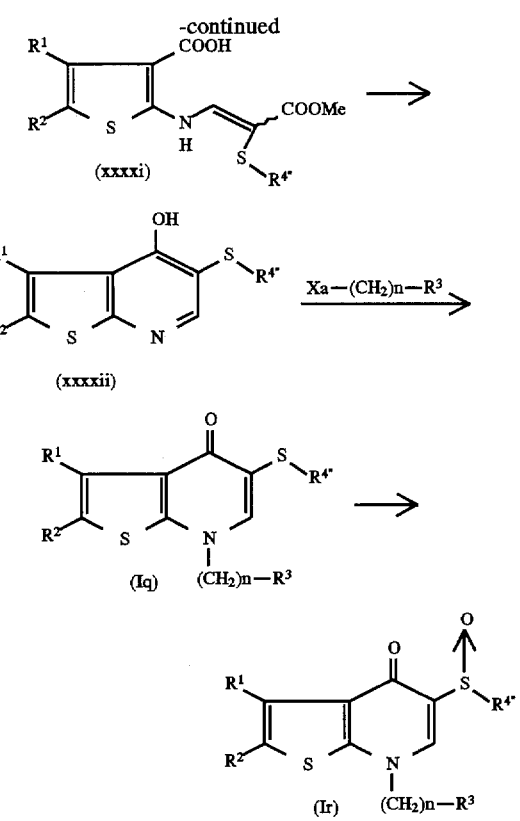

Production Method 18

Production of the Compound wherein it has a phenyl group substituted by an alkenyl group which may optionally be substituted at 2-position is illustrated in Scheme 18, infra:

4,7-Dihydro-2-(4-aminophenyl)-4-oxothieno[2,3-b] pyrimidine derivative (Is) is reacted with diazonizing agent, e.g. sodium nitrite, isoamyl nitrite, in an appropriate proper solvent, e.g. dimethylformamide, dichloromethane, tetrahydrofuran, dioxane, acetenitrile, water, etc, to give a diazonium salt.

To the diazonium salt is added one equivalent to excess amount of an alkenyl derivative, e.g. olephine compound, and palladium catalyst, e.g. bis(dibenzylideneacetone) palladium. The reaction is conducted at 0° C. to 80° C. under stirring, to give the desired product, i.e. the compound (It).

The foregoing production method is shown in Scheme 18. In Scheme 18, $R^{32}$ and $R^{33}$ independently are an acyl group, $R^{34}$ denotes a hydrogen atom or $C_{1-6}$ alkyl. Other groups have the same meaning as defined above.

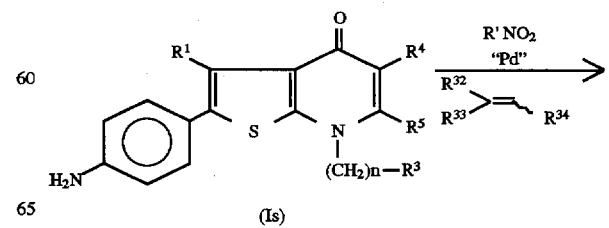

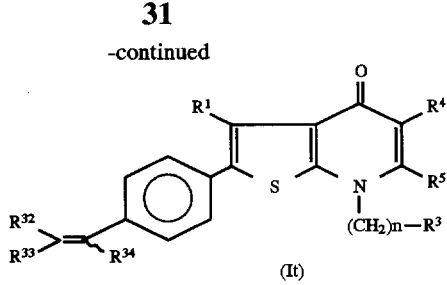

(It)

Production Method 19

Production of a compound which has an aminophenyl group substituted by (1) an optionally substituted alkyl group or (2) an optionally substituted homo-cyclic group is illustrated in Scheme 19, infra:

4,7-Dihydro-2-(4-aminophenyl)-4-oxothieno[2,3-b]pyrimidine derivative (Iu) is dissolved in an appropriate solvent, e.g. acetic acid, dimethylformamide, dichloromethane, tetrahydrofuran, dioxane. To the solution is added one equivalent to excess amount of Michael acceptor derivative, e.g. acrylic acid ester, or an oxyrane derivative, e.g. epoxy compound. The reaction is carried out at 0° C. to 80° C. under stirring to give the desired compound (Iv).

The foregoing production method is shown in Scheme 19. In Scheme 19, $R^{35}$ to $R^{39}$ denote alkyl group —$R^{40}$ denotes a group —C($R^{36}$)—CO—$R^{35}$ or a group —C(OH)$R^{36}R^{39}$. Other groups have the same meaning as defined above.

tetrahydrofuran, ethylether, dioxane, acetone, and to the solution is added one equivalent to an excess amount of a base, e.g. potassium carbonate, triethylamine, sodium hydrogen, and one equivalent to one excess amount of a halogenated alkyl, e.g. methyl iodide, propyl iodide, benzyl iodide. The reaction is carried out at 0° C. to 80° C. under stirring.

The obtained derivative is subjected to alkali hydrolysis using small excess amount of 1N sodium hydroxide in an appropriate solvent, e.g. tetrahydrofuran, dioxane, ethanol, methanol, acetone, to give the desired derivative (Iy).

The foregoing method is shown in Scheme 20. In Scheme 20, the group $R^{41}$ represents $C_{1-6}$ alkyl or trifluoromethyl. The group $R^{42}$ is an optionally substituted alkyl group or an optionally substituted homo-cyclic group. Other groups have the same meaning as defined above.

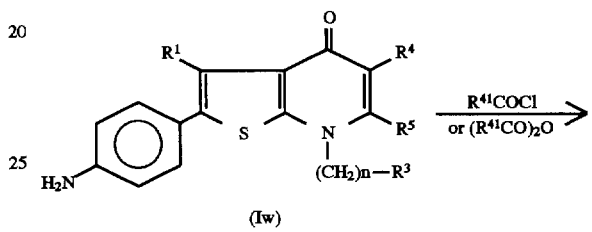

(Iw)

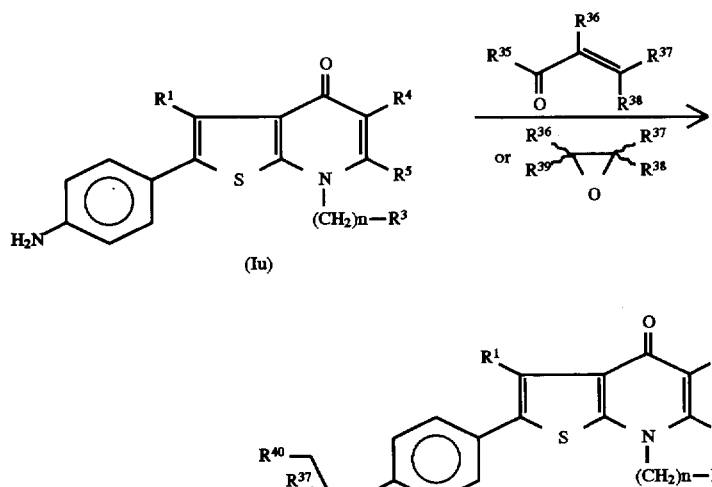

Production Method 20

Production of a compound which has an aminophenyl group substituted by (1) an optionally substituted alkyl or (2) an optionally substituted homo-cyclic group is illustrated in Scheme 20, infra:

4,7-Dihydro-2-(4-aminophenyl)-4-oxothieno[2,3-b]pyrimidine derivative (Iw) is dissolved in an appropriate solvent, e.g. pyridine, dimethylformamide, dichloromethane, tetrahydrofuran, ethylether, dioxane. To the solution is added one equivalent to one excess amount of acid chloride or acid anhydride, e.g. trifluoroacetic acid anhydride. The reaction is carried out at 0° C. to 80° C. under stirring to give a derivative (Ix).

The obtained derivative (Ix) is dissolved in a solvent, e.g. pyridine, dimethylformamide, dichloromethane,

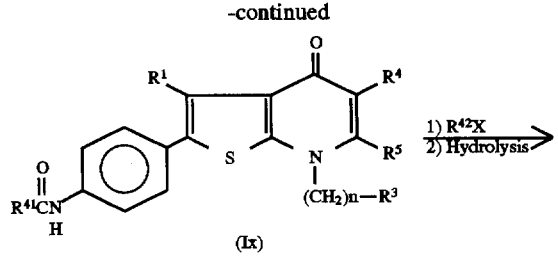

(Ix)

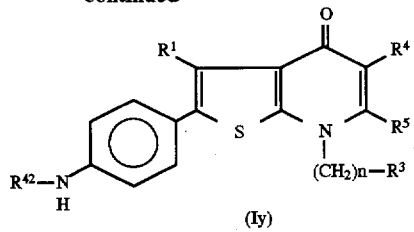

(Iy)

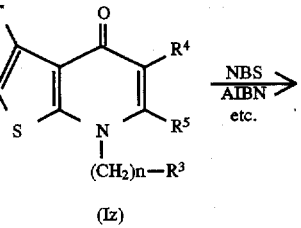

(Iz)

Production Method 21

Exchange the group at 3-position:

The group at 3-position of the compound can be exchanged by the following method as illustrated in Scheme 21.

The compound (Iz) is stirred together with N-bromosuccinimide (NBS) in an appropriate solvent, e.g. halogenated hydrocarbons such as carbon tetrachloride and chloroform, in the presence of α, α"-azobisisobutyronitrile (AIBN), at temperatures ranging from about 30° to 100° C. to give a compound (II'), and if required the compound (II') is subjected to a reaction with aliphatic carboxylic acid, alkylsulfonic acid, or alkylarylsulfonic acid to cause a reaction of exchanging the group at 3-position.

The compound (II') is reacted with an equivalent mole to a small excess amount (about 3 mole) of primary or secondary amine, e.g. R$^{1'}$—H to give a compound (III'). The reaction can be carried out in an appropriate solvent which does not adversely effect the reaction. As the solvent, mention is made of amides such as dimethylformamide or dimethylacetamide, nitriles such as acetonitrile, alcohols such as ethanol, and furthermore diethoxyethane, tetrahydrofuran, dioxane, toluene, dichloromethane, chloroform, ethylether, acetone and ethyl acetate can be used. In this reaction, if necessary, a base may be used. As the base, mention is made of a tertiary organic amine, e.g. trimethylamine, triethylamine, diisopropylamine, pyridine, 1,8-diazabicyclic[5,4,0]-7-undecene (DBU), and an inorganic salt, e.g. anhydrous potassium carbonate. The reaction is carried out at a temperature of about 10° to 100° C. The reaction time is about 0.5 to 8 hours. When the reaction is carried out under stirring, the reaction proceeds smoothly.

This reaction gives the compound (III'). The production method 3 described above is shown in Scheme 21 below:

In Scheme 21, the groups R$^{1"}$, R$^{1'}$, R$^2$, R$^3$, R$^5$ and m have the same meaning as defined above. m denotes an integer of 0 to 6. X denotes a leaving group.

As the leaving group shown by X, mention is made of, for example, a group which is potentially substituted by a nucleophilic reagent such as a hydrocarbon residue having a hetero atom, e.g. an oxygen atom, a sulfur atom, a nitrogen atom, being negatively charged. The preferable examples of the leaving group include halogen, e.g. iodine, bromine chlorine), alkanoyloxy, e.g. acetoxy), alkylsulfonyloxy, e.g. methanesulfonyloxy), alkyl-arylsulfonyloxy (e.g. p-toluenesulfonyloxy).

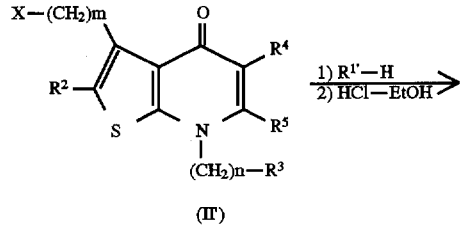

(II')

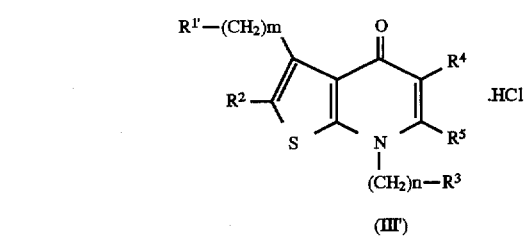

(III')

The compound having a group R$^4$ at 5-position can be produced by the similar manner as above.

22. Other methods

The substituents on the compound (I) can be converted to other substituents by per se known and conventional methods. Examples of the methods are shown below.

(i) The nitro group as the substituent can be converted to an amino group when the starting compound is dissolved in an appropriate solvent, e.g. ethanol, methanol, and (a) to the solution is added palladium-carbon, and the mixture is reacted at room temperature for one to 12 hours under hydrogen atmosphere, or (b) to the solution is added iron powder and hydrochloric acid, and the mixture is reacted at room temperature for one to 12 hours.

(ii) The amino group can be converted to an acylated amino group by dissolving the starting compound in an appropriate solvent, e.g. tetrahydrofuran, dimethylsulfoxide, to the solution is added potassium carbonate, pyridine and triethylamine as a base and acid anhydride or acid halide. The mixture is reacted at a room temperature for one to 10 hours under stirring.

(iii) From an amino compound, a compound having an amino group is converted to alkenyl-amino compound. For example, the starting compound is dissolved in an appropriate solvent, e.g. acetic acid, dimethylformamide, dichloromethane, tetrahydrofuran, dioxane, acetonitrile, to the solution is added diazonizing agent, e.g. sodium nitrite, isoamyl nitrite, to the mixture is added palladium catalyst, e.g. bis(dibenzylideneacetone)palladium and one to excess equivalents of alkenyl derivative, and the mixture is stirred at room temperature to heating (about 80° C.) for one to 12 hours.

(iv) A carbon atom can be introduced to the amino group, for example, to the starting compound in an appropriate solvent, e.g. acetic acid, dimethylformamide, dichloromethane, tetrahydrofuran, dioxane, is added an acrylic acid derivative or oxirane derivative, e.g. epoxide compound. The mixture is stirred at 0° to 80° C. for 6 to 24 hours.

(v) A sulfur atom can be introduced to the amino group in the compound, for example, to the starting compound in an appropriate solvent, e.g. pyridine, dimethylformamide, dichloromethane, tetrahydrofuran, ethylether, dioxane, is added halide of sulfur compound. The mixture is stirred at 0° to 80° C. for 6 to 24 hours.

(vi) The substituent, formyl group, can be converted to methyl group by dissolving a starting compound in an appropriate solvent, e.g. tetrahydrofuran, and to the mixture is added an organic borane, derivative, e.g. dimethylsulfide borane, and the mixture is reacted at room temperature to heating under reflux for a several hours, e.g. one to 3 hours.

(vii) From methoxy derivative, actonyloxy derivative can be prepared by dissolving the starting material in an appropriate solvent, e.g. dichloromethane, and to the solution is added one to excess equivalents of Lewis acid, e.g. aluminium chloride, and thiol compound or sulfide compound, e.g. dimethylsulfide, and the mixture is reacted at ice-cooling to room temperature for one to 10 hours, and then the obtained hydroxy derivative is dissolved in an appropriate solvent, e.g. dimethylformamide, to the solution is added a base, e.g. sodium hydroxide or potassium carbonate, and an alkyl halide. The mixture is reacted at a room temperature for one to 12 hours.

(viii) A methoxy group can be changed to isopropoxy by dissolving the starting material in an appropriate solvent, e.g. dichloromethane, to the solution is added one to excess equivalents of Lewis acid, e.g. aluminum chloride, and thiol compound or sulfide compound, e.g. dimethylsulfide, and the mixture is reacted at room temperature to ice-cooling for one to 10 hours.

(ix) An aminocarbonyl group can be introduced by dissolving a starting compound having halogen atom in an appropriate solvent, e.g. dimethoxyethane, to the solution is added arylborric acid derivative, a base, e.g. sodium carbonate, a palladium compound e.g. tetrakis (triphenylphosphine)palladium(0), as a catalyst and the mixture is refluxed 1 to 6 hours.

(x) An alkylthio compound can be converted to an alkylsulfinyl compound or an alkylsulfonyl compound by reacting a starting compound with an oxidizing agent, e.g. metachloroperbenzoic acid, in an appropriate solvent, e.g. dichloromethane, at ice-cooling to heating. With vigorous heating or by treating with an excess amount of oxidizing agent, an alkylsulfonyl compound is obtained.

As salts of the compound (I) of this invention obtained thus above, physiologically acceptable acid addition salts are preferable. Examples of such salts include those with an inorganic acid, e.g. hydrochloric acid, hydrobromic acid, nitric acid, sulfuric acid and phosphoric acid, or those with an organic acid, e.g. formic acid, acetic acid, trifluoroacetic acid, fumaric acid, oxalic acid, tartaric acid, maleic acid, citric acid, succinic acid, malic acid, methanesulfonic acid, bezenesulfonic acid, and p-toluenesulfonic acid. Further, when the compound (I) of this invention has an acid group such as —COOH, the compound (I) may form a salt with an inorganic base, e.g. an alkali metal or alkaline earth metal such as sodium, potassium, calcium and magnesium; ammonia, or an organic base, e.g. trimethylamine, triethylamine, pyridine, picolin, ethanolamine, diethanolamine, triethanolamine, dicyclohexylamine and N,N'-dibenzylethylenediamine.

The compounds or salts thereof of the present invention produced thus above can be isolated and purified by conventional separating means such as recrystallization, distillation and chromatography. In the case where the compound (I) is produced in the free form, it can be converted to a salt thereof by a per se conventional means or a method analogous thereto. On the contrary, when it is obtained in the form of a salt, it can be converted to its free form or to any other salt.

In the case where the compound or a salt thereof of the present invention is an optically active compound, it can be separated into d-compound and l-compound by means of a conventional optical resolution.

Since the compounds (I) of this invention or its salt, hereinafter it is sometimes abbreviates as "the present compound", have a GnRH antagonistic activity and are low in toxicity, and is stably absorbed through oral administration and shows GnRH antagonistic activity over a long time, they can be safely used for the therapy of male hormone or female hormone dependent diseases as well as the therapy of diseases caused by excess secretion of these hormones, in mammals, e.g. human, monkey, cow, horse, dog, cat, rabbit, rat and mouse, suppressing the secretion of gonadotropic hormone by the action of GnRH receptor antagonistic action. More specifically, the present compound are effective as a prophylactic or therapeutic agent for the prevention or treatment of several hormone dependent diseases, for example, a sex hormone dependent cancer, e.g. prostate cancer, cancer of the uterine cervix, breast cancer, pituitary adenoma, benign prostatic hypertrophy, myoma of the uterus, endometriosis, precocious puberty, amenorrhea, premenstrual syndrome, polycystic ovary syndrome and acne vulgaris. And, the present compound are also effective as a fertility controlling agent in both sexes, e.g. pregnancy controlling agents and menstrual cycle controlling agents. The present compound can be further used as a contraceptive of male or female and, as an ovulation-inducing agent of female. The present compound can be used as an infertility treating agent by using a rebound effect owing to a stoppage of administration thereof. Further, the present compounds are useful as modulating estrous cycles in animals in the field of animal husbandry, and as an agent for improving the quality of edible meat or promoting the growth of animals. The present compounds are also useful as an agent for spawning promoting in fish. While the present compound can be used singly, they can also effectively be used by administering in combination with a steroidal or non-steroidal antiandrogenic agent. The present compound can be used for the suppressing a passing ascent of testosterone concentration in plasma, the ascent which occurs in administration of GnRH super antagonist such as leuprorelin acetate. The present compound can effectively be used by administering in combination with a chemotherapeutic agent for cancer. In treatment of prostate cancer, examples of the chemoterapeutic agent include Ifosfamide, UFT, Adriamycin, Peplomycin, Cisplatin and the like. In treatment of breast cancer, examples of the chemotherapeutic agent include Cyclophohamide, 5-FU-, UFT, Methotrexate, Adriamycin, Mitomycin C, Mitoxantrone and the like.

When the present compound is employed, in the field of animal husbandry or fisheries, as prophylactic and therapeutic agents of the above-mentioned diseases, it can be administered orally or non-orally in accordance with per se known means. For example, it can be mixed with a pharmaceutically acceptable carrier and administered orally as a solid preparation such as tablet, capsule, granule or powder, or non-orally as intravenous, subcutaneous or intramuscular injection, or as suppository or a sublingually administrable tablet. Further, it can be sublingually, subcutaneously or intramuscularly administered as a prolonged release formulation such as sublingually administrable tablets, or microcapsules. The dosage can vary with, e.g. the degree of affliction, age, sex, body weight and difference of sensitivity of the subject to be administered; the time and intervals of administration, treated dosage forms and kinds of the medicinal preparation; and kinds of the effective components, and it ranges usually, though not specifically limited to, from about 0.1 to 30 mg, preferably from about 0.1 to 3 mg, more preferably from about 0.1 to 1 mg, relative to 1 kg body weight of mammals, which is administered usually once daily or by 2 to 4 divided dosages. The daily dose when used in the field of animal husbandry or fishery varies with the conditions analogous to those mentioned above, it ranges, relative to 1 kg body weight of the subject animal or fish, from about 0.01 to 5 mg, preferably from about 0.03 to 3 mg, once daily or by 2 to 3 divided dosages.

As the above-mentioned pharmaceutically acceptable carriers, conventional various organic or inorganic carriers are used, and they can be incorporated as excipients, lubricants, binders, disintegrants in solid compositions; and as solvents, solubilisers, suspending agents, isotonizing agents, buffering agents and pain-easing agents in liquid and solid compositions. And, depending on necessity, further additives such as preservatives, anti-oxidants, coloring agents and sweeteners can also be used.

Preferable examples of the above-mentioned excipients include lactose, sugar, D-mannito, starch, crystalline cellulose and more volatile silicon dioxide. Preferable examples of the above-mentioned lubricants include magnesium stearate, calcium stearate, talc and colloid silica. Preferable examples of the above-mentioned binders include crystalline cellulose, sugar, D-mannitol, dextrin, hydroxypropyl cellulose, hydroxymethyl cellulose and polyvinyl pyrrolidone. Preferable examples of the above-mentioned disintegrants include starch, carboxymethyl cellulose, carboxymethyl cellulose calcium, cross carmelose sodium, cross carmelose sodium and carboxymethyl starch sodium. Preferable examples of the above-mentioned solvents include water for injection, alcohol, propylene glycol, macrogol, sesame oil and corn oil. Preferable examples of the above-mentioned solubilizers include polyethylene glycol, propylene glycol, D-mannitol, benzyl benzoate, ethanol, trisaminomethane, cholesterol, triethanolamine, sodium carbonate and sodium citrate. Preferable examples of the above-mentioned suspending agents include surfactants such as stearyl triethanolamine, sodium lauryl sulfate, lauryl aminopropionic acid, lecithin, benzalkonium chloride, benzetonium chloride and monostearic glyceryl ester; and hydrophilic polymers such as polyvinyl alcohol, polyvinyl pyrrolidone, sodium carboxymethyl cellulose, methyl cellulose, hydroxymethyl cellulose, hydroxyethyl cellulose and hydroxypropyl cellulose. Preferable examples of the above-mentioned isotonizing agents include sodium chloride, glycerin and D-mannitol. Preferable examples of the above-mentioned buffering agents include buffer solutions such as phosphate, acetate, carbonate and citrate. Preferable examples of the above-mentioned pain-easing agents include benzyl alcohol. Preferable examples of the above-mentioned preservatives include parahydroxybenzoic acid esters, chlorobutanol, benzyl alcohol, phenethyl alcohol, dehydroacetic acid and sorbic acid. Preferable examples of the above-mentioned anti-oxidants include sulfite and ascorbic acid.

To the compound of this invention, are added, for example, a suspending agent, a solubilizer, a stabilizer, an isotonizing agent and a preservative, then the mixture is formulated, in accordance with a per se known method, into an intravenous, subcutaneous or intramuscular injection. These injections can be processed into lyophilized preparations, when necessary, by a per se known method.

Examples of the above-mentioned pharmaceutical composition are oral agents (e.g. diluted powders, granules, capsules and tablets), injections, dropping injections, external agents (e.g. transnasal preparations, percutaneous preparations, etc.), ointments (e.g. rectal ointment, vaginal ointment, etc.) and the like.

Such pharmaceutical compositions can be manufactured by a per se known method commonly used in preparing pharmaceutical compositions.

The compound of the present invention or a salt thereof can be made into injections either in a form of an aqueous injection together with dispersing agents, e.g. Tween 80 (Atlas Powder, U.S.A.), HCO 80 (Nikko Chemicals, Japan), polyethylene glycol, carboxymethylcellulose, sodium alginate, etc., preservatives, e.g. methyl paraben, propyl paraben, benzyl alcohol, etc., isotonizing agents, e.g. sodium chloride, mannitol, sorbitol, glucose, etc., and the like or in a form of an oily injection by dissolving, suspending or emulsifying in plant oil, e.g. olive oil, sesame oil, cotton seed oil, corn oil, etc., propylene glycol and the like.

In preparing a pharmaceutical composition for oral use, the compound of the present invention or a salt thereof is molded by compressing, for example, with fillers, e.g. lactose, sucrose, starch, etc., disintegrating agents, e.g. starch, calcium carbonate, etc., binders, e.g. starch, gum arabic, carboxymethylcellulose, polyvinylpyrrolidone, hydroxypropylcellulose, etc., or lubricants, e.g. talc, magnesium stearate, polyethylene glycol 6000, etc., and the like. If necessary, the composition is coated by a per se known method with an object of masking the taste, as an enteric coating or for long-acting sustained release. Examples of coating agents therefore are hydroxypropylmethylcellulose, ethylcellulose, hydroxymethylcellulose, hydroxypropylcellulose, polyoxyethylene glycol, Tween 80, pluronic F 68, cellulose acetate phthalate, hydroxypropylmethylcellulose phthalate, hydroxymethylcellulose acetate succinate, Eudragit (a copolymer of methacrylic acid with acrylic acid; manufactured by Rohm, Germany), red oxide of iron and the like. Subcoating layers may be provided between the enteric coating and the core according to per se known methods.

In preparing an external composition, the compound of the present invention or a salt thereof is subjected to a per se known method to give a solid, semisolid or liquid agent for external use. For example, the solid preparation is manufactured as follows. The compound of the present invention as it is or after adding/mixing fillers, e.g. glycol, mannitol, starch, microcrystalline cullulose, etc., thickeners, e.g. natural gums, cellulose derivatives, acrylic acid polymers, etc., and the like thereto/therewith is made into a powdery composition. With respect to the liquid composition, an oily or aqueous suspension is manufactured by the manner nearly the same as in the case of the injection. In the case of a semisolid composition, the preferred one is an aqueous or oily gel or an ointment. Each of them may be compounded with a pH adjusting agent, e.g. carbonic acid, phosphoric acid, citric acid, hydrochloric acid, sodium hydroxide, etc., an antiseptic agent, e.g. p-hydroxybenzoates, chlorobutanol, benzalkonium chloride, etc., and the like.

In the manufacture of an ointment for example, the compound of the present invention or a salt thereof can be made into an oily or an aqueous solid, semisolid or liquid ointment. Examples of the oily base material applicable in the above-mentioned composition are glycerides of higher fatty acids, e.g. cacao butter, Witepsols (manufactured by Dynamite-Nobel), etc., medium fatty acids, e.g. Miglyols (manufactured by Dynamite-Nobel), etc., and plant oil, e.g. sesame oil, soybean oil, cotton seed oil, etc., and the like. Examples of the aqueous base material are polyethylene glycols and propylene glycol and those of the base material for aqueous gel are natural gums, cellulose derivatives, vinyl polymers, acrylic acid polymers, etc.

By way of the following Reference Examples and Working Examples the present invention will be described more specifically, but they are not intended to limit the scope of this invention thereto.

$^1$H-NMR spectra were taken with the Varian GEMINI 200 (200 MHz) type spectrometer, JEOL LAMBDA300 (300MHz) type spectrometer or the Brucker AM 500 (500 MHz) type spectrometer, employing tetramethylsilane as the internal standard. All delta values were expressed in ppm.

The symbols used in the present specification have the following meanings:

s: singlet, d: doublet, t: triplet, dt: double triplet, m: multiplet, br: broad

Reference Example 1

Production of 2-amino-5-phenylthiophene-3-carboxylic acid ethyl ester

To a mixture of ethyl cyanoacetate (6.1 g, 50 mmol), sulfur (1.61 g, 50 mmol), triethylamine (3.5 ml, 25 mmol) and dimethylformamide (10 ml) was added dropwise, with stirring at 45° C., phenylacetaldehyde (50% diethylphthalate solution; 12.05 g, 50 mmol) for 20 minutes. The mixture was stirred for 9 hours at 45° C., and the reaction mixture was concentrated. The resulting residue was extracted with ethylacetate. The extract was washed with an aqueous sodium chloride solution, which was then dried (MgSO$_4$), followed by distilling off the solvent under reduced pressure. The residue was chromatographed on silica gel, followed by crystallization from ether-hexane to give slightly yellow plates (5.55 g, 45%), m.p.124.5°–125.5° C. (value in literature reference 123°–124° C.).

Elemental Analysis for $C_{13}H_{13}NO_2S$: C(%) H(%) N(%) Calcd.: 63.13; 5.30; 5.66 Found: 62.99; 5.05; 5.63

$^1$H-NMR (200 MHz, CDCl$_3$) δ: 1.37(3H,t,J=7.1 Hz), 4.30(2H,d,J=7.1 Hz), 5.97(2H,br), 7.17–7.46(6H,m).

IR(KBr): 3448, 3320, 1667, 1590, 1549 cm$^{-1}$.

Reference Example 2

Production of 2-amino-4-methyl-5-(4-methoxyphenyl)thiophene-3-carboxylic acid ethyl ester A mixture of 4-methoxyphenylacetone (16.5 g, 0.10 mol), ethyl cyanoacetate (12.2 g, 0.10 mol), ammonium acetate (1.55 g, 20 mmol), acetic acid (4.6 ml, 80 mmol) and benzene (20 ml) was heated for 24 hours under reflux, while removing water produced in the reaction mixture using a Dean and Stark apparatus. After cooling, the reaction mixture was concentrated under reduced pressure. The residue was partitioned between dichloromethane and an aqueous sodium hydrogencarbonate solution. The organic layer was washed with an aqueous sodium chloride solution, which was then dried (MgSO$_4$), followed by distilling of the solvent under reduced pressure. To an ethanol (30 ml) solution of the residue were added sulfur (3.21 g, 0.10 mol) and diethylamine (10.4 ml, 0.10 mol). The mixture was stirred at 50°–60° C. for 2 hours and then concentrated, and the concentrate was extracted with ethyl acetate. The extract was washed with an aqueous sodium chloride solution and dried (MgSO$_4$), followed by distilling off the solvent under reduced pressure. The residue was chromatographed on silica gel, and crystallized from ether-hexane to give a pale yellow plates (11.5 g, 40%), m.p.79°–80° C.

Elemental Analysis for $C_{15}H_{17}NO_3S$: C(%) H(%) N(%) S(%) Calcd.: 61.83; 5.88; 4.81; 11.01 Found: 61.81; 5.75; 4.74; 10.82

$^1$H-NMR (200 MHz, CDCl$_3$) δ: 1.37(3H,t,J=7.1 Hz), 2.28(3H,s), 3.83(3H,s), 4.31(2H,q,J=7.1 Hz), 6.05(2H,brs), 6.91(2H,d,J=8.8 Hz), 7.27(2H,d,J=8.8 Hz).

IR(KBr): 3426, 3328, 1651, 1586, 1550, 1505, 1485 cm$^{-1}$. FAB-MS m/z: 291 (M$^+$)

Reference Example 3

Production of 2-amino-4-methyl-5-phenylthiophene-3-carboxylic acid ethyl ester

In a similar manner as described in Reference Example 2, phenylacetone was employed instead of 4-methoxyphenylacetone. Also employing cyanoacetic acid ethyl ester (10.5 g, 86.5 mmol), ammonium acetate (1.34 g, 17 mmol), acetic acid (3.96 ml, 69.2 mmol), sulfur (2.78 g, 86.5 mmol) and diethylamine (8.95 ml, 86.5 mmol), and recrystallized from ether-hexane colorless needles (9.05 g, 40%) was obtained, m.p. 64°–65° C.

Value is literature reference: 95° C.

Elemental Analysis for $C_{14}H_{15}NO_2S$: C(%) H(%) N(%) Calcd.: 64.34; 5.79; 5.36 Found: 64.51; 5.77; 5.29

$^1$H-NMR (200 MHz, CDCl$_3$) δ: 1.37(3H,t,J=7.1 Hz), 2.33(3H,s), 4.32(2H,q,J=7.1 Hz), 6.09(2H,br), 7.24–7.42 (5H,m).

IR(KBr): 3388, 3278, 1665, 1584, 1549, 1481 cm$^{-1}$.

Reference Example 4

Production of {3-Ethoxycarbonyl-5-(4-methoxyphenyl)-4-methylthiophen-2-yl}aminomethylene malonic acid diethyl ester To the compound produced in Reference Example 2 (10 g, 343.3 mmol) was added diethyl ethoxymethylene malonate (7.45 g, 34.5 mmol). The mixture was stirred for 2 hours at 120° C. After cooling, to the reaction mixture was added ether to precipitate crystals. The crystals were collected by filtration and washed with ether once more, followed by drying over phosphorus pentoxide under reduced pressure to give pale yellow crystals (14.2 g, 90%), m.p.122°–123° C.

$^1$H-NMR (200 MHz, CDCl$_3$) δ: 1.32(3H,t,J=7.1 Hz), 1.38(3H,t,J=7.2 Hz), 1.41(3H,t,J=7.2 Hz), 2.34(3H,s), 3.85 (3H,s), 4.25(2H,q,J=7. Hz), 4.38(2H,q,J=7.2 Hz), 4.45(2H, q,J=7.2 Hz), 6.95(2H,d,J=8.8 Hz), 7.31(2H,d,J=8.8 Hz), 8.22(1H,d,J=13.4 Hz), 12.74(1H,d,J=13.1 Hz).

IR(KBr): 2984, 1720, 1707, 1688, 1653, 1599, 1518, 1499 cm$^{-1}$.

Reference Example 5

Production of (3-ethoxycarbonyl-5-phenyl-4-methylthiophen-2-yl)aminomethylenemalonic acid ethyl ester In a similar manner as described in Reference Example 4, the objective compound was obtained. m.p.108°–109° C.

Reference Example 6

(1) Production of {3-carboxy-5-(4-methoxyphenyl)-4-methylthiophen-2-yl}aminomethylene malonic acid diethyl ester To a solution of the compound produced in Reference Example 4 (7.0 g, 15.2 mmol) in dioxane (20 ml) was added a solution of potassium hydroxide (5.0 g, 75.7 mmol) in ethanol (30 ml) at 60°–70° C. with stirring. The mixture was stirred for one hour at the same temperature range, and was allowed to stand for one hour at room temperature. To the reaction mixture was added 2N HCl (40 ml, 80 mmol) with ice-cooling. The reaction mixture was concentrated under reduced pressure. Resulting yellow precipitate was collected by filtration, which was then washed with a mixture of cold water and ethanol, followed by drying over phosphorus pentoxide under reduced pressure to give yellow powder (6.1 g, 93%), m.p. 184°–187° C.

$^1$H-NMR (200 MHz, DMSO-$d_6$) δ: 1.24(3H,t,J=7.1 Hz), 1.28(3H,t,J=7.2 Hz), 2.30(3H,s), 3.80(3H,s), 4.15(2H,q,J=7.1 Hz), 4.24(2H,q,J=7.2 Hz), 7.03(2H,d,J=8.7 Hz), 7.37 (2H,d,J=8.7 Hz), 8.08(1H,d,J=13.6 Hz), 12.41(1H,d,J=13.6 Hz).

IR(KBr): 3422, 2980, 1719, 1653, 1607, 1551, 1512 cm$^{-1}$.

(2) Production of (3-carboxy-5-phenyl-4-methylthiophen-2-yl)aminomethylanamalonic acid ethyl ester Using the compound obtained in Reference Examples 5 in a similar manner as described in Reference Example 6(1), the objective compound was obtained. m.p. 187°–190° C.

Reference Example 7

(1) Production of 4-Hydroxy-2-(4-methoxyphenyl)-3-methylthieno[2,3-b]pyridine-5-carboxylic acid ethyl ester To polyphosphoric ester (PPE) (90 ml) was added the compound produced in Reference Example 5 (6.0 g, 13.8 mmol) in small portions at 190° C. with stirring. The mixture was stirred for 30 minutes at the same temperature. The reaction mixture was poured into ice-water, and was subjected to extraction with ethylacetate. The extract solution was washed with an aqueous sodium chloride solution, which was then dried (MgSO$_4$), followed by distilling off the solvent under reduced pressure. The residue was chromatographed on silica gel to give yellow powders (3.65 g, 77%). As the sample for elemental analysis, the powder was recrystallized from ethanol to give yellow crystals, m.p.162°–163° C.

Elemental Analysis for $C_{18}H_{17}NO_4S$: C(%) H(%) N(%) S(%) Calcd.: 62.96; 4.99; 4.08; 9.34 Found: 62.89; 5.04; 4.01; 9.34

$^1$H-NMR (200 MHz, CDCl$_3$) δ1.47(3H,t,J=7.1 Hz), 2.63 (3H,s), 4.87(3H,s), 4.49(2H,q,J=7.1 Hz), 6.99(2H,d,J=8.8 Hz), 7.44(2H,d,J=8.8 Hz), 8.84(1H,s), 12.11(1H,s).

IR(KBr): 3434, 2992, 1692, 1601, 1582, 1535, 1504 cm$^{-1}$. FAB-MS m/z: 344 (MH$^+$)

(2) Production of 4-hydroxy-2-phenyl-3-methylthieno[2,3-b]pyridine-5-carboxylic acid ethyl ester Using the compound obtained in Reference Example 6(2), the similar manner of Reference Example 7(1) gave the titled compound.
m.p. 155°–157° C.

Reference Example 8

Production of 4-hydroxy-5-hydroxymethyl-2-(4-methoxyphenyl)-3-methylthieno[2,3-b]pyridine To a suspension (6 ml) of lithium aluminum hydride (0.0326 g, 0.87 mmol) in anhydrous tetrahydrofuran was added dropwise a solution of the compound produced in Reference Example 7 (0.20 g, 0.58 mmol) in anhydrous tetrahydrofuran (3 ml) at room temperature (15°–35° C., the same range applies hereinafter). The mixture was then stirred for 30 minutes at room temperature, to which was added an aqueous solution of Rochelle salt. Resulting precipitate was removed by filtration. In this process, when necessary, the reaction mixture was subjected to heating under reflux to complete the reaction. The precipitate was washed with ethyl alcohol and chloroform, which was combined with the filtrate, followed by concentration under reduced pressure. The concentrate was partitioned between ethyl acetate and an aqueous sodium chloride solution. The organic layer was dried (MgSO$_4$), from which the solvent was distilled off under reduced pressure to give white crystals (0.13 g, 74%).

mp>300° C.

$^1$H-NMR (200 MHz, DMSO-$d_6$) δ: 2.55(3H,s), 3.81(3H, s), 4.41(2H,s), 7.03(2H,d,J=8.8 Hz), 7.40(2H,d,J=8.8 Hz), 7.75(1H,s).

IR(KBr): 3210, 2930, 1613, 1506, 1255 cm$^{-1}$.

FAB-MS m/z: 302 (MH$^+$)

Reference Example 9

(1) Production of 4,7-dihydro-5-hydroxymethyl-7-(2-fluorobenzyl)-2-(4-methoxyphenyl)-3-methyl-4-oxothieno[2,3-b]pyridine To a solution of the compound produced in Reference Example 8 (4.00 g, 13.3 mmol) in dimethylformamide (300 ml) were added, at room temperature, potassium carbonate (2.78 g, 20.0 mol), 2-fluorobenzyl chloride (2.89 g, 20.0 mol) and potassium iodide (1.10 g, 6.6 mmol). The mixture was stirred for 2 hours at room temperature. The reaction mixture was concentrated, and the concentrate was partitioned between dichloromethane and water. The aqueous layer was extracted with dichloromethane. The extract was washed with an aqueous sodium chloride solution, which was then dried (MgSO$_4$), then the solvent was distilled off under reduced pressure. The residue was chromatographed on silica gel to give a pale yellow amorphous product, which was recrystallized from ethyl acetate to afford colorless crystals, m.p.159°–160° C.

$^1$H-NMR (200 MHz, CDCl$_3$) δ: 2.67(3H,s), 3.85(3H,s), 4.59(2H,s), 5.19(2H,s), 6.96(2H,d), 7.1–7.2(3H,m), 7.3–7.5 (3H,m), 7.47(1H,s).

(2) Production of 4,7-dihydro-2-phenyl-3-methyl- 7-(2,6-difluorobenzyl)-4-oxothieno[2,3-b]pyridine-5-carboxylic acid ethyl ester:

Using the compound obtained in Reference Example 7(2), the similar procedure gave the titled compound.
m.p.184°–186° C.

Reference Example 10

Production of 4,7-dihydro-2-(4-methoxyphenyl)-3-methyl-5-formyl-7-(2-fluorobenzyl)-4-oxothieno[2,3-b]pyridine To a solution of the compound (4.10 g) obtained in Reference Example 9(1) in chloroform is added manganese dioxide (20.5 g). The mixture was stirred for one hour under room temperature.

After Celite filtration, the filtrate was concentrated under reduced pressure, the obtained residue was purified with silica gel column chromatography, and recrystallized from methylene chloride-ethyl acetate to give colorless crystals (3.72 g, Yield 83%).

$^1$H-NMR (200 MHz, CDCl$_3$) δ: 2.66(3H,s), 3.85(3H,s), 5.26(2H,s), 6.96(2H,d), 7.1–7.4(6H,m), 8.17(1H,s), 10.44 (1H,s).

Reference Example 11

Production of methyl 2-isopropylthioacetate:

To a solution of thioglycolic acid methyl ester (75 g, 707 mmol) in methanol (500 ml) was added potassium carbonate (107.4 mg, 777 mmol) and isopropyl iodide (150 g, 882 mmol) under ice-cooling. The mixture was put back to room temperature and stirred for two days, and for one hour at 60° C. The reaction mixture was partitioned between ether (800 ml) and water. The aqueous layer was extracted with ether (200 ml), and the extracts were combined and washed with an aqueous sodium chloride solution, dried with $Na_2SO_4$, and the solvent was removed off. The resultant oily product (105 g, 100%) was used for the next reaction step without purification.

$^1$H-NMR (CDCl$_3$) δ: 1.26(6H,d,J=6.6 Hz), 3.01–3.09(1H, m), 3.25(2H,s), 3.72(3H,s).

Reference Example 12

Production of methyl 2-(N,N-dimethylaminomethylene)-2-isopropylthioacetate

The compound (105 g, 707 mmol), obtained in Reference Example 11, and N,N-dimethylformamidedimethylacetal (150 g, 1,260 mmol) were dissolved in benzene (500 ml). The mixture was refluxed under heating for 5 hours, while removing water which occurs in the reaction system. Thus obtained reaction mixture was purified by distillation to give an oily product (19 g, 13%).

$^1$H-NMR (CDCl$_3$) δ: 1.19(6H,d,J=6.6 Hz), 2.89–2.98(1H, m), 3.26(6H,s), 3.72(3H,s), 7.88(1H,s).

Reference Example 13

Production of 2-amino-5-phenyl-4-methylthiophene-3-carboxylic acid

2-Amino-5-phenyl-4-methylthiophene-3-carboxylic acid ethyl ester (13 mg, 50 mmol), which was obtained in Reference Example 3, was dissolved in ethanol (125 ml). To the solution was added 2N sodium hydroxide solution (150 ml), the mixture was refluxed under heating at 120° C. for 3 hours. The reaction mixture was concentrated to dryness, the residue was partitioned between ethyl acetate (500 ml) and water. The aqueous layer was extracted with ethyl acetate (200 ml), the extracts were combined, washed with an aqueous sodium chloride solution, dried with $Na_2SO_4$, and the solvent was distilled off to give pale brown crystals (11.45 g, 100%).

Reference Example 14

Production of methyl (3-oxycarbonyl-5-phenyl-4-methylthiophen-2-yl)-aminomethylene-(2-isopropylthio)acetate The compound (13.31 g, 57 mmol) obtained in Reference Example 13 and the compound (19 g, 93 mmol) obtained in Reference Example 12 were dissolved in toluene (50 ml), and the solution was refluxed under heating at 120° C. for 1.5 hours. The reaction mixture was concentrated to dryness, and the residue was purified by silica gel column chromatography to give pale yellow needles (15.25 g, 77%).

m.p. 119°–121° C.

mass m/z 347(M+)

$^1$H-NMR (CDCl$_3$) δ: 1.26(6H,d,J=6.3 Hz), 2.25(3H,s), 3.15–3.24(1H,m), 3.79(3H,s), 6.40(1H,s), 7.29–7.41(5H,m), 7.78(1H,d,J=13.2 Hz), 8.18(1H,d,J=13.8 Hz).

Reference Example 15

Production of 4-hydroxy-2-phenyl-3-methyl-5-isopropylthieno[2,3-b]pyridine

The compound (15.25 g, 43.9 mmol) obtained in Reference Example 14 was added to diphenylether(150 ml) under heating (240°–260° C.). The mixture was stirred at the same temperature for 30 minutes. The reaction mixture was concentrated to dryness, and the residue was recrystallized from dichloromethane-n-hexane to give pale yellow crystals (16 g, 103%).

Elemental Analysis for $C_{17}H_{17}NOS_2 \cdot 0.1H_2O$: C(%) H(%) N(%) Calcd.: 64.36; 5.46; 4.41 Found: 64.31; 5.52; 4.26 mass m/z 316(M$^{+1}$)

$^1$H-NMR (CDCl$_3$) δ: 1.30(6H,d,J=6.6 Hz), 2.64(3H,s), 3.07–3.16(1H,m), 7.37–7.54(5H,m), 8.45(1H,s).

EXAMPLE 1

Production of 4,7-dihydro-2-(4-methoxyphenyl)-3-methyl-5-(oxazol-5-yl)-7-(2-fluorobenzyl)-4-oxothieno[2,3-b]pyridine The compound obtained in Reference Example 10 (0.30 g, 0.73 mmol), tosylmethylisocyanide (0.144 g, 0.73 mmol), potassium carbonate (0.102 g, 0.73 mmol) was added to methanol (50 ml). The mixture was refluxed under heating for two hours.

The reaction mixture was concentrated under reduced pressure to dryness. Thus obtained residues was partitioned between ethyl acetate and water. The aqueous layer was extracted with ethyl acetate, and the extracts was combined and washed with an aqueous sodium chloride solution and dried (MgSO$_4$), and the solvent was removed off under reduced pressure.

Purification of the residue with silica gel column chromatography gave pale yellowish solid form, and recrystallization of the solid form from dichloromethane-ethyl acetate-hexane gave colorless crystals (0.182 g, 56%).

m.p. 235°–236° C.

Elemental Analysis for $C_{25}H_{19}N_2O_3SF$: C(%) H(%) N(%) Calcd.: 67.25; 4.29; 6.27 Found: 66.56; 4.25; 6.08

$^1$H-NMR (300 MHz, CDCl$_3$) δ: 2.71(3H,s), 3.85(3H,s), 5.29(2H,s), 6.95(2H,d), 7.14(2H,t), 7.25(1H,td), 7.3–7.4 (3H,m), 7.83(1H,s), 8.07(2H,m).

FAB-MS m/z: 447 (MH$^+$).

EXAMPLE 2

Production of 4,7-dihydro-2-(4-methoxyphenyl)-3-bromomethyl-5-(oxazol-5-yl)-7-(2-fluorobenzyl)-4-oxothieno[2,3-b]pyridine A mixture of the compound produced in Example 1 (0.10 g, 0.22 mmol), N-bromosuccinimide (0.041 g, 0.24 mmol), α,α'-azobisisobutyronitrile (33 mg, 0.024 mmol), chloroform (5 ml) and carbon tetrachloride (40 ml) was refluxed under heating for one hours. After cooling resulting insolubles were filtered off from the reaction mixture. The filtrate was diluted with chloroform. The organic layer was washed with an aqueous sodium chloride solution and dried (MgSO$_4$), then the solvent was distilled off under reduced pressure. The residue was purified with silica gel chromatography to give pale yellowish solid form, and then it was recrystallized from chloroform-ethyl acetate-hexane to give yellow needles (0.08 g, 69%).

m.p. 234°–236° C.

$^1$H-NMR (300 MHz, CDCl$_3$) δ: 3.87(3H,s), 5.08(2H,s), 5.30(2H,s), 7.01(2H,d), 7.1–7.3(3H,m), 7.40(1H,m), 7.58 (2H,d), 7.84(1H,s), 8.10(2H,d).

EXAMPLE 3

Production of 3-(N-benzyl-N-methylaminomethyl)-4,7-dihydro-2-(4-methoxyphenyl)-5-(oxazol-5-yl)-7-(2-fluorobenzyl)-4-oxothieno[2,3-b]pyridine To a solution of the compound (0.07 g, 0.16 mmol) obtained in Example 2 in dimethylformamide (20 ml) are added under ice-cooling ethyldiisopropylamine (0.0243 g, 0.19 mmol) and N-benzylmethylamine (24.2 μl, 0.19 mmol).

After stirring for one hour at a room temperature, the reaction mixture was concentrated, and the residue was partitioned between ethyl acetate and saturated sodium bicarbonate. The aqueous layer was extracted with ethyl acetate and combined with the organic layer, and dried ($MgSO_4$).

After removing off the solvent, the residue was purified with silica gel column chromatography to give colorless powder (0.52 g, 67%). The powder was recrystallized with ethyl acetate-hexane-dichloromethane to give white crystals (0.022 g, 28%).

m.p. 144°–150° C.

Elemental Analysis for $C_{33}H_{28}N_3O_3SF.3H_2O$: C(%) H(%) N(%) Calcd.: 63.96; 5.53; 6.78 Found: 63.82; 4.74; 6.98

$^1$H-NMR (300 MHz, $CDCl_3$) δ: 2.76(3H,br), 3.88(3H,s), 4.42(2H,br), 4.62(2H,br), 5.49(2H,s), 7.05(2H,d), 7.1–7.5 (11H,m), 7.90(1H,s), 8.01(1H,s), 8.39(1H,s).

FAB-MS m/z: 566 (MH$^+$).

EXAMPLE 4

Production of 4,7-dihydro-2-phenyl-3-methyl-5-acetylamino-7-(2,6-difluorobenzyl)-4-oxothieno[2,3-b]pyridine To a solution of O-methyl-N-methylhydroxylamine hydrochloride(25.3 g, 259.0 mmol) and diisopropylethylamine(33.5 g, 259.0 mmol) in anhydrous methylene chloride (400 ml) was added dropwise at 0° C. a hexane solution (15%, 83.0 ml, 129.7 mmol) of trimethyl aluminum in hexane. The mixture was allowed to warm to room temperature and stirred for further one hour. To this solution was added, with ice-cooling (0° C.), a solution of the compound produced in Reference Example 9 (2) (28.5 g, 64.8 mmol) in anhydrous methylene chloride (200 ml), over a period of 30 minutes. The mixture was stirred for further one hour at room temperature, to which was added chloroform (200 ml), and the mixture was washed with water. The combined organic layer was dried over sodium sulfate, which was concentrated to give a solid. The solid was recrystallized from chloroform-ethyl acetate-ethyl ether to give a compound which is N-methyl-O-hydroxamic acid at 5-position.

Thus obtained compound (27.4 g, 60.4 mmol) was dissolved in anhydrous tetrahydrofuran (THF) (500 ml) under mild heating. To this solution was added dropwise, while keeping at 0° C., a solution of methyl magnesium chloride in THF (3M, 30.2 ml, 90.5 mmol), over a period of 10 minutes. The mixture was stirred for further one hour. The reaction mixture was partitioned between ethyl acetate (300 ml) and water (300 ml). The aqueous layer was again extracted with ethyl acetate. The combined organic layer was dried over magnesium sulfate, which was concentrated under reduced pressure. The concentrate was chromatographed on silica gel and further was recrystallized from ethyl acetate - hexane, to give 4,7-dihydro-2-phenyl-3-methyl-5-acetyl-7-(2,6-difluorobenzyl)-4-oxothieno[2,3-b]pyridine.

In pyridine (40 ml) is dissolved 4,7-dihydro-2-phenyl-3-methyl-5-acetyl-7-(2,6-difluorobenzyl)-4-oxothieno[2,3-b]pyridine (3.66 mg, 0.89 mmol), and hydroxylamine hydrochloride (68 mg, 1.0 mmol). The mixture was stirred for 1 hour at 60° C. The reaction mixture was concentrated to dryness, and the residue obtained was partitioned between chloroform (100 ml) and water. Water layer was extracted with chloroform (100 ml) and the extracts were combined and washed with an aqueous solution of sodium chloride, dried with $Na_2SO_4$, and the solvent was removed off under reduced pressure.

Thus obtained residue was purified with silica gel chromatography to give a solid form (390 mg). Recrystallization from chloroform-ether gave white crystals (308 mg, 82%). The obtained crystals (150 mg) was dissolved in pyridine (5 ml), and to the solution was added dropwise p-toluensulfonic acid chloride (74 mg, 0.39 mmol), and the mixture was stirred for one hour at room temperature. The reaction mixture was concentrated and dried, and the residue obtained was partitioned between chloroform (100 ml) and water. The aqueous layer was extracted with chloroform (100 ml), and the extracts were combined, washed with an aqueous solution of sodium chloride, and dried with $Na_2SO_4$, and the solvent was removed off under reduced pressure. The residue obtained was purified with silica gel column chromatography to give amorphous product (46 mg).

mass m/z 425($M^{+1}$)

$^1$H-NMR ($CDCl_3$) δ: 2.20(3H,s), 2.70(3H,s), 5.23(2H,s), 6.99(2H,t), 7.3–7.5(6H,m), 8.53(1H,s), 9.11(1H,s).

EXAMPLE 5

Production of 4,7-dihydro-2-phenyl-3-methyl-5-amino-7-(2,6-difluorobenzyl)-4-oxothieno[2,3-b]pyridine The compound obtained in Example 4 was dissolved in ethanol, and to the solution was added an excess amount of an aqueous 2N sodium hydroxide solution. The mixture was subjected to alkali hydrolysis under heating for 24 hours to give the titled compound.

mass m/z 383($M^{+1}$)

$^1$H-NMR ($CDCl_3$) δ: 2.71(3H,s), 3.3–4.3(2H,brs), 5.14 (2H,s), 6.98(2H,t), 7.17(1H,s), 7.3–7.5(6H,m).

EXAMPLE 6

Production of 4,7-dihydro-2-(4-nitrophenyl)-3-methyl-5-acetoxy-7-(2,6-difluorobenzyl)-4-oxothieno[2,3-b]pyridine 4,7-dihydro-2-phenyl-3-methyl-5-acetyl-7-(2,6-difluorobenzyl)-4-oxothieno[2,3-b]pyridine (500 mg, 1.1 mmol), which was obtained in the manner described in the above Example 4, was dissolved in dichloromethane (50 ml). To the solution was added m-chloroperbenzoic acid (570 mg, 1.65 mmol), and the mixture was stirred for 1.5 hours. After cooling, the reaction mixture was partitioned between dichloromethane (100 ml) and an aqueous solution of sodium bicarbonate. The aqueous layer was extracted with dichloromethane (100 ml), and the extracts were combined, washed with an aqueous sodium chloride solution, dried ($Na_2SO_4$) and the solvent was removed off under reduced pressure. Thus obtained residue was purified by silica gel column chromatography, recrystallized with chloroform-ether to give pale yellowish crystals (347 mg, 67%).

m.p. 216°–217° C.

EXAMPLE 7

Production of 4,7-dihydro-2-(4-nitrophenyl)-3-methyl-5-isopropoxy-7-(2,6-difluorobenzyl)-4-oxothieno[2,3-b]pyridine The compound (2.16 g, 4.75 mmol) obtained in Example 6 was dissolved in tetrahydrofuran (100 ml). To the solution was added 1N sodium hydroxide (12 ml), and the mixture was stirred for one hour at room temperature. The reaction mixture was concentrated to dryness, and the residue obtained was partitioned between dichloromethane (200 ml) and water. The aqueous layer was extracted with dichloromethane (200 ml), the extracts were combined, washed with an aqueous sodium chloride solution, dried with $Na_2SO_4$, and the solvent was removed off under reduced pressure. The obtained residue was purified by silica gel column chromatography to give amorphous product (1.80 g).

The compound (1.41 g, 3.29 mmol) obtained in the above was dissolved in dimethylformamide (40 ml). To the solution was added isopropyl iodide (2.02 g, 16.46 mmol) and potassium carbonate (2.27 g, 16.46 mmol), and the mixture was stirred for 24 hours at 50° C. The reaction mixture was concentrated to dryness, and the residue was partitioned between chloroform (300 ml) and water. The aqueous layer was extracted with chloroform (300 ml) and the extracts were combined, washed with an aqueous sodium chloride solution, dried with $Na_2SO_4$, and the solvent was removed off under reduced pressure. The obtained residue was purified by silica gel column chromatography and recrystallized from chloroform-ether-n-hexane to give pale yellow crystals (550 mg, 36%).

m.p. 188°–189° C.

Mass m/z 471($M^+$)

$^1$H-NMR ($CDCl_3$) δ: 1.30(6H,d), 2.75(3H,s), 4.67(1H,m), 5.18(2H,s), 7.01(2H,t), 7.3–7.5(2H,m), 7.61(2H,d), 8.29 (2H,d).

EXAMPLE 8

(1) Using the compound obtained in Example 7 and by a similar manner as in Example 2, the following compound was produced.

4,7-dihydro-2-(4-nitrophenyl)-3-bromomethyl-5-isopropoxy-7-(2,6-difluorobenzyl)-4-oxothieno[2,3-b]pyridine.

Yellow amorphous.

$^1$H-NMR ($CDCl_3$) δ: 1.31(6H,d), 4.68(1H,m), 5.04(2H,s), 5.27(2H,s), 7.03(2H,t), 7.4–7.5(2H,m), 7.85(2H,d), 8.33 (2H,d).

(2) The compound obtained in Example 8(1) was used and by a similar manner as in Example 3, the following compound was produced.

4,7-dihydro-2-(4-nitrophenyl)-3-(N-benzyl-N-methylaminomethyl)-5-isopropoxy-7-(2,6-difluorobenzyl)-4-oxothieno[2,3-b]pyridine.

Yellow amorphous.

$^1$H-NMR ($CDCl_3$) δ: 1.33(6H,d), 2.23(3H,s), 3.70(2H,s), 4.23(2H,s), 4.64(1H,m), 5.22(2H,s), 7.01(2H,t), 7.1–7.5(7H, m), 8.11(2H,d), 8.23(2H,d).

(3) The compound obtained in Example 8(2) was used and by a similar manner as in Example 20 below mentioned, the following compound was produced.

4,7-dihydro-2-(4-aminophenyl)-3-(N-benzyl-N-methylaminomethyl)-5-isopropoxy-7-(2,6-difluorobenzyl)-4-oxothieno[2,3-b]pyridine.

Colorless amorphous.

$^1$H-NMR ($CDCl_3$) δ: 1.30(6H,d), 2.18(3H,s), 3.70(2H,s), 3.92(2H,brs), 4.18(2H,s), 5.16(2H,s), 6.70(2H,d), 6.95(2H, t), 7.1–7.5(7H,m), 7.60(2H,d).

(4) The compound obtained in Example 8(3) was used and by a similar manner as in Example 21 below mentioned, the following compound was produced.

4,7-dihydro-2-(4-isobutyrylaminophenyl)-3-(N-benzyl-N-methylaminomethyl)-5-isopropoxy-7-(2,6-difluorobenzyl)-4-oxothieno[2,3-b]pyridine.

Yellow amorphous.

$^1$H-NMR ($CDCl_3$) δ: 1.21(6H,d), 1.35(6H,d), 2.42(3H,s), 2.95(1H,m), 3.73(2H,s), 4.25(2H,s), 4.63(1H,m), 5.35(2H, s), 6.99(2H,t), 7.2–7.5(8H,m), 7.69(1H,s), 7.95(2H,d), 9.82 (1H, brs).

EXAMPLE 9

Production of 4,7-dihydro-2-(4-isobutyrylaminophenyl)-3-(N-benzyl-N-methylaminomethyl)-5-hydroxy-7-(2,6-difluorobenzyl)-4-oxothieno[2,3-b]pyridine The compound (360 mg, 0.57 mmol) obtained in Example 8(4) was dissolved in dichloromethane (25 ml). To the solution a solution of boron trichloride (1.0M) in dichloromethane (2.29 ml) was added, and the mixture was stirred for 1.5 hours under ice-cooling (0° C.). To the reaction mixture was added water, and the solution was partitioned between chloroform (100 ml) and an aqueous sodium bicarbonate solution. The aqueous layer was extracted with chloroform (100 ml), the extracts were combined, washed with an aqueous sodium chloride solution, dried with $Na_2SO_4$, and the solvent was removed off under reduced pressure:

Thus obtained residue was purified by silica gel column chromatography to give pale red amorphous (210 mg, 63%).

$^1$H-NMR ($CDCl_3$) δ: 1.25(6H,d), 2.12(3H,s), 2.60(1H,m), 3.63(2H,s), 4.14(2H,s), 5.17(2H,s), 6.98(2H,t), 7.1–7.3(5H, m), 7.3–7.5(2H,m), 7.5–7.9(5H,m).

EXAMPLE 10

Production of 4,7-dihydro-2-(4-isobutyrylaminophenyl)-3-(N-benzyl-N-methylaminomethyl)-5-isopropylsulfonyloxy-7-(2,6-difluorobenzyl)-4-oxothieno[2,3-b]pyridine hydrochloride The compound (50 mg) obtained in Example 9 was dissolved in dichloromethane (5 ml). To the solution were added dropwise isopropylsulfonyl chloride (31 mg, 0.27 mmol) and triethylamine (17 mg, 0.17 mmol) under ice-cooling. After the addition, the mixture was stirred for one hour. The reaction mixture was concentrated to dryness, and the residue was partitioned between dichloromethane (50 ml) and water.

The aqueous layer was extracted with dichloromethane (50 ml), and the extracts were combined, washed with an aqueous sodium chloride solution, dried with $Na_2SO_4$, and the solvent was removed off under reduced pressure. The residue was purified by silica gel column chromatography to give amorphous product (30 mg, 51%).

In a similar manner as in Example 22 mentioned below, a hydrochloride of the titled compound was obtained as white crystals (13 g, 41%).

Hydrochloride:

m.p. 172–177° C.

mass m/z 694($M^{+1}$).

$^1$H-NMR ($CDCl_3$) δ: 1.13(6H,d), 1.55(6H,dd), 2.55(3H, d), 2.67(1H,m), 4.01(1H,m), 4.2–4.5(3H,m), 4.60(1H,dd), 5.70(2H,s), 7.24(2H,t), 7.3–7.5(7H,m), 7.56(1H,m), 7.83 (2H,d), 8.86(1H,s), 10.26(1H,s), 10.81(1H,brs).

EXAMPLE 11

Production of 4,7-dihydro-2-(4-isobutyrylaminophenyl)-3-(N-benzyl-N-methylaminomethyl)-5-isobutyryloxy-7-(2,6-difluorobenzyl)-4-oxothieno[2,3-b]pyridine hydrochloride The compound obtained in Example 9 was subjected to a similar procedure as in Example 10, using isobutyryl chloride instead of isopropyl chloride, and the titled compound was obtained.

m.p. 169°–172° C.

mass m/z 658($M^{+1}$)

$^1$H-NMR (CDCl$_3$) δ: 1.16(6H,d), 1.30(6H,dd), 2.59(3H, d), 2.64(1H,m), 2.90(1H,m), 4.06(1H,m), 4.3–4.6(3H,m), 5.65(2H,s), 7.2–7.5(9H,m), 7.57(1H,m), 7.85(2H,d), 8.66 (1H,s), 10.23(1H,s), 11.70(1H,brs).

EXAMPLE 12

Production of 4,7-dihydro-2-(4-isobutyrylaminophenyl)-3-(N-benzyl-N-methylaminomethyl)-5-ethoxycarbonylmethoxy-7-(2,6-difluorobenzyl)-4-oxothieno[2,3-b]pyridine and its hydrochloride The compound obtained in Example 9 was subjected to a similar procedure as in Example 7, using ethyl acetate bromide instead of isobutyryl chloride, the titled compound and its hydrochloride were obtained.

Free form.

$^1$H-NMR (CDCl$_3$) δ: 1.2–1.3(9H,m), 2.20(3H,s), 2.83 (1H,brs), 3.74(2H,s), 4.1–4.2(4H,m), 4.82(2H,s), 5.22(2H, s), 6.97(2H,t), 7.0–7.3(7H,m), 7.39(1H,m), 7.58(1H,brs), 7.83(2H,brs).

Hydrochloride:

m.p. 190°–194° C.

mass m/z 674($M^{+1}$)

$^1$H-NMR (DMSO-d$_6$) δ: 1.12(6H,d), 1.23(3H,t), 2.61(3H, d), 2.67(1H,m), 4.18(2H,q), 4.2–4.6(4H,m), 4.87(2H,s), 5.62(2H,s), 7.3–7.5(9H,m), 7.56(1H,m), 7.83(2H,d), 8.37 (1H,s), 10.28(1H,s), 11.87(1H,brs).

EXAMPLE 13

Production of 4,7-dihydro-2-(4-isobutyrylaminophenyl)-3-(N-benzyl-N-methylaminomethyl)-5-carbamoylmethoxy-7-(2,6-difluorobenzyl)-4-oxothieno[2,3-b]pyridine The free form (87 mg, 0.17 mmol) obtained in Example 12 was dissolved in 3 ml of ethanol, and to the solution was added 8.6M ammonium-ethanol (2 ml). The mixture was stirred for 16 hours, and the reaction mixture was concentrated to dryness. The resultant was purified by silica gel column chromatography, and recrystallized from chloroform-ether to give white crystals.

m.p. 237°–238° C.

mass m/z 645($M^{+1}$)

$^1$H-NMR (CDCl$_3$) δ: 1.28(6H,d), 2.11(3H,s), 2.56(1H,m), 3.65(2H,s), 4.14(2H,s), 4.47(2H,s), 5.21(2H,s), 5.58(1H, brs), 7.01(2H,t), 7.1–7.3(6H,m), 7.4–7.5(2H,m), 7.62(2H,d), 7.78(2H,d), 8.78(1H,brs).

EXAMPLE 14

Production of 4,7-dihydro-2-phenyl-3-methyl-5-isopropylthio-7-(2,6-difluorobenzyl)-4-oxothieno[2,3-b]pyridine To a solution of compound (6.0 g, 19 mmol) obtained in Reference Example 15 in dimethylformamide (250 ml) were added potassium carbonate (2.89 g, 21 mmol mmol), 2,6-difluorobenzyl chloride (3.40 g, 21 mmol) and potassium iodide (0.79 g) at room temperature.

The reaction mixture was concentrated to dryness, and the residue was partitioned between chloroform (500 ml) and water. The aqueous layer was extracted with chloroform (200 ml), the extracts were combined, washed with an aqueous sodium chloride solution, dried with Na$_2$SO$_4$, and the solvent was distilled off under reduced pressure.

Thus obtained residue was purified by silica gel column chromatography to obtain colorless amorphous product (10.7 g, 48%), and recrystallized from dichloromethane-n-hexane to give pale yellow crystals.

m.p. 129°–131° C.

Elemental Analysis for C$_{24}$H$_{21}$NOS$_2$F$_2$.0.3H$_2$O: C(%) H(%) N(%) Calcd.: 64.49; 4.87; 3.13 Found: 64.53; 4.79; 3.18 mass m/z 442($M^{+1}$)

$^1$H-NMR (CDCl$_3$) δ: 1.24(6H,d,J=6.6 Hz), 2.67(3H,s), 3.61–3.70(1H,m), 5.20(2H,s), 6.98(2H,t,J=8.04 Hz), 7.33–7.43(6H,m), 7.86(1H,s).

EXAMPLE 15

Production of 4,7-dihydro-2-phenyl-3-methyl-5-isopropylsulfinyl-7-(2,6-difluorobenzyl)-4-oxothieno[2,3-b]pyridine The compound (2.20 g, 50 mmol) obtained in Example 14 was dissolved in dichloromethane (200 ml). To the solution was added dropwise m-chloroperbenzoic acid (0.99 g, 21 mmol) in dichloromethane (200 ml) for one hour under ice-cooling. After the addition, the mixture was stirred for 10 minutes, and the reaction mixture was partitioned between chloroform (300 ml) and saturated sodium bicarbonate. The aqueous layer was extracted with chloroform (100 ml), the extracts were combined, washed with an aqueous sodium chloride solution, dried with Na$_2$SO$_4$, and the solvent was distilled off under reduced pressure.

Thus obtained residue was purified by silica gel column chromatography to give colorless amorphous product (2.16 g, 85%), and recrystallized from dichloromethane-ether-n-hexane to give pale yellow crystals.

m.p. 217°–219° C.

Elemental Analysis for C$_{24}$H$_{21}$NO$_2$S$_2$F$_2$.0.2H$_2$O: C(%) H(%) N(%) Calcd.: 62.51; 4.68; 3.04 Found: 62.48; 4.57; 3.02

Mass m/z 458($M^{+1}$)

$^1$H-NMR (CDCl$_3$) δ: 1.04(6H,d,J=6.8 Hz), 2.63(3H,s), 3.44–3.60(1H,m), 5.29–5.41(2H,Abq,J=15.3 Hz), 6.94–7.48 (8H,m), 7.87(1H,d,J=1.44 Hz).

EXAMPLE 16

Production of 4,7-dihydro-2-phenyl-3-methyl-5-isopropylsulfonyl-7-(2,6-difluorobenzyl)-4-oxothieno[2,3-b]pyridine In Example 15, the titled compound was obtained as pale yellow crystals (0.1 g, 8%) as a by-product.

m.p. 231°–233° C.

Elemental Analysis for C$_{24}$H$_{21}$NO$_2$S$_2$F$_2$.0.2H$_2$O: C(%) H(%) N(%) Calcd.: 60.87; 4.47; 2.96 Found: 61.16; 4.33; 3.07

Mass m/z 474($M^{+1}$)

$^1$H-NMR (CDCl$_3$) δ: 1.36(6H,d,J=6.8 Hz), 2.64(3H,s), 4.07–4.16(1H,m), 5.33(2H,s), 7.00(2H,t,J=8.1 Hz), 7.37–7.45(6H,m), 8.37(1H,s).

EXAMPLE 17

Production of 4,7-dihydro-2-(4-nitrophenyl)-3-methyl-5-isopropylsulfinyl-7-(2,6-difluorobenzyl)-4-oxothieno[2,3-b]pyridine To a solution of the compound (915 mg, 2 mmol) obtained in Example 15 in conc. sulfuric acid (12 ml) was added dropwise a sodium nitrate solution in conc. sulfuric acid (4 ml) under ice-cooling for 30 minutes. The mixture was stirred for 3 hours, and the reaction mixture was partitioned between chloroform (300 ml) and ice-water. The aqueous layer was extracted with chloroform (100 ml), the extracts were combined, washed with an aqueous sodium chloride solution, dried with $Na_2SO_4$, and the solvent was distilled off. Thus obtained residue was recrystallized from dichloromethane-ether-n-hexane to give yellow crystals (1.03 g, 100%).

m.p. 212°–214° C.

Elemental Analysis for $C_{24}H_{20}N_2O_4S_2F_2 \cdot 0.2H_2O$: C(%) H(%) N(%) Calcd.: 56.95; 4.06; 5.53 Found: 56.91; 4.03; 5.47

Mass m/z 503($M^{+1}$)

$^1$H-NMR (CDCl$_3$) δ: 1.04(6H,d,J=6.9 Hz), 1.51(3H,d,J=7.1 Hz), 2.68(3H,s), 3.47–3.56(1H,m), 5.31–5.43(2H,Abq, J=15.0 Hz), 7.01(2H,t,J=8.1 Hz), 7.37–7.47(1H,m), 7.58–8.32(4H,Abq,J=8.7 Hz), 7.90(1H,s).

EXAMPLE 18

Production of 4,7-dihydro-2-(4-nitrophenyl)-3-bromomethyl-5-isopropylsulfinyl-7-(2,6-difluorobenzyl)-4-oxothieno[2,3-b]pyridine The compound (980 mg, 2 mmol) obtained in Example 17, N-bromosuccinimide (NBS) (0.36 g, 2.04 mmol) and α,α-azobisisobutyronitrile (AIBN) (60 mg, 0.37 mmol) were suspended in carbon tetrachloride (250 ml). The mixture was refluxed under heating for 3 hours. After cooling, the reaction mixture was partitioned between chloroform (300 ml) and an aqueous sodium bicarbonate solution. The aqueous layer was extracted with chloroform (100 ml), the extracts were combined, washed with an aqueous sodium chloride solution, dried with $Na_2SO_4$, and the solvent was distilled off. Thus obtained residue was recrystallized from dichloromethane-n-hexane to give yellow crystals (1.09 g, 96%).

m.p. 176°–181° C.

Elemental Analysis for $C_{24}H_{19}N_2O_4S_2F_2Br \cdot 0.4H_2O$: C(%) H(%) N(%) Calcd.: 49.58; 3.39; 4.76 Found: 49.09; 3.36; 4.79

Mass m/z 581, 583 ($M^{+1}$)

$^1$H-NMR (CDCl$_3$) δ: 1.05(6H,d,J=6.6 Hz), 1.51(3H,d,J=7.1 Hz), 3.50–3.60(1H,m), 4.88–4.99(2H,Abq,J=9.6 Hz), 5.38(2H,s), 7.02(2H,t,J=8.1 Hz), 7.39–7.49(1H,m), 7.81–8.38(4H,Abq,J=8.5 Hz), 7.95(1H,s).

EXAMPLE 19

Production of 4,7-dihydro-2-(4-nitrophenyl)-3-(N-benzyl-N-methylaminomethyl)-5-isopropylsulfinyl-7-(2,6-difluorobenzyl)-4-oxothieno[2,3-b]pyridine The compound (1.04 g, 1.8 mmol) obtained in Example 18 was dissolved in dimethylformamide (70 ml). To the solution was added diisopropylaminoethyl (1.15 g, 8.9 mmol) and N-methylbenzylamine (0.54 g, 4.5 mmol) at room temperature, and the mixture was further stirred for one hour. The reaction mixture was concentrated to dryness, and the residue was partitioned between ethyl acetate (300 ml) and water. The aqueous layer was extracted with ethyl acetate (100 ml), the extracts were combined, washed with an aqueous sodium chloride solution, dried with $Na_2SO_4$, and the solvent was distilled off. Thus obtained residue was purified by silica gel column chromatography to give a solid form (1.09 g), and recrystallization from dichloromethane-ether-n-hexane gave pale yellow crystals (1.03 g, 93%).

m.p. 98°–103° C.

Elemental Analysis for $C_{32}H_{29}N_3O_4S_2F_2 \cdot 0.8H_2O$: C(%) H(%) N(%) Calcd.: 60.42; 4.85; 6.61 Found: 60.40; 4.70; 6.71

Mass m/z 622.2($M^{+1}$)

$^1$H-NMR (CDCl$_3$) δ: 1.04(6H,d,J=6.8 Hz), 1.52(3H,d,J=7.Hz), 2.19(3H,s), 3.47–3.56(1H,m), 3.63(2H,s), 4.01–4.25 (2H,Abq,J=11.9 Hz), 5.32–5.43(2H,Abq,J=15.3 Hz), 7.02 (2H,t,J=8.8 Hz), 7.13–7.48(6H,m), 7.90(1H,s), 8.06–8.28 (4H,Abq,J=8.8 Hz).

EXAMPLE 20

Production of 4,7-dihydro-2-(4-aminophenyl)-3-(N-benzyl-N-methylaminomethyl)-5-isopropylsulfinyl-7-(2,6-difluorobenzyl)-4-oxothieno[2,3-b]pyridine The compound (0.54 g, 0.87 mmol) obtained in Example 19 and iron powder (0.26 g, 4.3 mmol) were added to methanol (10 ml) and to the mixture conc. hydrogen chloride (5 ml) was added dropwise for one hour. The mixture was stirred for 5 hours under ice-cooling. To the reaction mixture saturated sodium bicarbonate (30 ml) was added carefully. After adding chloroform (50 ml) and Celite, the mixture was subjected to filtration.

The aqueous layer was extracted with chloroform (100 ml), the extracts were combined, washed with an aqueous sodium chloride solution, dried with $Na_2SO_4$, and the solvent was distilled off. Thus obtained residue was recrystallized from dichloromethane-n-hexane to give pale yellow crystals (0.46 g, 89%).

m.p. 105°–115° C.

Elemental Analysis for $C_{32}H_{31}N_3O_2S_2F_2 \cdot 0.5H_2O$: C(%) H(%) N(%) Calcd.: 63.98; 5.37; 6.99 Found: 64.09; 5.50; 6.82

Mass m/z 592($M^{+1}$)

$^1$H-NMR (CDCl$_3$) δ: 1.03(6H,d,J=6.8 Hz), 1.50(3H,d,J=7.1 Hz), 2.11(3H,s), 3.48–3.58(1H,m), 3.61(2H,s), 3.87(2H, brs), 3.96–4.18(2H,Abq,J=12 Hz), 5.28–5.39(2H,Abq,J=15.3 Hz), 6.71–7.63(4H,Abq,J=8.7 Hz), 6.98(2H,t,J=8.1 Hz), 7.12–7.44(6H,m), 7.85(1H,s).

EXAMPLE 21

Production of 4,7-dihydro-2-(4-isobutyrylaminophenyl)-3-(N-benzyl-N-methylaminomethyl)-5-isopropylsulfinyl-7-(2,6-difluorobenzyl)-4-oxothieno[2,3-b]pyridine To a solution of the compound (0.41 mg, 0.69 mmol) obtained in example 20 in dichloromethane (20 ml) were added triethylamine (0.70 g, 7.0 mmol) and isobutyryl chloride (0.36 g, 3.5 mmol) under ice-cooling. The mixture was stirred for one hour under ice-cooling. To the reaction mixture was added a saturated aqueous sodium bicarbonate solution (30 ml), and the mixture was extracted with chloroform (20 ml). The extracted aqueous layer was further extracted with chloroform (20 ml), the extracts were combined, washed with an aqueous sodium chloride solution, dried with Na$_2$SO$_4$, and the solvent was distilled off. Thus obtained residue was purified by silica gel column chromatography to give amorphous product (0.35 g, 77%).

$^1$H-NMR (CDCl$_3$) δ: 1.04(6H,d,J=6.8 Hz), 1.27(3H,d,J=6.8 Hz), 1.51(3H,d,J=7.1 Hz), 2.16(3H,s), 2.07–2.67(1H,m), 3.48–3.60(1H,m), 3.68(2H,s), 4.02–4.22(2H,Abq,J=12 Hz), 5.31–5.42(2H,Abq,J=15.0 Hz), 6.99(2H,t,J=8.1 Hz), 7.14–7.45(6H,m), 7.68–7.75(4H,m), 7.86(1H,s), 7.93(1H,s).

EXAMPLE 22

Production of 4,7-dihydro-2-(4-isobutyrylaminophenyl)-3-(N-benzyl-N-methylaminomethyl)-5-isopropylsulfinyl-7-(2,6-difluorobenzyl)-4-oxothieno[2,3-b]pyridine hydrochloride The compound (0.35 g, 0.53 mmol) obtained in Example 21 was dissolved in dichloromethane (5 ml). To the solution was added 1M hydrogen chloride in ether (1.06 ml, 1.06 mmol) under ice-cooling. The mixture was stirred for 30 minutes, the solvent was distilled off under reduced pressure. Thus obtained residue was recrystallized from dichloromethane-n-hexane to give pale yellow crystals (0.30 g, 77%).

m.p. 185°–187° C.

Elemental Analysis for C$_{36}$H$_{37}$N$_3$O$_4$S$_2$F$_2$·HCl·2H$_2$O: C(%) H(%) N(%) Calcd.: 58.88; 5.76; 5.72 Found: 59.08; 5.74; 5.78

Mass m/z 662(M$^{+1}$) $^1$H-NMR (CDCl$_3$) δ: 0.98–1.46(6H, m), 1.13(6H,d,J=6.3 Hz), 2.64–2.73(1H,m), 2.67(3H,d,J=4.6 Hz), 3.33–3.43(1H,m), 4.20–4.60(4H,m), 5.69–5.96(2H, m), 7.21–7.871(12H,m), 8.37(1H,s), 10.29(1H,s), 10.78 (0.5H,s), 10.88(0.5H,s).

EXAMPLE 23

The compound obtained in Example 16 is subjected to the reactions similar to those described in Examples 17, 18, 19, 20, 21 or 22, or the compound obtained in Examples 22 is subjected to the reactions similar to those described in Examples 15 or 16, the following compound is produced: 4,7-dihydro-2-(4-isobutyrylaminophenyl)-3-(N-benzyl-N-methylaminomethyl)-5-isopropylsulfonyl-7-(2,6-difluorobenzyl)-4-oxothieno[2,3-b]pyridine.

The compounds shown in the above Examples are listed in the following tables 1 to 3.

TABLE 1

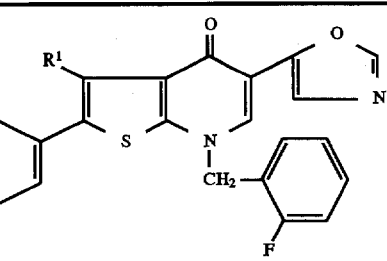

| Example No. | R$^1$ (3-position) |
|---|---|
| 1 | methyl |
| 2 | bromomethyl |
| 3 | N-benzyl-N-methylaminomethyl |

TABLE 2

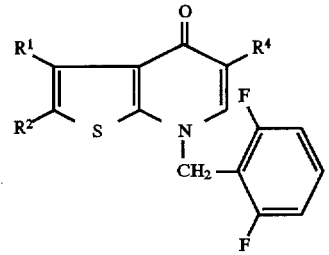

| Example No. | R$^1$ (3-position) | R$^2$ (2-position) | R$^4$ (5-position) |
|---|---|---|---|
| 4 | methyl | phenyl | acetylamino |
| 5 | methyl | phenyl | amino |
| 6 | methyl | 4-nitrophenyl | acetoxy |
| 7 | methyl | 4-nitrophenyl | isopropoxy |
| 8(1) | bromomethyl | 4-nitrophenyl | isopropoxy |
| 8(2) | N-benzyl-N-methylaminomethyl | 4-nitrophenyl | isopropoxy |
| 8(3) | N-benzyl-N-methylaminomethyl | 4-aminophenyl | isopropoxy |
| 8(4) | N-benzyl-N-methylaminomethyl | 4-isobutyryl-aminophenyl | isopropoxy |
| 9 | N-benzyl-N-methylaminomethyl | 4-isobutyryl-aminophenyl | hydroxy |
| 10 | N-benzyl-N-methylaminomethyl | 4-isobutyryl-aminophenyl | isopropyl-sulfonyloxy |
| 11 | N-benzyl-N-methylaminomethyl | 4-isobutyryl-aminophenyl | isobutyryloxy |
| 12 | N-benzyl-N-methylaminomethyl | 4-isobutyryl-aminophenyl | ethoxycarbonyl-methoxy |
| 13 | N-benzyl-N-methylaminomethyl | 4-isobutyryl-aminophenyl | carbamoyl-methoxy |
| 14 | methyl | phenyl | isopropylthio |
| 15 | methyl | phenyl | isopropyl-sulfinyl |

TABLE 3

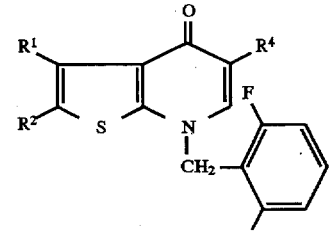

| Example No. | R$^1$ | R$^2$ | R$^4$ |
|---|---|---|---|
| 16 | methyl | phenyl | isopropylsulfonyl |
| 17 | methyl | 4-nitrophenyl | isopropylsulfinyl |
| 18 | bromomethyl | 4-nitrophenyl | isopropylsulfinyl |
| 19 | N-benzyl-N-methylaminomethyl | 4-nitrophenyl | isopropylsulfinyl |
| 20 | N-benzyl-N-methylaminomethyl | 4-aminophenyl | isopropylsulfinyl |
| 21 | N-benzyl-N-methylaminomethyl | 4-isobutyryl-aminophenyl | isopropylsulfinyl |
| 22 | N-benzyl-N-methylaminomethyl | 4-isobutyryl-aminophenyl | isopropylsulfinyl |
| 23 | N-benzyl-N-methylaminomethyl | 4-isobutyryl-aminophenyl | isopropylsulfonyl |

EXAMPLE 24

Using the compound produced in Example 3, lactose (165 mg), cornstarch (25 mg), polyvinyl alcohol (4 mg) and magnesium stearate (1 mg), tablets are prepared by a conventional method.

EXAMPLE 25

The compound produced in Example 3 is dissolved in distilled water for injection to make the whole volume 100 ml. This solution is subjected to sterilized filtration through 0.22 μm membrane filter (manufactured by Sumitomo Electric Industries, Ltd. or Zartolius Inc.), 2 ml each of which is divided into sterilized vials, followed by lyophilization to prepare a lyophilized injectable composition of 100 mg/vial.

EXAMPLE 26

The compound produced in Example, lactose (165 mg), cornstarch (25 mg), polyvinyl alcohol (4 mg) and magnesium stearate (1 mg), tablets are prepared by a conventional method.

EXAMPLE 27

The compound produced in Example 8(4) is dissolved in distilled water for injection to make the whole volume 100 ml. This solution is subjected to sterilized filtration through 0.22 μm membrane filter (manufactured by Sumitomo Electric Industries, Ltd, or Zartolius Inc.), 2 ml each of which is divided into sterilized vials, followed by lyophilization to prepare a lyophilized injectable composition of 100 mg/vial.

EXAMPLE 28

The compound produced in Example 10, lactose (165 mg), cornstarch (25 mg), polyvinyl alcohol (4 mg) and magnesium stearate (1 mg), tablets are prepared by a conventional method.

EXAMPLE 29

The compound produced in Example 10 is dissolved in distilled water for injection to make the whole volume 100 ml. This solution is subjected to sterilized filtration through 0.22 μm membrane filter (manufactured by Sumitomo Electric Industries, Ltd. or Zartolius Inc.), 2 ml each of which is divided into sterilized vials, followed by lyophilization to prepare a lyophilized injectable composition of 100 mg/vial.

EXAMPLE 30

| | | |
|---|---|---|
| (1) Compound produced in Example 3 | 5 g |
| (2) Lactose.crystalline cellulose (granules) | 330 g |
| (3) D-mannitol | 29 g |
| (4) Low-substituted hydroxypropyl cellulose | 20 g |
| (5) Talc | 25 g |
| (6) Hydroxypropyl cellulose | 50 g |
| (7) Aspartame | 3 g |
| (8) Dipotassium glycyrrhetinate | 3 g |
| (9) Hydroxypropylmethyl cellulose 2910 | 30 g |
| (10) Titanium oxide | 3.5 g |
| (11) Yellow iron sesquioxide | 0.5 g |
| (12) Light silicic acid anhydride | 1 g |

In refined water are suspended or dissolved (1), (3), (4), (5), (7) and (8). The nuclear granule of (2) is coated with the suspension or solution to prepare raw fine granules, which are coated with (9)–(11) to prepare coated fine granules, which are mixed with (12), to give 500 g of fine granules containing 1% of the compound produced in Example 3. 500 mg each of thus-prepared fine granules is packed.

TEST EXAMPLE 1

(1) Preparation of $^{125}$I-leuprorelin

Ten μl of a 3×10$^{-4}$M aqueous solution of leuprorelin and 10 μl of 0.01 mg/ml lactoperoxidase in 0.1M HEPES buffer (pH 7.4) were taken into a tube, to which was added 10 μl [37MBq in 0.1M HEPES buffer (pH 7.4)] of an Na$^{125}$I solution. The mixture was stirred, to which was added 10 μl of 0.001% H$_2$O$_2$, then reaction was allowed to proceed for 20 minutes at room temperature. To the reaction mixture was added 700 μl of a 0.05% TFA solution to stop the reaction. The product was purified by means of reversed phase HPLC. Conditions of HPLC are as follows. $^{125}$I-leuprorelin was eluted at a retention time of 26 to 27 minutes.

Column: TSK gel ODS-80 ™CTR (4.6 mm×10 cm)
Eluent: Solvent A (0.05% TFA)
Solvent B (40%CH$_3$CN-0.05% TFA)
0 minute (100% Solvent A)–3 minutes (100% Solvent A)–7 minutes (50% Solvent A+50% Solvent B)–40 minutes (100% Solvent B) Elution temp.: room temperature Flow rate: 1 ml/min. (2) Preparation of membrane fraction of CHO (Chinese Hamster Ovary) cells containing human GnRH receptors CHO cells (10$^9$) expressing human GnRH receptors were suspended in a phosphate-buffered saline supplemented with 5 mM EDTA (PBS-EDTA). The suspension was subjected to centrifugal separation for 5 minutes at 100×g. To the pellet of cells was added 10 ml of a homogenate buffer for cells (10 mM NaHCO$_3$, 5 mM EDTA (ethylenediamine tetracetate), pH 7.5), which was homogenated by using a Polytron homogenizer. Centrifugal separation was conducted for 15 minutes at 400×g. The supernatant was taken into an ultracentrifugal tube, which was subjected to centrifuge for one hour at 100,000×g to give precipitate of the membrane fraction. The precipitate was suspended in 2 ml of the assay buffer (25 mM Tris-HCl, 1 mM EDTA, 0.1% BSA (bovine serum albumin), 0.25 mM PMSF, 1 μg/ml pepstatin, 20 μg/ml leupeptin, 100 μg/ml phosphoramidon, 0.03% sodium azide, pH 7.5), which was centrifuged for one hour at 100,000×g. The membrane fraction recovered as precipitate was again suspended in 20 ml of the assay buffer, which was distributed to vials and stored at −80° C. until used.

(3) Determination of inhibitory rate of $^{125}$I-leuprorelin binding

Membrane fraction of CHO cells expressing human GnRH receptors prepared in the above (2) as diluted with an assay buffer to 200 μg/ml and 188 μl each was distributed into tubes. 2 μl of 2 mM of the compound dissolved in 60% DMSO and 10 μl of 38 nM $^{125}$I-leuprorelin were added simultaneously to the CHO cell membrane fraction expressing human GnRH receptors. For determining the amount of maximum binding, a solution for reaction supplemented with 2 μl of 60% DMSO and 10 μl of 38 nM $^{125}$I-leuprorelin was prepared. And, for determining the amount of non-specific binding, a solution for reaction supplemented with 2 μl of 100 μM leuprorelin dissolved in 60% DMSO and 10 μl of 38 nM $^{125}$I-leuprorelin were also prepared simultaneously.

The reaction was allowed to proceed at 25° C. for 60 minutes. The reaction mixtures were respectively subjected to filtration under sucking with Whatman glass filter (GF-F) processed with polyethylenimine. After completing the filtration, radioactivity of the $^{125}$I-leuprorelin remaining on the filter paper was measured with a γ-counter.

By calculation of

PMB=(TB−SB)/(TB−NSB)×100

(TB: maximum binding radioactivity, SB: radioactivity obtained when a compound was added, NSB: non-specific binding ratio activity, the binding inhibitory rate (PMB) (%) of each test compound was determined. Besides, the inhibitory rates were determined by changing the concentrations of test compounds, and the concentration of a test compound inhibiting the (TB–NSB) by 50%, i.e. the concentration of PMB=50%, (IC$_{50}$ value) was calculated by way of Hill plot.

The compounds obtained in Examples 8(4), 10, 11 or 12 were subjected to the above measurement methods, and obtained IC$_{50}$ values shown in the following Table 4.

TABLE 4

| | $^{125}$I-leuprorelin binding inhibitory rate |
|---|---|
| Test compound | IC$_{50}$ value (nM) human GnRH receptor |
| Compound of Example 8(4) | 1 |
| Compound of Example 10 | 0.3 |
| Compound of Example 11 | 2 |
| Compound of Example 12 | 3 |

Industrial Applicability

The gonadotropin-releasing hormone antagonistic agent of the present invention is stably absorbed through oral administration and shows GnRH antagonistic activity over a long time. Therefore, the present compound can be used as a prophylactic or therapeutic agent for the prevention or treatment of several hormone dependent diseases, for example, a sex hormone dependent cancer, e.g. prostatic cancer pituitary adenoma), cancer of the uterine cervix, breast cancer, prostatic hypertrophy, myoma of the uterus, endometriosis, precocious puberty, amenorrhea syndrome, polycystic ovary syndrome and acne vulgaris, or as a fertility controlling agent, e.g. a contraceptive agent, infertility treating agent, a menstruation controlling agent. Further, in the field of animal husbandry, the gonaolotropin-releasing hormone antagonistic agent of the present invention is effective as an agent of controlling oestrus in animals, improving the quality of edible meat, growth regulation of animals, and also a spawning-accelerating agent in the field of fisheries.

What we claim is:

1. A compound of the formula:

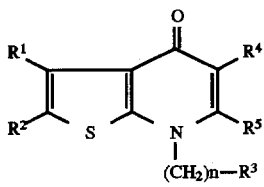

(I)

wherein each of $R^1$ and $R^2$ is independently a hydrogen atom or a group which is (1) an optionally substituted hydrocarbon residue, (2) an optionally substituted acyl group, (3) a carbamoyl group, (4) an optionally substituted heterocyclic group which bonds through a carbon atom of the heterocyclic group, (5) a carboxyl group or an ester or amide thereof, (6) a cyano group, (7) a nitro group, (8) a group of the formula: —NR$^{14}$R$^{15}$, wherein R$^{14}$ is a hydrogen atom, an optionally substituted hydrocarbon residue, an optionally substituted hydrocarbon residue-oxy group, an optionally substituted acyl group, an optionally substituted hydroxyl group, an optionally substituted heterocyclic group, or a group of the formula: —SO$_p$—R$^{16}$, wherein p is an integer of 1 or 2, R$^{16}$ is an optionally substituted hydrocarbon residue, R$^{15}$ is a hydrogen atom or an optionally substituted hydrocarbon residue, and the group —NR$^{14}$R$^{15}$ may form an optionally substituted cyclic amino group, (9) a group of the formula: —O—R$^{17}$, wherein R$^{17}$ is a hydrogen atom, an optionally substituted hydrocarbon residue, an optionally substituted acyl group or an optionally substituted heterocyclic group, or (10) a group of the formula: —S(O)$_t$R$^{18}$, wherein R$^{18}$ is a hydrogen atom, an optionally substituted hydrocarbon residue, or an optionally substituted heterocyclic group, and t is an integer of 0 to 2, R$^3$ is an optionally substituted homo-cyclic group, R$^4$ is (1) an optionally substituted 3- to 8-membered heterocyclic group having at least one nitrogen atom in a ring or (2) a group which is an optionally substituted amino group, an optionally substituted hydroxyl group, or an optionally substituted mercapto group, R$^5$ is hydrogen or a group which is (1) an optionally substituted hydrocarbon residue, (2) an optionally substituted acyl group, (3) a carbamoyl group, (4) an optionally substituted heterocyclic group which bonds through a carbon atom of the heterocyclic group, (5) a carboxyl group or a ester or amide thereof, or (6) a cyano group, n is an integer of 0 to 3, with the proviso that when R$^4$ is tetrazolyl or a group which is (1) a nitro group, (2) a group of the formula: —NR$^{14}$R$^{15}$, wherein R$^{14}$ is a hydrogen atom, an optionally substituted hydrocarbon residue, an optionally substituted hydrocarbon residue-oxy group, an optionally substituted acyl group, an optionally substituted hydroxyl group, an optionally substituted heterocyclic group, or a group of the formula: —SO$_p$—R$^{16}$, where p is an integer of 1 or 2, R$^{16}$ is an optionally substituted hydrocarbon residue, R$^{15}$ is a hydrogen atom or an optionally substituted hydrocarbon residue, and the group —NR$^{14}$R$^{15}$ may form an optionally substituted cyclic amino group, (3) a group of the formula —O—R$^{17}$, wherein R$^{17}$ is a hydrogen atom, an optionally substituted hydrocarbon residue, an optionally substituted acyl group or an optionally substituted heterocyclic group, or (4) a group of the formula: —S(O)$_t$—R$^{18}$, wherein R$^{18}$ is a hydrogen atom, an optionally substituted hydrocarbon residue or an optionally substituted heterocyclic group, and t is an integer of 0 to 2, and n is 1, R$^3$ is not a group of the formula:

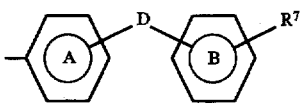

wherein R$^7$ is an optionally substituted 5–7 membered heterocyclic residue, having as a group capable of constituting the ring, carbonyl group, thiocarbonyl group, an optionally oxidized sulfur atom or a group convertible into them, D is a direct bond or a spacer having an atomic length of two or less between the ring B and the ring A, and A and B are independently an optionally substituted aromatic hydrocarbon residue optionally containing a hetero-atom or an optionally substituted heterocyclic residue, or a salt thereof.

2. A compound according to claim 1, wherein R$^1$ is a group which is (1) an optionally substituted hydrocarbon residue, (2) an optionally substituted acyl group, (3) a carbamoyl group, (4) an optionally substituted heterocyclic group which bonds through carbon atom of the heterocyclic group, (5) a carboxyl group or a ester or amide thereof, or (6) a cyano group.

3. A compound according to claim 1, wherein $R^1$ is an optionally substituted $C_{1-20}$ hydrocarbon residue.

4. A compound according to claim 1, wherein $R^1$ is an optionally substituted $C_{1-6}$ alkyl group.

5. A compound according to claim 3, wherein $C_{1-20}$ hydrocarbon residue of $R^1$ is optionally substituted with (1) halogen, (2) nitro, (3) cyano, (4) an optionally substituted amino, (5) an optionally substituted hydroxyl group, (6) a group of the formula: $—S(O)_t—R^6$, wherein t denotes an integer of 0 to 2, and $R^6$ is a hydrogen atom or an optionally substituted hydrocarbon residue.

6. A compound according to claim 1, wherein $R^2$ is an optionally substituted $C_{1-20}$ hydrocarbon residue.

7. A compound according to claim 1, wherein $R^2$ is an optionally substituted $C_{6-14}$ aryl group.

8. A compound according to claim 6, wherein $C_{1-20}$ hydrocarbon residue of $R^2$ is optionally substituted with (1) an optionally substituted amino group, (2) an optionally substituted hydroxyl group, (3) an optionally substituted carbamoyl group, (4) an optionally substituted carboxyl group, (5) an optionally substituted alkenyl group, (6) acyl, or (7) nitro.

9. A compound according to claim 1, wherein $R^3$ is an optionally substituted $C_{6-14}$ aryl group.

10. A compound according to claim 1, wherein the homo-cyclic group $R^3$ is optionally substituted with (1) halogen, (2) nitro, (3) an optionally substituted hydroxyl group, or (4) a group of the formula: $—S(O)_t—R^6$, wherein t denotes an integer of 0 to 2, and $R^6$ is a hydrogen atom or an optionally substituted hydrocarbon residue.

11. A compound according to claim 1, wherein $R^4$ is a 5- to 8-membered heterocyclic group having at least one nitrogen atom in a ring.

12. A compound according to claim 1, wherein $R^4$ is said optionally substituted amino group, optionally substituted hydroxyl group, or said optionally substituted mercapto group.

13. A compound according to claim 1, wherein $R^4$ comprises a substituted heterocyclic group wherein the substituent is (1) halogen, (2) nitro, (3) an optionally substituted hydroxyl group, (4) a group of the formula: $—S(O)_t—R^6$, wherein t denotes an integar of 0 to 2, and $R^6$ is a hydrogen atom or an optionally substituted hydrocarbon residue, (5) an optionally substituted amino, or (6) a $C_{1-10}$ hydrocarbon residue.

14. A compound according to claim 14, wherein $R^4$ comprises a substituted amino group, substituted hydroxyl group, or substituted mercapto group wherein the substituent is (1) a $C_{1-10}$ hydrocarbon residue which may optionally be substituted by $C_{1-6}$ alkoxy-carbonyl or carbamoyl, (2) a $C_{1-10}$ acyl group, or (3) a group of the formula: $—S(O)_t—R^6$, wherein t denotes an integer of 0 to 2, and $R^6$ is a hydrogen atom or an optionally substituted hydrocarbon residue.

15. A compound according to claim 1, wherein $R^5$ is a hydrogen atom or an optionally substituted $C_{1-20}$ hydrocarbon residue.

16. A compound according to claim 15, wherein the hydrocarbon residue in the optionally substituted $C_{1-20}$ hydrocarbon residue is $C_{1-10}$ alkyl group.

17. A compound according to claim 1, wherein $R^1$ is an $C_{1-6}$ alkyl group which may optionally be substituted with halogen or $N—C_{7-13}$ aralkyl-$N—C_{1-6}$ alkylamino, $R^2$ is a $C_{6-14}$ aryl group which may optionally be substituted with a group selected from the group consisting of (i) nitro, (ii) $C_{1-6}$ alkoxy and (iii) amino which may optionally be substituted with $C_{1-6}$ alkanoyl, $R^3$ is a mono- or di-halogeno $C_{6-14}$ aryl group, $R^4$ is (1) a 5- or 6-membered heterocyclic group which has at least one nitrogen atom and one oxygen atom and which is bonded through a carbon atom, (2) a hydroxyl group which may optionally be substituted with a group selected from the group consisting of (i) $C_{1-6}$ alkyl which may optionally be substituted with $C_{1-6}$ alkoxycarbonyl or carbamoyl, (ii) $C_{1-6}$alkanoyl and (iii) $C_{1-6}$alkylsulfonyl, (3) a group of the formula: $—S(O)_t—R^{6'}$, wherein t is an integer of 0 to 2 and $R^{6'}$ is $C_{1-6}$alkyl, or (4) an amino group which may optionally be substituted with $C_{1-6}$alkanoyl, $R^5$ is a hydrogen atom or $C_{1-10}$ alkyl, and n is 1.

18. 4,7-dihydro-2-(4-methoxyphenyl)-3-(N-benzyl-N-methylaminomethyl)-5-(oxazol-5-yl)-7-(2-fluorobenzyl)-4-oxothieno[2,3-b]pyridine or its salt.

19. 4,7-dihydro-2-(4-isobutyrylaminophenyl)-3-(N-benzyl-N-methylaminomethyl)-5-(isopropoxy)-7-(2,6-difluorobenzyl)-4-oxothieno[2,3-b]pyridine or its salt.

20. 3-(N-benzyl-N-methylaminomethyl)-4,7-dihydro-2-(4-isobutyrylaminophenyl)-5-(isopropylsulfonyloxy)-7-(2,6-difluorobenzyl)-4-oxothieno[2,3-b]pyridine or its salt.

21. A method for producing a compound of the formula:

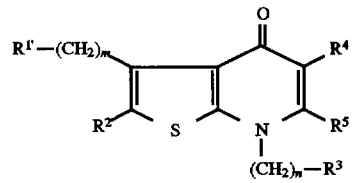

[III]

wherein $R^{1'}$ is a group which is (1) a nitro group, or (2) a group of the formula $NR^{14}R^{15}$, wherein $R^{14}$ is a hydrogen atom, an optionally substituted hydrocarbon residue, an optionally substituted hydrocarbon residue-oxy group, an optionally substituted acyl group, an optionally substituted hydroxyl group, an optionally substituted heterocyclic group, or a group of the formula $—SO_p—R^{18}$, wherein p is an integer of 1 or 2, $R^{18}$ is an optionally substituted hydrocarbon residue, $R^{15}$ is a hydrogen atom or an optionally substituted hydrocarbon residue, and the group $—NR^{14}R^{15}$ may form an optionally substituted cyclic amino group, $R^2$, $R^3$, $R^4$ and $R^5$ have the same meaning as defined in claim 1, n is an integer of 0 to 3, m is an integer of 0 to 6, or a salt thereof, which comprises reacting a compound of the formula:

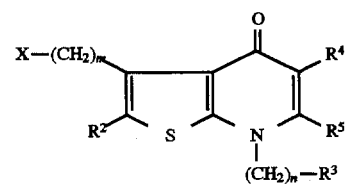

[II]

wherein X is a leaving group and the other groups have the same meaning as defined above, with a compound of the formula:

$R^{1'}—H$ wherein $R^{1'}$ has the same meaning as defined above.

22. A pharmaceutical composition, which comprises a compound as defined in claim 1 and a carrier, excipient or diluent thereof.

23. A method for treating a mammal suffer from a gonadotropin-releasing hormone derived disorder, which comprises administering an effective amount of a compound as defined in claim 1 to the mammal.

24. The method of claim 23, wherein the gonadotropin-releasing hormone derived disorder is a sex hormone dependent disease.

25. A compound according to claim 1, wherein $R^2$ is a group which is (1) an optionally substituted hydrocarbon residue, (2) an optionally substituted acyl group, (3) a carbamoyl group, (4) an optionally substituted heterocyclic group which bonds through a carbon atom of the heterocyclic group, (5) a carboxyl group or an ester or amide thereof, or (6) a cyano group.

26. A compound according to claim 6, wherein the $C_{1-20}$ hydrocarbon residue of $R^2$ is optionally substituted with (1) an alkoxy group, (2) an alkylcarbonyl group, (3) an alkylaminocarbonyl group, (4) an optionally substituted alkenyl, or (5) an optionally substituted amino.

27. A compound according to claim 17, wherein $R^3$ is a phenyl group substituted by one or two halogens.

28. A compound according to claim 6 wherein $R^4$ is optionally substituted oxazolyl, isoxazolyl, thiazolyl, imidazolyl, triazolyl, oxoimidazolyl, or thiazinyl.

* * * * *

UNITED STATES PATENT AND TRADEMARK OFFICE
CERTIFICATE OF CORRECTION

PATENT NO. : 5,744,479
DATED : April 28, 1998
INVENTOR(S) : Shuichi FURUYA, et al.

It is certified that error appears in the above-identified patent and that said Letters Patent is hereby corrected as shown below:

On title page, insert -- [63] Continuation of PCT No: PCT/JP96/03018, Filing Date October 18, 1996 --;

Column 1, line 4, please delete "PCT/JP96/08018" and replace with --PCT/JP96/03018--

Signed and Sealed this

Twenty-eighth Day of November, 2000

Attest:

Attesting Officer

Q. TODD DICKINSON

Director of Patents and Trademarks